(12) United States Patent
Roth et al.

(10) Patent No.: US 11,293,053 B2
(45) Date of Patent: Apr. 5, 2022

(54) BIFUNCTIONAL OLIGONUCLEOTIDE PROBE FOR UNIVERSAL REAL TIME MULTIANALYTE DETECTION

(71) Applicant: ALBERT-LUDWIGS-UNIVERSITAET FREIBURG, Freiburg (DE)

(72) Inventors: Guenter Roth, Freiburg (DE); Bernd Faltin, Freiburg (DE); Felix Von Stetten, Freiburg (DE); Simon Wadle, Freiburg (DE)

(73) Assignee: ALBERT-LUDWIGS-UNIVERSITAET FREIBURG, Freiburg (DE)

( * ) Notice: Subject to any disclaimer, the term of this patent is extended or adjusted under 35 U.S.C. 154(b) by 435 days.

(21) Appl. No.: 14/357,574

(22) PCT Filed: Nov. 12, 2012

(86) PCT No.: PCT/EP2012/072402
§ 371 (c)(1),
(2) Date: May 12, 2014

(87) PCT Pub. No.: WO2013/079307
PCT Pub. Date: Jun. 6, 2013

(65) Prior Publication Data
US 2014/0315747 A1  Oct. 23, 2014

(30) Foreign Application Priority Data
Nov. 10, 2011  (DE) .......................... 102011055247.2

(51) Int. Cl.
C12P 19/34  (2006.01)
C12Q 1/6823  (2018.01)
(Continued)

(52) U.S. Cl.
CPC ......... *C12Q 1/6823* (2013.01); *C12Q 1/6818* (2013.01); *C12Q 1/6876* (2013.01)

(58) Field of Classification Search
USPC .......... 435/6.1, 6.11, 6.12, 91.1, 91.2, 91.51, 435/183; 436/94, 501; 536/23.1, 24.3,
(Continued)

(56) References Cited

U.S. PATENT DOCUMENTS 4,751,177 A   6/1988  Stabinsky
5,641,658 A   6/1997  Adams et al.
(Continued)

FOREIGN PATENT DOCUMENTS

DE   10316159 A1   10/2004
JP   2008245641   10/2008
(Continued)

OTHER PUBLICATIONS

"Molecular beacon" from Wikipedia, the free encyclopedia. Printed on Jul. 4, 2019.*
(Continued)

*Primary Examiner* — Frank W Lu
(74) *Attorney, Agent, or Firm* — Agris & Von Natzmer, LLP; Joyce Von Natzmer

(57) ABSTRACT

The invention relates to a mediator probe comprising a probe region and a mediator region. Furthermore, the invention relates to a system comprising a mediator probe and a detection molecule, use of that system and a method for detection of at least one target molecule.

6 Claims, 25 Drawing Sheets

Specification includes a Sequence Listing.

(51) Int. Cl.
*C12Q 1/6818* (2018.01)
*C12Q 1/6876* (2018.01)

(58) Field of Classification Search
USPC .................................. 536/24.33, 25.3, 25.32
See application file for complete search history.

(56) References Cited

U.S. PATENT DOCUMENTS

| | | | |
|---|---|---|---|
| 5,653,939 | A | 8/1997 | Hollis et al. |
| 6,099,803 | A | 8/2000 | Ackley et al. |
| 6,238,869 | B1 | 5/2001 | Kris et al. |
| 6,300,070 | B1 | 10/2001 | Boles et al. |
| 2001/0034025 | A1 | 10/2001 | Modlin et al. |
| 2002/0110826 | A1 | 8/2002 | Dattagupta |
| 2004/0014078 | A1 | 1/2004 | Xia et al. |
| 2004/0101835 | A1 | 5/2004 | Willis et al. |
| 2007/0122804 | A1 | 5/2007 | Fu |
| 2009/0253142 | A1* | 10/2009 | Allawi ................. C12Q 1/6827 435/6.1 |

FOREIGN PATENT DOCUMENTS

| | | |
|---|---|---|
| WO | 1998003678 A1 | 1/1998 |
| WO | 2001006012 A1 | 1/2001 |
| WO | 2009/117327 A2 | 9/2009 |
| WO | 2012096523 A9 | 1/2014 |

OTHER PUBLICATIONS

"Most Common Polymerase". Printed on Jun. 18, 2021.*
DNA polymerase IV from Wikipedia. Printed on Jun. 18, 2021.*
Brunk et al., Analysis of Specific Bacteria from Environmental Samples using Quantitative Polymerase Chain Reaction, Curr. Issues Mol. Biol., vol. 4, 2002, pp. 13-18.
Faltin et al., Mediator Probe PCR: A Novel Approach for Detection of Real-Time PCR Based on Label-Free Primary Probes and Standardized Secondary Universal Fluorogenic Reporters, Clinical Chemistry, vol. 58:11, 2012, pp. 1546-1556.
Hall et al., Sensitive detection of DNA polymorphisms by the serial invasive signal amplification reaction, PNAS, Jul. 18, 2000, vol. 97, No. 15, pp. 8272-8277.
Huang et al., Multiplex Fluorescence Melting Curve Analysis for Mutation Detection with Dual-Labeled, Self-Quneched Probes, PLoS ONE, vol. 6, Apr. 2011, pp. e19206.
Iniplex, "Inplex Technology," Google 2009, Retrieved from the Internet: http://www.inplexcf.com/laboratory/inplextechnology.html, retrieved on Mar. 19, 2013.
Li et al., Universal Molecular Beacon-Based Tracer System for Real-Time Polymerase Chain Reaction, Anal. Chem., 2006, vol. 78, pp. 7886-7890.
Lockett et al., Molecular Beacon-Style Hybridization Assay for Quantitative Analysis of Surface Invasive Cleavage Reactions, Anal. Chem., 2007, vol. 79, pp. 6031-6036.
Lu et al., A Surface Invasive Cleavage Assay for Highly Parallel SNP Analysis, Human Mutation, vol. 19, 2002, pp. 416-422.
Nuovo et al., In Situ Amplification Using Universal Energy Transfer-labeled Primers, The Journal of Histochemistry & Cytochemistry, 1999, vol. 47, No. 3, pp. 273-279.
Sun et al., Electrochemical DNA Biosensor Based on Proximity-Dependent DNA Ligation Assays with DNAzyme Amplification of Hairpin Substrate Signal, Biosensors and Bioelectronics, vol. 25, 2010, pp. 2483-2489.
Tsourkas et al., Shedding Light on Health and Disease using Molecular Beacons, Briefings in Functional Genomics and Proteomics, vol. 1, No. 4, Jan. 2003, pp. 372-384.
Van Doorn, Robust Detection and Identification of Multiple Oomycetes and Fungi in Environmental Samples by Using a Novel Cleavable Padlock Probe-Based Ligation Detection Assay, Appl. Environ. Microbiol., vol. 75, No. 12, 2009, pp. 4185-4193.
Nikolaus et al., DNA-Aptamers Binding Aminoglycoside Antibiotics, Sensors 2014, 14, 3737-3755; doi:10.3390/s140203737.
Office Action dated Sep. 13, 2016 by the JPO for Japanese Application JP2014-540506 including English translation thereof.

* cited by examiner

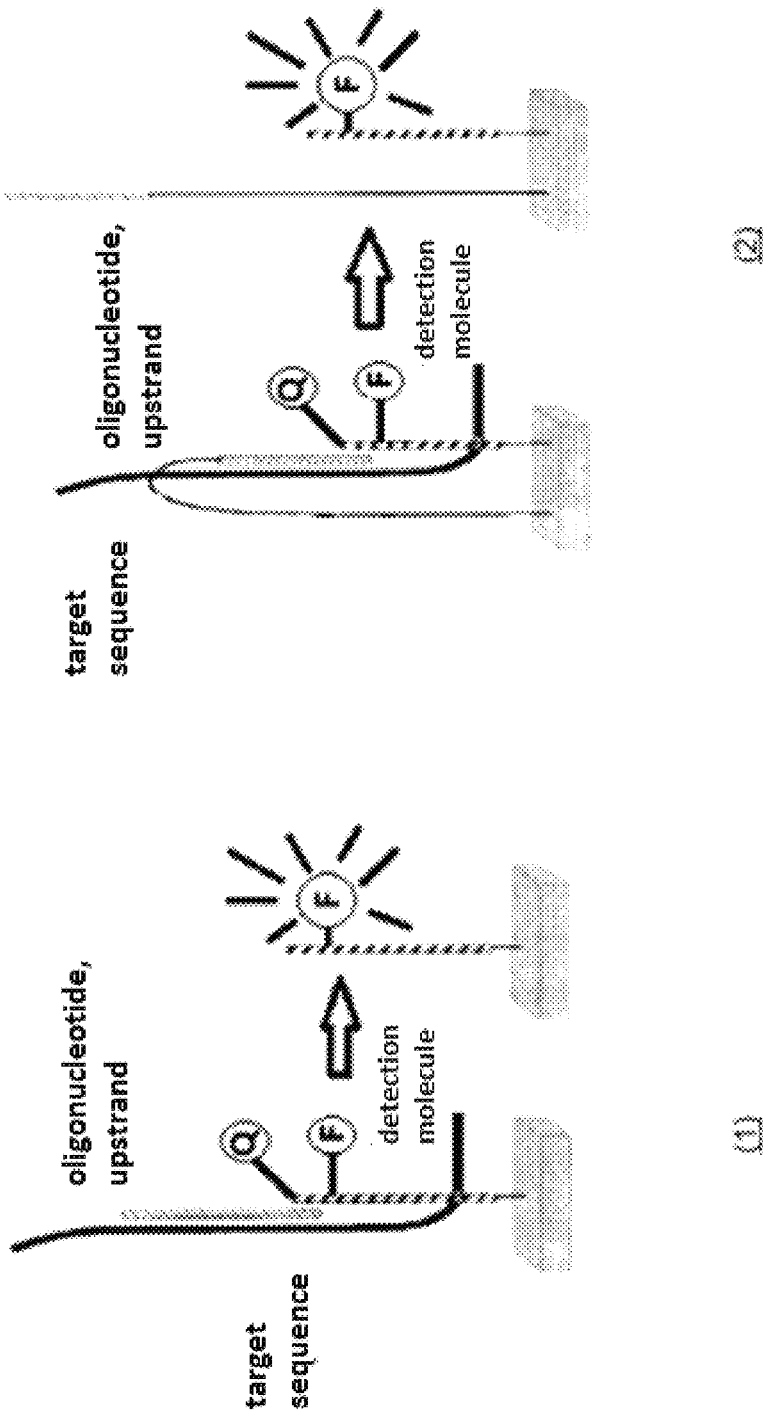

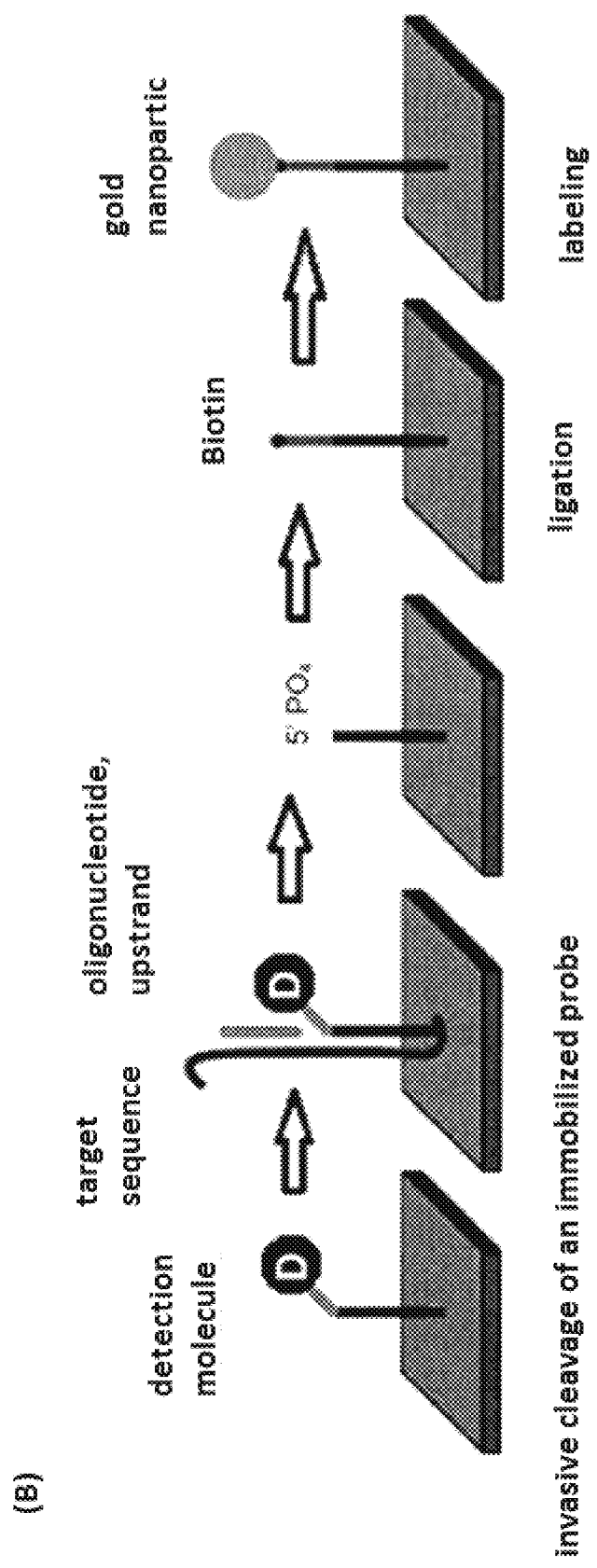

(D)

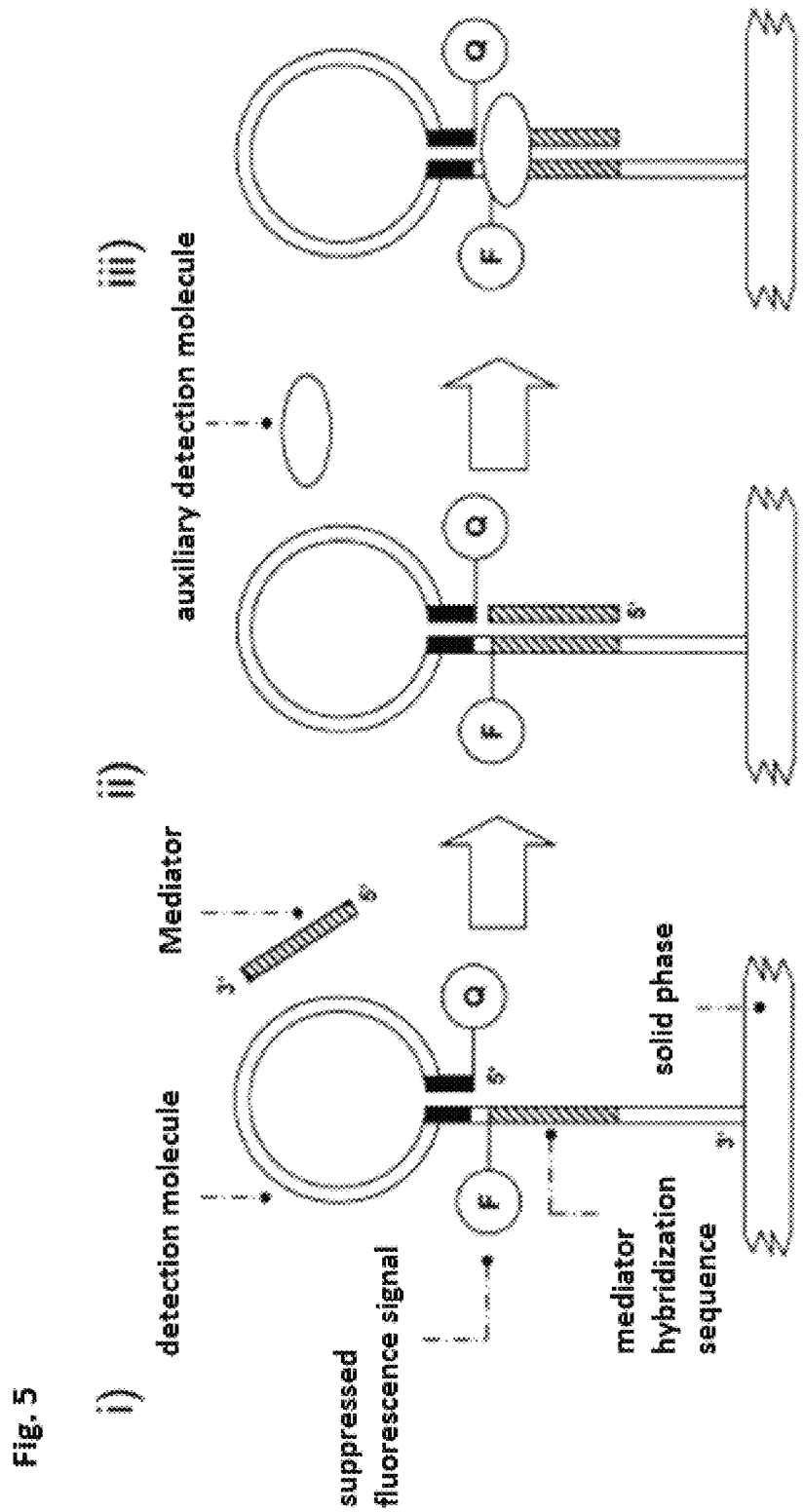

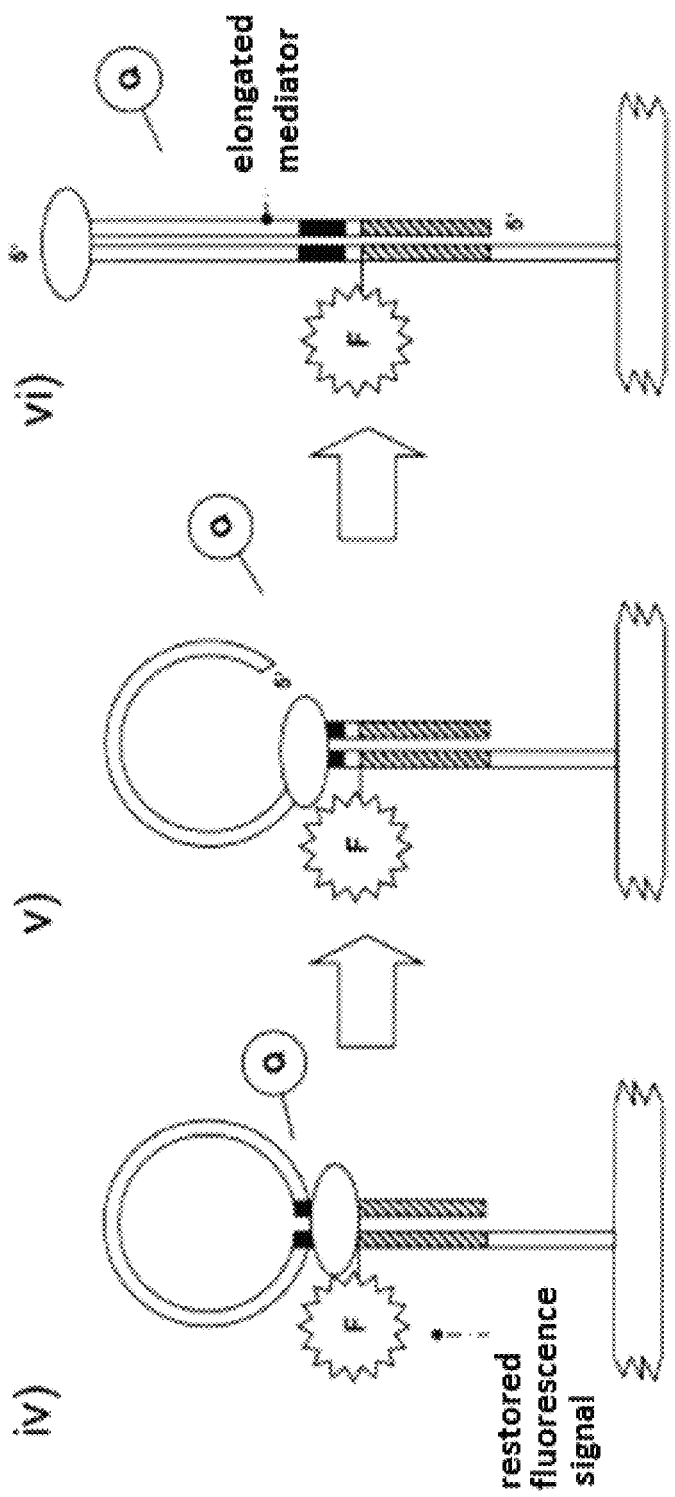

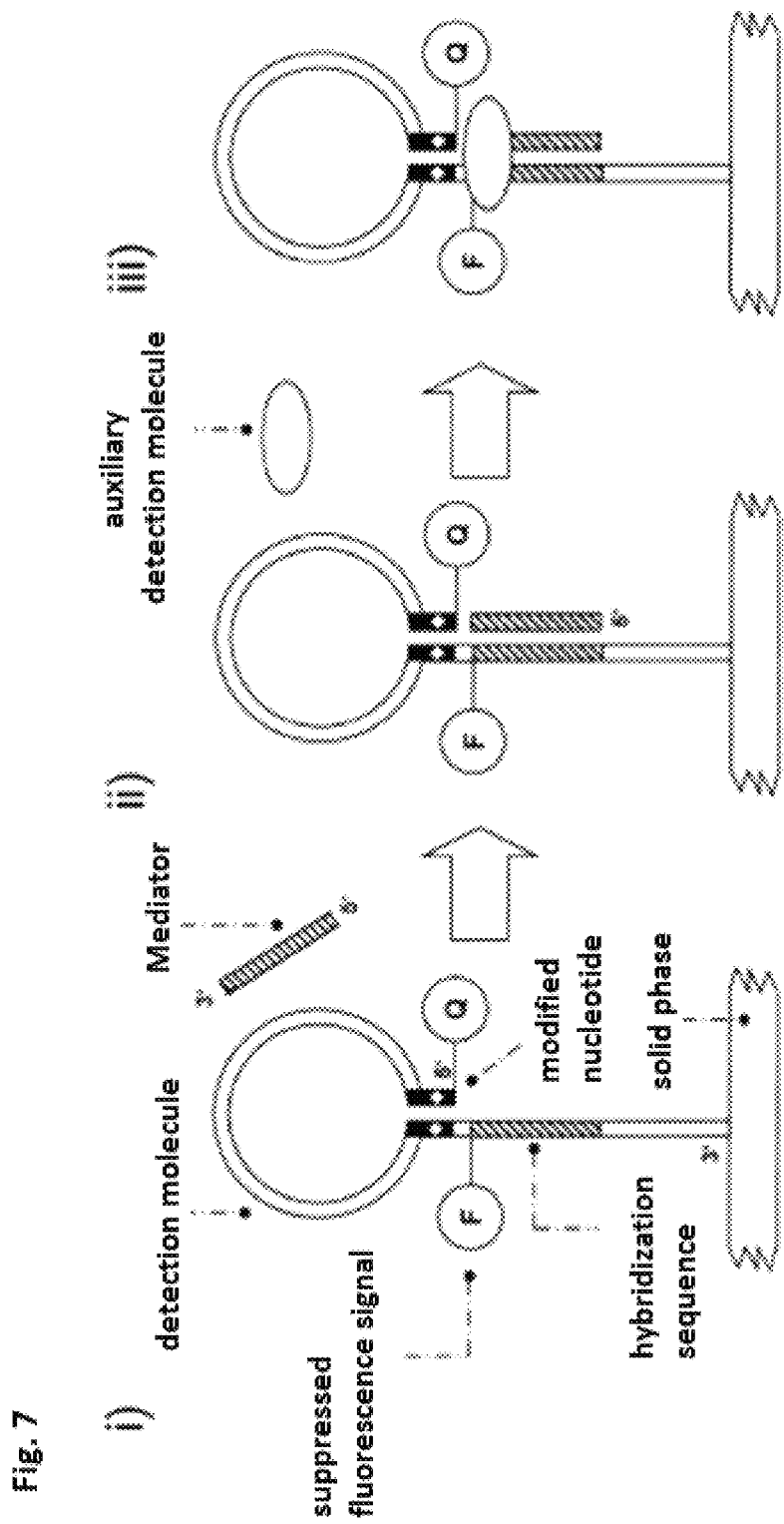

A

A

SEQUENCE LISTING

<160> NUMBER OF SEQ ID NOS: 20

<210> SEQ ID NO 1
<211> LENGTH: 66
<212> TYPE: DNA
<213> ORGANISM: Artificial Sequence
<220> FEATURE:
<223> OTHER INFORMATION: Sonde

<400> SEQUENCE: 1
ccgcagaaga tgagatcgcg gtgttggtcg tagagcccag aacgattttt tttttttttt    60
tttttt                                                              66

<210> SEQ ID NO 2
<211> LENGTH: 66

<212> TYPE: DNA
<213> ORGANISM: Artificial Sequence
<220> FEATURE:
<223> OTHER INFORMATION: Sonde

<400> SEQUENCE: 2
ccgcagaaga tgagatcgcg gtgttcactg accgaactgg agcattttt ttttttttt    60 tttttt                                                             66

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ggcaattgcg gcatgttctt cc                                           22

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
tgttgcattt gcagacgagc ct                                           22

<210> SEQ ID NO 5
<211> LENGTH: 27
<212> TYPE: DNA
<213> ORGANISM: Artificial Sequence
<220> FEATURE:
<223> OTHER INFORMATION: Sonde

<400> SEQUENCE: 5
atgcgaacgg cggcaacggc aacatgt                                      27

<210> SEQ ID NO 6
<211> LENGTH: 44
<212> TYPE: DNA
<213> ORGANISM: Artificial Sequence
<220> FEATURE:
<223> OTHER INFORMATION: Sonde

<400> SEQUENCE: 6
aaatcgttct gggctctacg cgaacggcgg caacggcaac atgt                   44

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
agatgcacgt actgctgaaa tgag                                         24

<210> SEQ ID NO 8
<211> LENGTH: 26
<212> TYPE: DNA
<213> ORGANISM: Artificial Sequence
<220> FEATURE:
<223> OTHER INFORMATION: Primer

```
<400> SEQUENCE: 8
aataaagtac ggatcaacag ctaaac                                            26

<210> SEQ ID NO 9
<211> LENGTH: 20
<212> TYPE: DNA
<213> ORGANISM: Artificial Sequence
<220> FEATURE:
<223> OTHER INFORMATION: Sonde

<400> SEQUENCE: 9
ccgcctactc ctggaccagg                                                   20

<210> SEQ ID NO 10
<211> LENGTH: 48
<212> TYPE: DNA
<213> ORGANISM: Artificial Sequence
<220> FEATURE:
<223> OTHER INFORMATION: Sonde

<400> SEQUENCE: 10
aaatcgttct gggctctacg gtattcacag tggtaaaggc ggacaaca                    48

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
gctggcagct ctagattatt aactg                                             25

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
ggtcaggtaa ctgcacccta a                                                 21

<210> SEQ ID NO 13
<211> LENGTH: 20
<212> TYPE: DNA
<213> ORGANISM: Artificial Sequence
<220> FEATURE:
<223> OTHER INFORMATION: Sonde

<400> SEQUENCE: 13
ggttcctgca ggtggtggca                                                   20

<210> SEQ ID NO 14
<211> LENGTH: 39
<212> TYPE: DNA
<213> ORGANISM: Artificial Sequence
<220> FEATURE:
<223> OTHER INFORMATION: Sonde

<400> SEQUENCE: 14
aaatcgttct gggctctacg gttcctgcag gtggtggca                              39

<210> SEQ ID NO 15
<211> LENGTH: 25
```

-continued

```
<212> TYPE: DNA
<213> ORGANISM: Artificial Sequence
<220> FEATURE:
<223> OTHER INFORMATION: Primer

<400> SEQUENCE: 15
tcacccacac tgtgcccatc tacga                                          25

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
cagcggaacc gctcattgcc aatgg                                          25

<210> SEQ ID NO 17
<211> LENGTH: 26
<212> TYPE: DNA
<213> ORGANISM: Artificial Sequence
<220> FEATURE:
<223> OTHER INFORMATION: Sonde

<400> SEQUENCE: 17
atgccctccc ccatgccatc ctgcgt                                         26

<210> SEQ ID NO 18
<211> LENGTH: 26
<212> TYPE: DNA
<213> ORGANISM: Artificial Sequence
<220> FEATURE:
<223> OTHER INFORMATION: Sonde

<400> SEQUENCE: 18
atgccctccc ccatgccatc ctgcgt                                         26

<210> SEQ ID NO 19
<211> LENGTH: 43
<212> TYPE: DNA
<213> ORGANISM: Artificial Sequence
<220> FEATURE:
<223> OTHER INFORMATION: Sonde

<400> SEQUENCE: 19
aaatcgttct gggctctacg ccctccccca tgccatcctg cgt                      43

<210> SEQ ID NO 20
<211> LENGTH: 43
<212> TYPE: DNA
<213> ORGANISM: Artificial Sequence
<220> FEATURE:
<223> OTHER INFORMATION: Sonde

<400> SEQUENCE: 20
atgctccagt tcggtcagtg cccctccccca tgccatcctg cgt                     43
```

BIFUNCTIONAL OLIGONUCLEOTIDE PROBE FOR UNIVERSAL REAL TIME MULTIANALYTE DETECTION

CROSS-REFERENCE TO RELATED APPLICATIONS

This is the U.S. national stage of International application PCT/EP2012/072402, filed Nov. 12, 2012 designating the United States and claiming priority to German application DE 102011055247.2, filed Nov. 10, 2011.

INCORPORATION OF SEQUENCE LISTING

The sequence listing was filed as a text file as part of International application PCT/EP2012/072402, filed Nov. 12, 2012 is hereby incorporated by reference. An extra copy of this text file (converted into ASCII for compliance with the US EFS system) named "eolf-seql-ASCII-copy.txt", which is 4 kilobytes (measured in MS-WINDOWS), dated May 11, 2014 was downloaded from WIPO, converted into ASCII and is submitted herewith via the USPTO EFS system.

The invention relates to a mediator probe comprising a probe region and a mediator region. Furthermore, the invention relates to a system comprising a mediator probe and a detection molecule, use of that system and a method for detection of at least one target molecule.

PRIOR ART

Numerous research methods in molecular biology permitting detection and optional analysis of a sample have been described in the prior art. One of these methods is detection and parallel analysis of several thousand individual detections in a small quantity of biological sample material by means of a microarray. There are various forms of microarrays, which are sometimes also referred to as "gene chips" or biochips," because, like a computer chip, they may contain a great deal of information in a very small space.

Microarrays permit highly parallel detection of various analytes on a substrate, which is typically planar. The immobilized probe molecules of a microarray are immobilized and/or synthesized on a suitable substrate in the course of the production process in a defined location (spot) on a grid (array) by transfer of small volumes of liquid. This two-dimensional, spatially resolved immobilization of capture molecules may be designed so that nucleic acids or peptides and/or proteins can be detected. As a rule, in situ lithography methods only allow synthesis of short oligonucleotides and/or amino acid chains. The DNA microarrays that are produced can be stored for months under suitable conditions, but protein arrays can be stored only for a short period of time.

For a microarray analysis, the sample to be analyzed is mixed with a suitable buffer and incubated with the microarray accordingly, so that typically a hybridization event occurs with complementary sequence segment. Based on the low sensitivity of microarray systems, the sample is amplified in a previous reaction step in the case of a nucleic acid to be detected (for example, by means of polymerase chain reaction (PCR), RT-PCR or whole genome amplification (WGA)) and is labeled with a fluorescent dye for detection or incubated with an additional detection probe on the microarray, for example. Peptides and proteins cannot be amplified enzymatically and are concentrated by purification of the sample to be analyzed. On the other hand, there are approaches in which signal amplification is performed on the microarray after successful hybridization by means of rolling circle amplification (RCA), for example. This procedure includes several time-consuming steps and increases the risk of inaccuracy and contamination. Typical applications include microarrays in expression analyses as well as detection of pathogens or resistance markers. An overview of various synthesis techniques and applications is available in the prior art for those skilled in the art.

In the prior art, the hybridization of amplified DNA fragments on immobilized allele-specific oligonucleotides has been described and is considered one of the routine methods available to those skilled in the art. A preceding amplification step with primer molecules in various concentrations allows single-stranded labeled DNA, which preferably interacts with the capture molecules of the microarray to be generated. After transferring the medium to a microarray, detection can be performed directly by means of fluorescence or by using biotin-labeled primers after successful hybridization, so that the hybridization step is followed by incubation in particular with a streptavidine-modified horseradish peroxidase, which converts a soluble substrate into an insoluble reaction product. By detection of the chromogenic precipitate, a binding event between the target molecule and the capture molecule can be detected. An elongation reaction of an immobilized primer may optionally be performed after hybridization of the preamplified target sequence(s), in which the biotin-labeled nucleotides are incorporated. After incubation with a streptavidine-modified alkaline phosphatase and after addition of a suitable substrate, the presence of the target sequence can be detected by forming a chromogenic reaction product.

In another embodiment (multiplex quantitative DNA array-based PCR, MQDA-PCR), the nucleic acid to be detected is first amplified in parallel with bifunctional primers for a few PCR cycles. This yields amplification products having a universal 5' end, which then permits competitive quasi-monoplex amplification with universal primers. Next, in a separate step, a target sequence-specific probe is labeled by addition of a modified nucleotide and hybridized on a microarray. By using bifunctional primers, a two-step PCR reaction with an increased degree of multiplexing can be performed without significantly influencing the reaction efficiency by different sequences. The complex procedural protocol has a negative effect on integration into the work sequence. Repeated addition and removal of reagents and/or reaction products and also the transfer of the reaction batch between multicontainers involve a great deal of effort ("hands-on time"), long waiting times ("time to result") and the risk of procedural errors. In addition to preparing the batches for the individual PCR reactions, the procedure involves multiple incubation steps in which the bifunctional primers are digested, for example, the probes are labeled and the incubated on the microarray. This yields a direct correlation between the target sequence to be detected and the immobilized capture molecule on the chip surface. Therefore, this method cannot be adapted to differing target sequences without producing a new microarray. Another disadvantage of these methods is that the sample material must be transferred between two reaction vessels after the amplification, but this may involve procedural errors and contamination.

One possibility of minimizing the risk of contamination is to perform amplification and hybridization in a reaction vessel. By spatially separating two reaction compartments, different reactions may take place in one vessel so that they are separate from one another in time. The prior art has described a "microarray-in-a-tube" system, in which two compartments and one buffer reservoir are integrated into a reaction vessel (Liu, Q. et al., 2007, Microarray-in-a-tube for detection of multiple viruses, Clin. Chem., 53, 188-194). By inverting the vessel, the liquid is transferred from the bottom section to the top section and mixed with a previous reaction buffer, so that the reaction vessel need not be opened. An amplification step can thus be performed with a subsequent hybridization without having to transfer the reaction medium between two vessels or having to work with active elements. Since the immobilized capture molecules depend on the target sequence to be detected, only selected sequences can be detected with a specific array layout. The microarray that is produced in this way therefore cannot be adapted to newly selected target sequences and must be produced in a new work sequence, if necessary, and then integrated into the system.

In addition, it has been described in the prior art that the detection of specific nucleic acids in a reaction batch may be performed by strand elongation of an immobilized probe. To do so, the target sequence is amplified in the presence of dUTP and then is enzymatically fragmented by means of uracil-N-glycosylase in a downstream step in segments approximately 20 to 50 base pairs long. Next, the batch is incubated on a microarray consisting of target sequence-complementary probes immobilized at the 5' terminus. After hybridization, a duplex is typically formed, in which the 5' region of the target molecule overlaps with the 3' region of the probe. After removing the unbound fragments, the array is incubated with a reaction mix, which contains a polymerase and labeled ddNTPs, among other things. The labeling (fluorescent dye) is different for each of the four nucleotides. The use of ddNTPs allows specific addition of precisely one nucleotide to the solid-phase probe in the presence of the complementary target sequence because no other nucleotide can be linked to ddNTPs. With suitable detection methods, it is thus possible to determine which nucleotide has been attached to which probe segment. Therefore, if suitable probe segments are used, this method is suitable for detection of the target sequence and for sequencing. In a special embodiment the method allows a high degree of multiplexing and allows parallel SNP detection of up to 640 target sequences.

Like other state-of-the-art methods, in which a reaction batch must be transferred after performing amplification, there is the risk of contamination and procedural errors with this batch as well. Solid-phase on-chip probes must typically cover the complete locus to be detected, so that multiple probes are needed for each sequence segment.

U.S. Pat. No. 5,641,658 and U.S. Pat. No. 6,300,070 B1 both describe PCR-based amplification methods, in which the required primer molecules are immobilized on a solid phase. As a result, the amplified nucleic acid molecules are also present exclusively on the solid phase. In the presence of the target sequence in the sample to be analyzed, the nucleic acid can bind to "primer 1" and can elongate it enzymatically. In the recurring denaturing step, the nucleic acid template dissociates from the newly formed nucleic acid strand and is thus available in the next annealing cycle. In the next cycle, the amplification product thus formed can hybridize with an immobilized "primer 2" which can be elongated and which also forms an immobilized nucleic acid strand. The nucleic acid strands formed by this procedure can interact with other primer molecules and may serve as nucleic acid template. This method of detecting nucleic acids is known as "bridge TM-PCR."

By immobilizing various primer pairs in a defined array, multiple target sequences can be detected in parallel due to the degree of multiplexing thus achieved. One disadvantage of this method is the need for the various primer molecules to be homogeneous and to be distributed with a sufficient density in the respective spot so that the nucleic acid strand formed by elongation of the primer can have a sufficient number of additional interaction partners for the next cycles. The reaction efficiency of this solid-phase PCR is thus approximately 30%, so that the amount of linear interphasic amplification is approximately 10 times greater than that of surface amplification. By using primers immobilized in hydrogel and additional primers in the liquid phase for these studies, Pemov et al. arrived at comparable reaction efficiencies ($\approx 34\%$) (Pemov, A. et al., 2005, DNA analysis with multiplex microarray-enhanced PCR. Nucleic Acids Res., 33, e11). The 5' immobilized primers consist of two functional segments and are each made up of a universal 5' region and a target sequence-specific 3' region. Universal primers present freely in the reaction solution have the same identical sequence as the universal segments of the solid-phase primers. A modified copy of the target sequence is formed in a sequence of interphasic amplification and solid-phase amplification and can be amplified in a quasi-monoplex PCR using universal liquid-phase primers. This solid-phase-supported multiplexing method has the disadvantage that post-PCR steps (for example, incubation with modified detection oligonucleotides and/or washing steps and incubation steps) must be performed after incorporation of modified nucleotides.

Nested solid-phase PCR is another method described in the prior art for immobilizing amplification products on a solid phase during an amplification step (nested on-chip PCR (NOC PCR)). This method uses at least three different primer molecules, two of which form the external primer pair (P1 and P2), while the third primer molecule (P3) is bound within a segment bordered by P1 and P2 and P3 is immobilized on a solid phase. P1 and P2 are present in excess in comparison with P3. This method is a combined liquid-phase/solid-phase amplification system. The advantages of this method lie in the increased sensitivity and specificity, as is the case with nested PCR. Through suitable immobilization methods and choice of substrate, there can be highly parallel detection of multiple target sequences. The analysis may be performed by sequence-specific probes or labeled nucleotides, and real-time detection is possible with the latter variant. One disadvantage of this approach is the use of target sequence-specific P3 primer molecules, where the sequence correlates directly with the target molecule.

The use of immobilized primer molecules for specific detection of nucleic acids is not limited to PCR-based methods alone. It is described in the prior art that isothermal detection of pathogens has been performed successfully within 120 minutes by using helicase-dependent amplification (HDA). The amplification product is labeled with fluorescence-labeled reverse primers. After performing the reaction, the chip is washed and the fluorescence signal is analyzed. To perform a specific sensitive reaction, the reaction batch must be heated to 65° C. In addition, the chip must be connected to a pump element, so that the relatively large sample volume of 50 µL is adequately mixed. Connection of active actuators to a biochip is generally regarded as a disadvantage and increases the labor involved. The sensitivity achieved is too low for clinical diagnostic purposes. Thus, for example, the limit of detection has been described as being $5 \cdot 10^4$ genome equivalents of *Staphylococcus*

*aureus* and 1.3·10⁵ genome equivalents of *Neisseria gonorrhoeae* (Andresen, D., von Nickisch Rosenegk, M. and Bier, F. F., 2009, Helicase-dependent on-chip amplification and its use in multiplex pathogen detection, Clin. Chim. Acta, 403, 244-248). The biochip produced by this method is to be used exclusively for detection of defined target sequences because analyte-specific nucleotides are present in immobilized form.

In addition, methods have been disclosed in the prior art, describing detection of the target sequence in real time and/or without additional processing steps. These methods are implemented by a combined amplification and detection system. For example, it has been written that it is possible to perform parallel detection and quantification of three different viruses in the donor plasma samples. An external primer pair and an internal primer pair are needed, the external pair being used in a reverse transcription. The internal pair, in which the forward primer is immobilized in a hydrogel pad, while the reverse primer is present freely in the liquid phase, is used for the on-chip PCR. By using a suitable dye the double-stranded amplification products in the spots are marked and detected during the annealing step. This method has a dynamic range of 6 log($10^0$ to $10^6$ copies). Use of a sequence-nonspecific dye allows universal detection of any double-stranded amplification products. However, the disadvantage is that no specificity is ensured, so that nonspecific amplification products cannot be differentiated.

DE 103 16 159 A1 describes a method in which target sequence-specific primer molecules are immobilized in a flow cell that can be thermally regulated. The flow cell also has the property of conducting the excitation light through a surface, usually planar, by means of total internal resonance fluorescence (TIRF). After adding the target sequence and typical PCR reagents as well as fluorescence-labeled nucleotides (for example, Cy5-dUTP), DNA-dependent solid-phase primer elongation can be detected by suitable methods.

Liu et al. developed a multiplex analysis for nucleic acids, which combines amplification by PCR and detection by microarray analysis in one reaction (Liu, H. P. et al., 2006, TaqMan probe array for quantitative detection of DNA targets, Nucleic Acids Research, 34). This is done by means of primer molecules in the liquid phase and an array of target sequence-specific 3'-immobilized TaqMan probes. In the presence of the complementary target sequence, a TaqMan probe is cleaved by a polymerase, thus restoring a suppressed fluorescence signal. The locally resolved signal can be detected by means of optical devices. This platform was used to detect five different target sequences in one sample. This batch is potentially also suitable for real-time analysis. Since the primers are present freely in the reaction solution, the enzymatic amplification of the target sequence may also take place exclusively in the liquid phase. The probe is not a necessary interaction partner and therefore the amplification reaction is optionally not imaged on the solid phase by a fluorescence signal. Additional fluorophore-labeled oligonucleotide probes are used for the specific detection of target sequences. The use of molecular beacons as biosensors for sensitive and specific nucleic acid detection has been described in the prior art. The use of molecular beacons or TaqMan probes for microarray analyses has the advantage that the target sequence need not be labeled with fluorescent dyes, as is the case with oligonucleotide microarrays in a separate reaction step, which is performed before or after the hybridization event. However, if a preamplification step is needed outside of the microarray, it results in increased labor and a risk of contamination. Immobilized molecular beacons or TaqMan probes typically have at least three modifications (group for immobilization, fluorescence donor and fluorescence acceptor), so high subsequent costs for production and immobilization of new probes occur immediately when there are any changes in the target sequence or in the array layout.

In addition, a so-called "Invader Assay" developed by the company Hologic (formerly Third Wave Technology) has been described in the prior art. This assay can detect the presence of a target sequence under isothermal conditions. In the simplest case this method requires a structure-specific nuclease, two target sequence-specific oligonucleotides—an invader oligonucleotide and a probe which has a fluorescence donor and a fluorescence acceptor. During the detection reaction, the two oligonucleotides hybridize on a strand of the target sequence, so that the 3' terminus of the invader oligonucleotide and the 5' terminus of the probe overlap and form a triplex structure (ternary complex). The triplex structure thus formed is the substrate for a structure-specific nuclease, which cleaves the probe (primary reaction) and thereby restores a previously suppressed fluorescence signal. In another embodiment of the Invader Assay, the probe does not have any fluorescence modifications, but the 5' region of the probe that is released can activate a subsequent detection reaction (secondary reaction) by interacting with a FRET detection molecule and form a local triplex structure. After cleavage of this complex, a fluorescence signal is obtained. In the reaction that is described, signal amplification does take place but there is no target sequence amplification. This "Invader Assay" can also be used for detection of single nucleotide polymorphisms (SNP).

The InPlex® system derived from the "Invader Assay" combines a preamplification of the target sequences with the Invader® Assay, in which the target sequences are first amplified by PCR and then transferred to a reaction cartridge and incubated for several hours (detection reaction). The InvaderPlus® reaction combines a PCR with the Invader reaction in one reaction vessel using a polymerase from *Thermus aquaticus* and the enzyme Cleavase®. First, the target sequence is amplified by PCR and then the polymerase is inactivated at 99° C. In the next step, the reaction mix is cooled to a temperature at which an Invader oligonucleotide and a probe are added onto the target sequence. This structure is recognized by Cleavase®, whereupon a cleavage reaction may take place with signal generation. This end point reaction typically lasts 2 hours. One disadvantage is that a large number of target molecules must be present for this to be detectable. It is impossible to perform the detection method and amplification in parallel. The sensitivity of these assays is therefore inadequate for investigating many questions.

Several solid-phase-based approaches are known in the prior art, in which the target sequence-specific probe is immobilized on a suitable surface with local resolution and can be used for detection of SNPs in genomic DNA. The detection is performed directly by way of the change in fluorescence and/or indirectly after successful ligation of a cleavage product with a primer and universal rolling circle amplification as well as labeling with a sequence-nonspecific fluorescent dye and/or biotin-labeled oligonucleotide and then incubation with streptavidine-coated gold particles. Since no target sequence amplification takes place in this isothermal process, the typical incubation time for one analysis is up to 24 hours, followed by a fluorescence measurement.

Microarray analyses comprise multiple steps, typically selection of the sequence of the immobilized capture molecule, sample preparation and amplification, hybridization and/or incubation followed by subsequent washing steps as well as signal measurement and data processing. The microarrays described in the prior art so far are based on the principle of direct interaction between the target molecule and immobilized capture molecule, so a modified capture molecule must be used as soon as a different target molecule is to be detected. In principle, this requires the synthesis of a modified array and is a significant time and cost factor. Because of the complex reduction process, a sequence layout will be produced in larger numbers for economic reasons. Working with microarrays thus offers less flexibility with respect to the target molecule to be detected because a modified sequence layout entails high subsequent costs and processing effort. Furthermore, universal microarrays have been disclosed in the prior art. Universal nucleic acid microarrays in which the sequence of the immobilized capture molecules is independent of the target sequence are available commercially as affymetrix "GeneChip Universal Tag arrays," for example. These methods are based on a universal microarray sequence layout, in which the immobilized oligonucleotides (ZIP code and/or Universal Tag) are independent of the sequence to be detected and do not interfere with it. In a typical detection reaction, the target sequence is usually amplified in a separate reaction vessel and optionally purified. Then there is a ligation step in which a specific detection probe and a fluorescence probe are hybridized directly side by side on the base sequence of the target sequence in the presence of the target sequence. The detection probe has a target sequence-nonspecific overhang (complementary ZIP code, cZIP code), which serves as the addressing sequence and is complementary to a ZIP code probe of the microarray. Ligation yields a product of the detection probe and the fluorescence probe, which is used for hybridization on a ZIP code microarray. A fluorescence signal at a certain specific ZIP code spot is an indirect indication of the presence of the target sequence in the reaction mix. Coded microbeads (beads) may also be used as the solid phase. Then an unambiguously identifiable bead is assigned to each capture molecule, this being achieved by a defined nucleotide sequence or staining and/or intensity. Due to this allocation, in a subsequent step and automated detection of the bead and parallel analysis may be performed. This method has the advantage that the beads are present in homogenized form in the liquid phase and the resulting reaction kinetics are higher than with comparable liquid/solid phase interactions.

A method titled "cDNA-Mediated Annealing, Selection, Extension and Ligation" (DASL) has also been described for expression analysis by means of universal microarrays in the prior art. First RNA is rewritten by means of biotin-labeled oligo-d(T)18 and primer molecules with a random sequence are transcribed into cDNA. Next, there is a hybridization step between two locus-specific oligonucleotides, where both oligonucleotides have universal locus-nonspecific sequence overhangs. The 3'-terminal oligonucleotide has an addressing sequence, which is integrated between the sequence-specific region and the nonspecific sequence overhang. The addressing sequence is complementary to a defined sequence on the universal microarray. In an elongation reaction, the region between the oligonucleotides is supplemented in a complementary fashion and ligated in the next step. Using special oligonucleotides, the ligation product can then be replicated by PCR, with the amplified ligation product being labeled by fluorescence-labeled primers. In the next step, hybridization is performed on a universal array and/or bead. The DASL process offers the advantage in comparison with the universal microarray described above that there are more possibilities for sequence selection of the oligonucleotides to be ligated because an elongation reaction supplements the missing nucleotides. However, through this reaction another step that is susceptible to errors is integrated into the process. These are very time-intensive methods because of the numerous processing steps and analysis steps, and there is also risk of contamination because amplified nucleic acid fragments must be transferred between reaction vessels. Furthermore, this method is designed only for endpoint measurements.

U.S. Pat. No. 5,653,939 and U.S. Pat. No. 6,099,803 describe methods which permit electrophoretic transport of charged (bio) molecules to defined microlocations (spots) on a microelectronic chip by local manipulation of an electric field. This "active microelectronic array" which was commercialized under the brand name NanoChip® consists of an ordered structure of individually addressable electrodes. By applying a voltage to one or more electrodes, charged analytes can be moved specifically to defined spots on the semiconductor chip and concentrated there. If the spots are provided with complementary capture molecules or those having an affinity, then a hybridization or affinity event may take place within a short period of time through electrophoretic transport. Since the polarity and applied voltage of the electrodes can be changed at will, this method permits manipulation of particles with a negative net charge (for example, nucleic acids, some proteins) and particles with a positive net charge (for example, some proteins). A multiplex analysis can be performed with an applied sample by occupation of multiple spots with various capture molecules. Then by reversing the polarity of the electrodes, repulsion of the target molecules from the capture molecule is induced, and the intensity of the interaction (selectivity) is determined and nonspecific bonds are minimized (electric stringence). The capture molecules are typically immobilized by means of biotin modifications which selectively bind to the streptavidine-modified polymer gel of the chip surface. The nanochip device platform is suitable in principle for DNA hybridization, SNP or STR analyses as well as cell type determinations and on-chip SDA reactions. Detection can be performed by passive hybridization of labeled probes or by conventional antibody techniques. Due to the applied voltage, electrolysis products ($H^+$, $OH^-$, $H_2$, $O_2$ and free radicals), which can damage the target molecule, are formed in the region of the electrodes. To minimize this effect, it is necessary to apply a separating intermediate layer in the form of a polymer gel. Since this platform is capable only of detecting molecular interactions, the sample material must usually be enriched in an upstream step. This is necessary in particular for nucleic acids, which are typically amplified by means of asymmetrical PCR. The device platform consists of a system and a microchip control unit which regulate, for example, the control of the applied voltage and the fluidics.

Another universal approach for detection of target molecules has been marketed by High-Throughput Genomics (HTG) (e.g., US 2001/0034025 A1 or U.S. Pat. No. 6,238,869 B1). The basis for this approach is a universal array of various anchor oligonucleotides which are immobilized at the 3' terminus on a solid phase (microtiter plate). Linker molecules which have a 5' segment that is complementary to the anchor oligonucleotides described above and also have a target molecule-specific 3' segment, alter the binding specificity after hybridization in this array position. If nucleic acids are detected with the newly configured array, the linker molecule consists of an oligonucleotide; for detection of protein, the molecule typically consists of an oligonucleotide-antibody conjugate. One embodiment proposed by HTG for detection of mRNA for expression analyses permits parallel detection of 16 different loci per cavity on a commercial microtiter plate. To do so, for example, cells are lysed and denatured in a separate vessel in the presence of mRNA-complementary DNA probes. After successful hybridization, single-stranded nucleic acids (mRNA and excess of DNA probes) are digested by adding an S1 nuclease. The RNA portion of the duplex is degraded by alkaline hydrolysis, so that stoichiometric amounts of DNA probes are present in the batch after neutralization. Then the batch is transferred to the array, whereupon sequential hybridizations are performed with a detection probe, which is partially complementary to the DNA probe, and a complementary detection conjugate, which is provided with a peroxidase modification. After adding suitable substrates, a local chemiluminescence signal occurs in the position of the array where the hybridization complex described above has been successfully formed. This method is labor-intensive because of the numerous processing steps. Another disadvantage is the low sensitivity of the assay because no amplification reaction is integrated into the assay protocol. Thus, for example, very low nucleic acid concentrations cannot be detected with sufficient sensitivity. Furthermore, the additional hybridization steps may lead to interference and thus to unwanted nonspecific reactions or false-positive signals.

Methods for detection of protein by means of nucleic acid-based methods have been disclosed in the prior art. In these methods the analyte interacts with an immobilized protein (for example, an antibody) and is then incubated with a protein nucleic acid conjugate. In a subsequent washing step, nonbound molecules are removed. The conjugate contains a nucleotide sequence which is complementary to a circular DNA molecule which is then added. By processing with a suitable polymerase, the primer is elongated and generated by means of RCA concatemers of the DNA molecule. After incubation with gold-modified probes or sequence-nonspecific fluorescent dyes, the regions of a microarray having a capture molecule and detection conjugate bound to the analyte are labeled specifically. By means of suitable detection methods, binding results of the analyte can thus be detected with local resolution. One disadvantage here is that these methods use two different proteins and/or protein-nucleic acid conjugates, which correlate directly with the respective analyte. The use of proteins and the methods derived therefrom constitute a major cost factor because of the synthesis. The company Chimera Biotec has pursued an approach that is similar in principle with the Imperacer® technology which they developed; technology uses antibody-DNA chimeras, i.e., synthetic DNA fragments to which an antibody has been coupled. If this antibody binds to the proper antigen, the coupled DNA fragment can be amplified by means of real-time PCR and detected after subsequent washing steps.

In central laboratories, medical diagnostic tests are performed with the help of automatic analyzers and include fields of clinical chemistry, medical microbiology and medical immunobiology as well as transfusion medicine. In addition to these high-throughput systems, there are definitely smaller systems that permit a point-of-care multianalyte analysis of important blood values or marker proteins, for example. These utilize various principles of detection such as absorption measurement of a chromogenic reaction of the sample with reagents already present in the reaction cartridge (e.g., Abaxis Piccolo® Xpress), flow-through immunoassay by means of an antibody-labeled membrane and then labeling of the analyte with gold-modified detection antibodies (e.g., Axis Shield Afinion) or a linear test strip (e.g., Abbott Point-of-Care i-STAT®, Roche Cobas h232, BioSite® Triage® system). In these methods, the test liquid is applied in a special reaction cartridge in which an absorbent material absorbs the sample by capillary forces, transports it and optionally separates it. The test kits available on the market are typically based on immunofluorescence technology. In defined zones, reagents have already been applied to the material (detection antibodies) and/or immobilized there (capture antibodies). The procedure typically does not require any sample preparation, so that tests can be performed with whole blood, blood plasma or urine (optionally with an internal filter for blood cells and particles) and in most cases they detect several analytes within one reaction. The results are available in about 15 minutes. The test kits on the market now include markers for heart diseases, pathogens as well as metabolites of various medications. The advantages of the embodiments described here consist of the high user friendliness (simple procedure protocol, no sample preparation) and short processing time. The disadvantage is that these devices, which are used mainly in clinical diagnostic tests, are compatible only with proprietary consumable materials and their use is limited to clinically relevant markers and parameters (for example, cardiovascular diseases). Furthermore, their use is greatly limited by the manufacturer because detection reactions can be performed only for certain target molecules for which the manufacturer has released test kits.

The test strip principle described above is also used in nucleic acid analysis, where the nucleic acid to be detected is amplified and applied to a test strip on which there are target sequence-specific capture molecules and detection molecules. Through capillary forces, the target sequence passes through various zones on the test strip and interacts with the various complementary molecules or affine molecules. By determining a detection band (for example, by means of gold-labeled detection molecules) at a defined location on the test strip, the presence of the target sequence in the sample solution to be analyzed can be determined. A universal approach for detection of any nucleic acid sequences is described in the prior art (e.g., Baeumner, A. J. et al., 2004, A universal nucleic acid sequence biosensor with nanomolar detection limits, Anal. Chem., 76, 888-894). The sample solution is amplified here and incubated with bifunctional reporter probes. One section of the probe hybridizes at the target sequence, whereas another section of the probe hybridizes on vesicles with immobilized oligonucleotides of a complementary sequence. Another section of the amplified target sequence binds to a biotin-modified oligonucleotide. After applying the test strip to the solution, there is a directional transport of the hybridization complex which can be accumulated in a streptavidine-modified zone and detected. Nucleic acid analysis based on test strips requires an upstream amplification step and the associated handling of post-PCR products. In addition, the systems are limited by low multiparameter level, low sensitivity and restricted quantification.

In various fields of clinical analysis and in vitro diagnostic tests, multianalyte detection methods are extremely important, so a few examples are given below (although this is not limited to these examples): for example, for determination of blood group, not only is ABO genotyping relevant but it is also important to create the human neutrophilic antigen (HNA) profile, which must be determined for blood transfusions and tissue transfusions. Parallel testing of blood donor samples for HIV variants and hepatitis B and/or C viruses is performed routinely with immunoassays or nucleic acid-based techniques. Specific detection of pathogens requires the determination of several genomic loci to permit a diagnosis derived from this after short analysis times.

Determining the activity of various marker genes and control genes allows the creation of an express profile. This may be used, for example, to identify oncogenes, which influence cell division and differentiation and therefore are closely associated with cancer or to make predictions about the efficacy of certain drugs, depending on the patient's genotype (personalized medicine). Hereditary diseases, which occur frequently, can be detected by molecular biological (prenatal) diagnostic testing; these include, among others, cystic fibrosis (mucoviscidosis), phenylketonuria (metabolic disorder) and thalassemia (degradation of erythrocytes). In addition, the joint detection of inflammation markers such as procalcitonin or cytokines make it possible to infer the severity of an infection.

Numerous diagnostic questions require the analysis of multiple target molecules, genetic loci or other markers as well as internal controls and/or references, so that methods which allow only the determination of a single parameter per analysis are usually less relevant. If various individual analyses are performed in parallel for detection of multiple parameters, this is uneconomical on the other hand: the sample solution must be divided into several homogeneous reaction batches in which different target molecules are detected. One disadvantage here is that due to the division of the sample solutions into "n" aliquots, the quantity of substance in the individual reaction is reduced by a factor of 1/n, which reduces the sensitivity of the detection reaction accordingly.

Another disadvantage is that the analysis of samples with a low nucleic acid concentration or protein concentration is impossible without an analyte-dependent prior concentration step and/or amplification step because of the low sensitivity of many detection methods. In the parallel microarray-based analysis of low concentration nucleic acids, preamplification constitutes an additional step, on the one hand, and also entails the problem that homogeneous amplification cannot take place, depending on the initial quantity of substance and the reaction efficiency, while quantitative results are possible only to a limited extent. Another disadvantage is the need to transfer amplified products between different reaction vessels and devices because not only is this associated with an additional step but also it entails the risk of contamination.

Microarray analyses are based on direct interaction between an immobilized capture molecule (binder partner or probe), typically with local resolution, on a planar substrate and a target molecule, which is present freely and diffusively in the liquid phase. One disadvantage of this method is that it includes several steps: an upstream amplification and/or enrichment, labeling of the target molecules to detect the interaction of the target molecules with the capture molecule as well as several hybridization and washing steps. In addition, another problem with the direct dependence between the capture molecule and the target molecule as described here is that the immobilization of another probe is necessary when a new experimental question arises, for example, when a different genotype of a virus is to be detected.

Another disadvantage is that, because of the complex production process and the high setup costs (configuration of the array, purification of the processing elements), it is economical to produce a sequence layout only if large numbers are produced (scale effects). This limited flexibility reduces the advantage of the highly parallel and automatable processing. Detection with universal nucleic acid microarrays whose probes are independent of the target molecule to be detected can overcome this disadvantage but the labor involved with these methods is high so that they have not become successful. In addition to the technical disadvantages of the universal microarrays described here, so far no biochemical system has become known from the prior art, which allows combined multiplex analyses in various substance classes, such as nucleic acids and proteins, so that various methods or items of equipment must be used for different types of detection.

US 20020110826 relates to the use of solid-phase hairpin oligonucleotides. An enzymatic reaction, which leads to the splitting off of the portion complementary to the target sequence, is facilitated by a hybridization reaction of a target sequence on a hairpin oligonucleotide. A label can therefore bind to the hairpin oligonucleotide. One disadvantage is that the target sequence must diffuse to the solid phase hairpin oligonucleotide. The diffusion rate here is slower due to the size of the target sequence.

The object of the invention was thus to provide a system, a means or a method that would permit detection of biomolecules, so that it can be used universally and does not have the disadvantages or shortcomings of the prior art.

DESCRIPTION

This object is achieved by the independent claims. Advantageous embodiments are derived from the dependent claims.

In a first embodiment the invention relates to a mediator probe for detection of at least one target molecule comprising a probe region and a mediator region, characterized in that the mediator probe is an oligonucleotide and the probe region is situated on the 3' terminus and the mediator region is situated on the 5' terminus of the oligonucleotide, a chemical, biological and/or physical cleavage spot being present between the regions, and the probe region having an affinity for a template molecule and the mediator region having a further affinity for a detection molecule and wherein the mediator probe is cleaved at the cleavage site during an amplification process of the template molecule and wherein an interaction of the cleaved mediator region with the detection molecules triggers a detectable signal.

It was completely surprising that a mediator probe could be made available for detection on a target molecule and/or a detection molecule without the disadvantages or shortcomings of the probes or systems disclosed in the prior art. It is advantageous in particular that the presence of the released mediator region triggers a detection reaction. The coupling between the presence of a target molecule and the detection reaction depends only on the properties of the mediator region and/or the mediator probe and thus allows free coupling between any target molecule and any detection reaction and/or detection molecule.

The mediator probe thus characterizes in particular a molecule having at least two functional regions, which may interact with the target molecule, and/or the template molecule and/or the detection molecule. The mediator probe advantageously triggers a detection reaction in the presence of a target molecule—optionally involving an interaction with auxiliary molecules.

The probe region is preferably complementary to a segment of the template molecule and/or the target molecule. The probe region of the mediator probe binds to a template molecule, which is amplified. The binding takes place only with the probe region of the mediator probe because it has an affinity for the template molecule. The mediator region does not have any affinity for the template molecule and also does not have a complementary sequence segment. Therefore, this portion of the mediator probe does not bind to the template molecule, so that a flap structure is formed. During the amplification reaction, the mediator probe is cleaved at the cleavage sites, so that the mediator region is released. The mediator region is free. The mediator region preferably has a region complementary to a segment of a detection molecule. The mediator region binds to a detection molecule, so that a detectable signal is triggered. Inferences about the presence of the template molecule can be drawn from the detectable signal. The template molecule itself may be the target molecule to be detected or it may be associated with it, so that information about the presence of the target molecule can be generated via the template molecule.

By splitting off the mediator probe, a mediator molecule is released, having no interaction partner except for the detection molecule. In comparison with conventional nucleic acid-based approaches, there is thus no need, as in the case of asymmetrical PCR or LATE PCR, to prevent a reannealing of the strand to be detected through additional optimization of the primer relationships. This greatly reduces the effort involved. Due to its length of typically 20 to 25 nucleotides, the mediator molecule has a higher diffusion constant than nucleic acid fragments which are generated by amplification mechanisms and are generated for a hybridization reaction, for example.

In the sense of the present invention, the term "detection molecule" or detection molecule characterizes in particular a molecule with which the mediator region can interact either directly or indirectly and can optionally trigger a detection reaction (for example, a change in a fluorescence signal) due to processing.

The term "amplification" denotes in particular a replication of a nucleic acid molecule.

An auxiliary molecule refers in particular to a molecule which contributes to a change in the state of the mediator probe in the presence of the target molecule and/or the template molecule. Various auxiliary molecules from one or more substance classes may be used, for example, enzymes (polymerases), nucleic acids (oligonucleotides). It is preferable for the probe region bond to the target molecule or the template molecule to be elongated enzymatically by an auxiliary molecule.

It is preferable for the mediator probe to have 1 to 70, preferably 15 to 60, especially preferably 35 to 45 nucleotides. Especially preferred results are achieved with these sizes because the mediator region can diffuse to the detection molecule at a high diffusion rate due to the small size after cleavage. The invention is therefore advantageous in comparison with embodiments from the prior art in which the target itself must arrive at a detection molecule.

It is also particularly advantageous that the mediator probe consists of an oligonucleotide, which can be synthesized inexpensively without any technically complex modifications, for example, fluorescence donors and/or acceptors.

It is preferable that the target molecule and/or the template molecule is a biomolecule selected from the group comprising DNA, RNA, protein, aptamer and/or a combination thereof. It may also be preferable that only parts of a molecule, for example, recognition sequences or epitopes are to be detected and thus are target molecules in the sense of the invention. The target molecule(s) is/are preferably in a sample solution. A combination of the target molecules may also be referred to as a mixture in the sense of the invention. Molecules of different substance classes (for example, protein and DNA or DNA and RNA) can be surprisingly be detected individually or in parallel in a batch so that a universally usable agent is available.

In the sense of the invention, an aptamer describes in particular an oligonucleotide which can interact with and/or bind to molecules from other substance classes (for example, proteins) because of their structural properties. An aptamer is preferably a single-stranded nucleic acid, which has a greater binding affinity for other molecules, for example, proteins. A preferred aptamer additionally has terminal regions "region i" and "region ii" which can interact with one another (referred to as a closed form in the sense of the invention). Two regions are differentiated from this, with "region iii" having affinity for the target molecule and "region iv" being a binding sequence for a primer molecule and a mediator probe. Region iv allows only binding of the primer and the mediator probe if region iii is interacting and/or associated with the target molecule.

It is preferable for the target molecule to be the template molecule at the same time. This embodiment is used, for example, when the target molecule is a DNA sequence. In this case, no additional template molecule is needed for the amplification reaction, so the target molecule itself is amplified.

If the target molecule itself cannot be amplified, it is advantageous that a template molecule is used for the amplification reaction, wherein the amplification reaction must allow inferences about the existence of the target molecule, so that the target molecule can be detected. This may be accomplished in various ways according to the invention. Thus it may be preferable that the template molecule is formed only due to the presence of the target molecule or that the template molecule interacts with the target molecule and therefore undergoes a change in structure.

For example, it is preferable if the target molecule is a protein and the respective template molecule is an aptamer. The aptamer has a binding site for the probe region. It is preferable here for the aptamer to bind to the protein and for the binding site to be accessible for the probe region only during this binding. This prevents the presence of the aptamer alone from being detected without allowing any inferences about the presence of the target molecule (protein) to be drawn. Only when the target molecule is present can the aptamer bind to it, and its binding site for the probe region is preferably accessible through a change in the secondary structure. The probe region of the mediator probe may then bind to the aptamer. By amplification of the aptamer, the mediator region is split off from the probe region and may thus bind to the detection molecule. Thus the protein can be detected by the presence of the aptamer.

If the target molecule to be detected is an RNA sequence, it is preferable for the template molecule to be the corresponding cDNA, which is preferably generated by a reverse transcriptase. The cDNA produced in this way is then the template molecule for the amplification. For the reverse transcription, it may be advantageous to use modified primers with a 5' sequence overhang. This embodiment is advantageous in particular when the original DNA is also present because this ensures that the mediator probe will bind only to the cDNA and was not also on the original DNA locus of the template for the RNA. Due to this embodiment, it is also possible to perform detections, which allow conclusions about gene expression of various genes, because DNA of the gene and the RNA transcribed from it (by way of the cDNA with primer overhang) can then be detected in parallel. Two different mediator probes are used in such a method, one of the two probe regions binding to a region comprising a portion of the primer overhang. This probe region can therefore bind only to the cDNA but not to the original DNA.

A complex of the aptamer and the associated target molecule or an interaction product of two or more substances classes such as, for example, nucleic acids and proteins, can also be used as the target molecule. Various target molecules can be detected individually or in parallel in one reaction batch. It is preferable for the mediator probe to consist of an oligonucleotide or a corresponding derivative, while the target molecule is a nucleic acid, a corresponding derivative or a molecule comprising DNA, RNA, protein, aptamer and/or a complex of aptamer and associated DNA, RNA or protein and for the detection molecule to be an oligonucleotide or a derivative thereof.

In another preferred embodiment, the invention relates to the mediator probe, wherein the probe region and the mediator region overlap functionally and/or spatially, preferably with a nucleotide.

It is preferable for the mediator probe to comprise another region in addition to the probe region and the mediator region. This region is preferably a lock region, which is complementary to or has affinity with the mediator region. The lock region is advantageously situated on the 3' end of the probe region. Then the three regions may overlap both functionally and spatially. A direct or indirect interaction of the probe region with the template molecule creates a change in the mediator region and/or the lock region and thus alters the affinity and/or the interaction between the mediator region and the lock region and/or the complete mediator probe. A mediator region comprising a lock region is advantageous because additional protection is created in this way, preventing the mediator region from binding to or annealing on the template molecule. Due to the fact that the mediator region and the lock region have an affinity for one another or are complementary to one another, the mediator probe may form a hairpin structure in the absence of the template molecule and/or the target molecules.

It is also preferable for the mediator probe to have a protective chemical group at its 3' end. This embodiment is advantageous because it prevents an enzymatically catalyzed sequence elongation of the uncleaved mediator probe from taking place. The protective chemical group may be selected from the group comprising a phosphate group, biotin, inverted nucleotide, nucleotides that are not complementary to the target sequence. Those skilled in the art are familiar with other protective chemical groups that can prevent elongation of an oligonucleotide, in particular of the 3' terminus.

It is preferable for the probe region and the mediator region to be freely combinable independently of one another. Thus, for example, a detection molecule may also correlate with other target molecules by linking the fitting mediator region with any probe region and synthesizing it. This achieves a particularly high flexibility in use of the mediator probe according to the invention.

In another preferred embodiment, the invention relates to a system comprising a mediator probe and a detection molecule, characterized in that the detection molecule is an oligonucleotide and has at least the following regions:
 a. a first region on a 5' terminus of the detection molecule, which has a fluorescence acceptor or a fluorescence donor and/or a chemical group for binding to a solid phase and/or a protective chemical group,
 b. a second region, which interacts with the mediator region and
 c. a third region, which has a fluorescence donor or a fluorescence acceptor and/or a protective chemical group.

It was completely surprising that a system could be made available that could be used universally and in particular would contribute toward a minimization of the contamination cases in microbiological detection methods. Various molecules can be detected by means of a biochemical reaction, preferably on a universal detection chip, using standardized detection molecules. This is made possible in particular by the fact that the direct physical interaction between the target molecule and the detection molecule is canceled. A mediator probe functions as a mediator (information carrier) between a target molecule and a detection molecule. The mediator probe (in the presence of additional auxiliary molecules) is preferably cleaved by interaction with the target molecule or the template molecule and releases an activated mediator molecule, which initiates a detection reaction.

The system according to the invention allows design of the detection molecule to be designed independently of the target molecule. Thus, by using a standardized set of detection molecules, it is possible to detect various target molecules in a sample, so that the reaction can be adapted inexpensively to the respective target molecule by adapting the mediator probe and by using suitable auxiliary molecules (for example, primers) or template molecules (for example, aptamers).

Due to this advantageous property, the problem of the typically direct correlation between the target molecule and the immobilized capture molecule, which has been described in the prior art, is solved.

The mediator region is advantageously diffusively present in the reaction solution after cleavage and can interact with region 2, the mediator hybridization sequence, of the detection molecule. The detection molecule may preferably be bound to a solid phase or may also be present freely in a solution.

These detection molecules to not interact physically with these target molecules. Coupling occurs between the target molecule and the detection molecule only indirectly by way of the corresponding mediator probes. A target molecule can be assigned freely to any detection molecule by using the mediator probe.

If the detection molecules are immobilized on a solid phase, a universal microarray or detection array can be made available. The universal microarrays thereby produced can be stored for a long period of time under defined storage conditions, which is a definite advantage in particular in comparison with protein arrays from the prior art. Therefore, storage independently of planned experiments is not critical.

The present invention thus makes available, for the first time, a standardized microarray which is independent of the target molecule and can be used for various multianalyte analyses, because the specific liquid-phase reaction can be adapted quickly and inexpensively to the target molecule.

Therefore, various experiments with a reaction cartridge without preprocessing steps and/or post-processing steps can be performed by producing a standardized microarray, which is thus a cost-saving advantage, and the cartridge can be produced in large numbers (scale effects). It is thus possible to perform detection reactions (for example, in the area of routine analyses) with one batch of the standardized reaction cartridge.

A microarray preferably refers to a locally resolved at least one-dimensionally array of immobilized capture molecules on a suitable solid phase (typically planar). Alternative methods permit a solid phase-supported approach using beads which allow an unambiguous discrimination due to different colorations, for example. A certain capture molecule can be immobilized on a defined class of bead.

A bead preferably refers to microbeads having a diameter of 5-100 µm in particular. These may optionally be present on the surface and/or in the interior in modified and/or functionalized form. The use of beads makes it possible to make available large surface areas in a defined reaction volume.

Due to a suitable auxiliary molecule, for example, an enzyme, in particular a polymerase, the mediator region is elongated, wherein region 1 of the detection molecule is degraded sequentially. The detection molecule is preferably altered by splitting off the 5' terminus and the associated fluorescence acceptor Q and the previously suppressed fluorescence signal of the fluorescence donor F is restored. If the interaction of region 1 and region 3 is suppressed by splitting off this end, then the structure of the secondary structure is eliminated. In this case, the mediator molecule may be elongated in a complementary fashion by the auxiliary molecule described above under certain conditions up to the newly formed 5' terminus of the detection molecule. Due to this elongation, the elongated mediator molecule has a sequence segment that is complementary to region 1 and region 2 of the detection molecule.

The system according to the invention allows the detection of various target molecules in a closed reaction vessel, which can be discarded without any risk of contamination after processing. This constitutes a substantial advantage in comparison with the prior art.

In addition, it is advantageous that the detection molecule
d. has a fourth region on a 3' terminus of the detection molecule, wherein the fourth region comprises a chemical group for binding to a solid phase and/or a protective chemical group.

This variant is advantageous because the detection molecule can be immobilized in this way and a microarray can be produced, for example. Possible chemical groups for immobilization of an oligonucleotide are listed as example. The chemical group depends on the surface chemistry used and any coupling molecules that might be needed: OH (hydroxyl), $NH_2$ (amino), Ph (phosphate), acrydite or silane. Those skilled in the art are familiar with methods for immobilizing oligonucleotides on a surface. In particular to permit a putative immobilization of the 5' terminus, the detection molecule has a chemical group and/or a protective chemical group.

It is preferable for the hairpin structure to be designed by complementary hybridization of the 5' terminus of the detection molecule with an internal sequence segment and the 3' terminus of the detection molecule comprises an unpaired sequence segment. After adding the mediator region onto a sequence region of the unpaired 3' sequence segment, the mediator region is preferably elongated by a polymerase, wherein nucleotides of the 5' terminus of the hairpin structure of the detection molecule are removed, based on the nuclease activity of the polymerase. After forming this structure, the fluorescence donor F and the fluorescence acceptor Q interact with one another, suppressing the fluorescence signal of F (fluorescence-resonance energy transfer, FRET).

It is preferable for the mediator probe and/or the detection molecule to have fluorescence-labeled nucleotides. It is preferable in particular for the detection molecule to have at least one fluorescence modification on the 5' terminus and/or within the hairpin structure. The detection molecule has one or more fluorescence modifications that are capable of a fluorescence-resonance energy transfer and can be separated from one another spatially after the cleavage, thus permitting detection of a change in the fluorescence signal.

Sequence-specific or sequence-nonspecific fluorogenic and/or chromogenic probes or fluorescent dyes may interact advantageously with at least one region of the mediator probe and/or the detection molecule. In addition, it may be advantageous if the detection molecule has at least one fluorescence modification on the 5' terminal region and/or with in the hairpin structure and if the fluorescence modifications are split off from the detection molecule after the reaction with the mediator region by means of an auxiliary molecule and/or if the 5' terminus of the hairpin structure of the detection molecule is removed and a change in the fluorescence signal is detected on the detection molecule.

It is preferable that the detection molecule is altered as a result of a direct or indirect interaction with the mediator region, comprising a change in the secondary structure, a change in fluorescence, phosphorescence, mass, absorption, light scatter, electrical conductivity, enzymatic activity and/or affinity.

There is a change in the detection molecule due to a direct or indirect interaction of the mediator region with the second region of the detection molecule and this change can preferably be measured either physically or chemically.

It has also proven to be advantageous that the mediator region bound to the second region of the detection molecule is enzymatically elongated by at least one auxiliary molecule, such that the auxiliary molecule preferably binds to the 3' terminus of the bound mediator region.

The auxiliary molecule is selected from the group comprising catalysts, proteins, nucleic acids, natural substances, enzymes, enzyme systems, cell lysates, cell constituents, derivatives derived from cell constituents and/or synthetic molecules.

It is also preferable that the auxiliary molecule is a molecule from a nucleic acid amplification system and/or a restriction enzyme system.

In a preferred embodiment, the detection molecule may also have one or more fluorescence modifications on the 5' terminal region and/or within the hairpin structure, such that after the processing of the hybridized mediator region with the help of a suitable enzyme, the 5' terminal nucleotides are split off from this detection molecule with the help of a suitable enzyme and a change in the fluorescence signal can be detected on the detection molecule. The mediator molecule thus released preferably interacts with at least one detection molecule complex, which is present freely in the solution or is immobilized on a solid phase. The detection molecule complex may have one or more different or similar chemical modifications and may generate a detectable signal after interaction with the mediator region. It is preferable that a physically or chemically measurable change in the detection molecule will occur through a direct or indirect interaction of the mediator region with the second region of the detection molecule. This region can trigger a signal only after the mediator probe has been split off. The mediator region of the mediator probe preferably does not trigger a signal either directly (for example, through hybridization) or indirectly (for example, through processing by polymerase) since it is still associated with the mediator probe, because otherwise this would be a case of a signal occurring independently of the target molecule. This measurable change may also emanate from the auxiliary molecules (e.g., polymerase).

In a direct detection reaction of the mediator region, the latter directly alters the detection molecule. In an indirect detection reaction, the mediator region induces the change in the detection molecule by interaction with auxiliary detection molecules, in particular a polymerase, which elongates the mediator region. The mediator region advantageously causes a change in the detection molecule during the detection reaction and itself undergoes a change due to suitable auxiliary detection molecules. This embodiment is advantageous because it permits a clear-cut differentiation between a mediator molecule altered in the detection reaction and a mediator molecule derived directly from a mediator-probe cleavage.

An auxiliary detection molecule describes in particular a molecule, which advantageously interacts with the mediator region and the detection molecule, such that a detection reaction is preferably triggered. Various auxiliary detection molecules from one or various substance classes may be used.

The auxiliary detection molecules are preferably selected from various substance classes such as catalyst, proteins, nucleic acids, natural substances, enzymes, enzyme systems, cell lysates, cell constituents, derivatives derived therefrom or synthetic molecules or a mixture of various molecules of these substance classes.

Furthermore, it is preferable for the auxiliary detection molecule to split in a structurally specific manner. It is preferable for the auxiliary molecules to comprise molecules from a nucleic acid amplification system and/or a restriction enzyme system. The probe region of the mediator probe may preferably interact with the target molecule and/or the template molecule through base pairing, and an auxiliary molecule may cleave the mediator probe, wherein the mediator region interacts with a detection molecule through base pairing and an auxiliary detection molecule splits off components of the detection molecule. This cleavage reaction serves as indirect protection for the target molecule. The component of the detection molecule that is split off may preferably be a fluorescence donor or a fluorescence acceptor.

However, it may also be preferable for the auxiliary detection molecule to perform sequence-specific cleavage in which the auxiliary molecule is a nucleic acid amplification system and the auxiliary detection molecule is a restriction enzyme system or a mixture of a nucleic acid amplification system and a restriction enzyme system. The detection molecule is an oligonucleotide or a derivative and contains the corresponding recognition sequence for the restriction enzyme system, wherein the mediator region on the detection molecule binds to the complementary section and is elongated by the nucleic acid amplification system. The sequence duplex thereby generated thus contains at least one recognition sequence pattern of the restriction enzyme system which splits it into at least two parts. After cleavage of the sequence duplex, a signal can preferably be detected, for example, a change in fluorescence or in mass. However, it may also be advantageous if, after splitting of the sequence duplex, at least one cleavage fragment can initiate an amplification reaction with complementary or partially complementary nucleic acid sequences that are present, wherein said nucleic acid sequences may be present freely in solution or may be immobilized on a solid phase.

In a preferred embodiment, amplification may be detected by incorporation of fluorescence probes or otherwise labeled nucleotides or by addition of sequence-specific, fluorogenic or chromogenic probes or by addition of a sequence-non-specific fluorescent dye. The amplification products may advantageously be detected directly or indirectly, where detection provides indirect evidence of the target molecule.

The mediator region thereby released may preferably initiate an enzymatically catalyzed amplification reaction or polymerization reaction, preferably in the presence of a suitable nucleic acid through one or more different enzymes, for example, polymerases. The suitable nucleic acid may be present in single-stranded or double-stranded form and a reverse primer may additionally be used in the detection reaction.

It is preferable for the detection molecule to be bound to a solid phase or to be present freely in a solution.

Furthermore, it is advantageous that the detection molecule is a single-stranded nucleic acid molecule or nucleic acid derivative, preferably having a hairpin structure. It is advantageous here for the hairpin structure to be designed so that the 5' terminus of the detection molecule hybridizes with an internal sequence segment in a complementary fashion and the 3' terminus of the detection molecule comprises an unpaired sequence segment.

The detection molecule preferably has one or more similar or different modifications (for example, abasic nucleotides and/or phosphotioates and/or functional groups such as fluorescent dyes). There is advantageously a change in the detection molecule through direct or indirect interaction with the mediator and it may involve one or more changes in the fluorescence, phosphorescence, mass, absorption, light scattering, electric conductivity, enzymatic activity or affinity, so that the change can be detected physically. In the presence of the mediator, the detection molecule may preferably undergo a chemical modification such as, for example, phosphorylation, dephosphorylation, amidation, binding or cleavage of a chemical group, or a change in fluorescence, phosphorescence or luminescence.

In the sense of the invention, an abasic nucleotide describes in particular a DNA building block in which the deoxyribose is not linked to a base and therefore is just a phosphate-sugar backbone. In DNA duplexes there is no formation of a hydrogen bridge bond in this position. This modification can be synthesized by using tetrahydrofuran (THF).

It is also preferable for the detection molecule to contain at least one fluorescence modification on the 5' terminus and/or within the hairpin structure.

In another preferred embodiment the invention relates to a method for detection of at least one target molecule comprising a mediator probe according to the invention and/or a system according to the invention, including the following steps:

e. Binding the probe region of the mediator probe to a sequence of the template molecule and/or the target molecule,
f. Amplification of the template molecule and/or the target molecule,
g. Splitting off the mediator probe at the cleavage site by at least one auxiliary molecule and
h. Binding of the cleaved mediator region of the mediator probe to the detection molecule.

It is preferable for splitting off the mediator probe to induce a change in the physical and/or chemical properties of at least one region of the mediator probe, selected from the group comprising molecular weight, enzymatic activity, binding properties including affinity or avidity, chemical reactivity, the presence of chemical groups, electrical properties, including conductivity, polarizability or charge, and/or optical properties, including absorption and emission of light.

In a particularly advantageous embodiment, a nucleic acid-based amplification of the target molecule can directly amplify a template molecule (for example, an aptamer), which thus increases the sensitivity. The amplification and detection reactions may be combined and conducted in parallel. This clearly differentiates the present invention from the Invader® reaction, which is described in the prior art and in which the detection is performed with linear signal amplification and/or consecutive amplification and detection.

The interaction of the target molecule and/or the template molecule with the mediator probe preferably results in the mediator probe being split off directly or indirectly, so that these fragments are preferably created:
  a fragment of the mediator region and a fragment of the probe region or
  the mediator region and a fragment of the probe region or
  the mediator region and a portion of the probe region as a and a fragment of the probe region or
  a fragment of the mediator region, the lock region and/or a fragment of the lock region and a fragment of the probe region or
  the mediator region and the lock region and/or a fragment from the lock region and a fragment from the probe region or
  the mediator region and a portion of the probe region as a contiguous fragment as well as the lock region and/or a fragment of the lock region and a fragment of the probe region.

It is especially preferable for the cleaved mediator or a fragment containing a portion of the mediator region to bind the second region of the detection molecule.

The mediator molecule is detected with the help of a detection reaction. The reaction mechanism may take place in parallel with the described amplification of the target molecule and/or the template molecule.

The method according to the invention is advantageous because a novel liquid-phase reaction has been developed which decouples the dependence of the target molecule and the detection molecule and is capable of detecting almost any target molecule when used in conjunction with a standardized microarray. Parallel detection of various target molecules is made possible through the combination of the novel liquid-phase reaction and a universal microarray.

It is preferable for the amplification of the template molecule and/or the target molecule to be performed by PCR, preferably by real-time PCR.

PCR denotes the polymerase chain reaction in particular, i.e., a method in which a nucleic acid segment bordered by primer molecules is amplified exponentially. The reaction batch is heated and cooled cyclically.

A primer preferably describes an oligonucleotide which is typically complementary to a segment of the nucleic acid to be amplified and borders this segment. Two primers which define an amplicon are typically referred to as the forward primer and the reverse primer. Since polymerization is performed from the 5' terminus in the direction of the 3' terminus, a trimer needs a 3'-OH terminus to which the polymerase covalently links the other nucleotides.

It is preferable in particular to use the mediator probe in the sense of the invention during a real-time PCR. Most of the established techniques of monitoring real-time PCR make use of individual target-specific fluorogenic probes. This drives up the cost of the synthesis, which is a major disadvantage of these systems. Therefore there has been interest for a long time in a universal method that can be used for monitoring amplification reactions, which will combine sequence specificity and low cost. The invention has been able to solve this problem with the mediator probe according to the invention, which can preferably be used during an amplification reaction, in particular preferably a real-time PCR. In this use, the target molecule is a DNA nucleic acid, amplified with ordinary oligonucleotide primers and a polymerase. Sequence-specific detection, preferably real-time detection, is implemented by the bifunctional mediator probe according to the invention, which is cleaved during amplification after interaction with the target sequence. The cleavage is catalyzed by the polymerase. The mediator region is preferably designed so that this is not complementary with the target sequence. The mediator region then diffuses to a detection molecule, which is either immobilized or is present in solution. The detection molecule is a closed unit and is independent of the target. The detection molecule can therefore be used universally and is not bound to a specific target. This greatly reduces the cost of this type of detection because the detection molecule need not be tailored to each reaction and each target molecule.

The detection molecule preferably has a hairpin structure and contains a fluorophore and a quencher, preferably arranged in spatial proximity to one another. Particularly efficient detection with FRET is made possible by this arrangement. At the unpaired 3' end, the detection molecule also contains a mediator hybridization site that is complementary to the mediator region.

FRET preferably refers to a florescence-resonance energy transfer, in particular energy transfer from a donor molecule to an acceptor molecule.

During real-time PCR, target amplification and detection take place simultaneously in a coordinated reaction. During the denaturing step of the DNA templates, they are divided into two single strands. While they are cooling down to reach the annealing temperature, both the primers and the probe region of the mediator probe undergo hybridization. The 5' region (the mediator region) does not bind to the target DNA. Therefore a flap structure is formed. During the elongation of the primer, the mediator region is drawn into the nuclease domains of the polymerase and thereby cleaved. The cleaved region (the mediator region) then has a 3'-OH group. The probe region is then degraded during the elongation of the primers. In any duplication of a target, a mediator region is thereby released. The mediator regions diffuse to the detection molecule hybridize with their mediator hybridization site. It is preferable for the polymerase to elongate the 3' end of the mediator region, which leads to fluorescent dequenching. Two different signal paths are preferred here. The 5' terminus of the detection molecule is degraded by the 5'-nuclease activity of the polymerase, and the quencher radical is split off. However, it is also preferable for the polymerase to destabilize the parent duplex of the detection molecule and for the hairpin structure to be unfolded without degrading the 5' terminus. Both paths ultimately lead to dequenching of the fluorophore. The two paths can take place in parallel because Taq polymerase, for example, is known for different exonuclease activities. One advantage of the present invention is that the fluorescence emission accumulates successively with each amplification cycle, so detection can be successful even with particularly small starting amounts of target molecules.

Real-time PCR using the mediator probe as a detection means is advantageous in comparison with the systems known from the prior art (for example, SISAR or the Invader system). By coupling detection to an amplification reaction, sensitive detection of the target molecule is made possible, so that the analyses become more accurate. The system according to the invention requires both, i.e., polymerization activity and Taq polymerase activity. False-positive results are eliminated because faulty amplification due to incorrect binding of the primers does not result in the mediator region being split off because there is no complementary region for the probe region, so this also cannot bind. Furthermore, the mediator probe may be used in a multiplex PCR system and/or in a duplex PCR system in which it is then possible to work over multiple different detection molecules using several different fluorophores. This is a major advantage in comparison with the state-of-the-art systems because a number of target molecules can be detected in parallel in this way. A multiplex PCR system according to the invention may thus be used in diagnostic tests, for example, and can accelerate and simplify detection processes here, so that ultimately labor, materials and costs can be reduced.

In multiplex batches, various groups of multiple analytes can be detected with the same group of different detection molecules. It is advantageous here that the multiplex batches can be performed with the same groups of different detection molecules. This has not previously been possible in the prior art.

Another major advantage of the invention is the decoupling of the amplification reaction from detection. This makes it possible to use a standardized detection molecule, which can thus be produced in large quantities and therefore minimizes production costs.

It is also preferable for the detection molecule to be altered interaction with the mediator region by at least one auxiliary detection molecule comprising cleavage, digestion, strand doubling, internal hybridization, phosphorylation, dephosphorylation, amidation, binding or cleavage of a chemical group or a change in fluorescence, phosphorescence or luminescence. It is especially preferable here that the detection molecule has at least one fluorescence modification on the 5' terminal region and/or within the hairpin structure and that after the reaction with the mediator region, the fluorescence modifications are split off from the detection molecule by means of an auxiliary detection molecule and/or the 5' terminus of the hairpin structure of the detection molecule is removed and a change in the fluorescence signal is detected in the detection molecule.

A method in which at least one target molecule is an RNA is also preferred. In this case, the RNA is first transcribed to cDNA, preferably by reverse transcription. The resulting cDNA then becomes the template molecule to which the probe region of the mediator probe binds and which is amplified. It is especially advantageous that by transcription to cDNA, the RNA target molecule can also be amplified, because in this way only small amounts of RNA are needed to permit detection.

It is also preferable that a primer with sequence overhang is used in the transcription reaction, preferably reverse transcription. This makes it possible for a mediator probe to be used which can bind to the cDNA but not to the original DNA of the gene. A mediator probe is used for this, its probe region binding to a region comprising cDNA and overhang sequence. Since the original DNA does not have an overhang sequence, the mediator probe can differentiate between DNA and cDNA. This ensures that only the presence of the DNA is detected and that the DNA cannot trigger a corresponding signal.

Furthermore, this method may be used to detect RNA (by way of a corresponding cDNA with an overhang sequence) and DNA of the same gene in parallel. Two different detection molecules and two different mediator probes are preferably used for this purpose.

If samples of eukaryotic cells are analyzed, intron/exon sequences may also be used for differentiating between the RNA and DNA of the same gene. The probe region may thus be selected for binding to the cDNA, so that this covers a region of two transcribed exons. Since these regions are separated by an intron in the DNA of the gene, the mediator region cannot also bind to the DNA but only to the cDNA.

In another preferred method, at least one target molecule is a peptide or a protein. The template molecule is preferably an aptamer, such that the aptamer binds to the peptide or the protein and the binding site for the probe region of the mediator probe is therefore accessible. It is preferable for the aptamer alone not to have an accessible binding site for the probe region. The binding site becomes free and accessible only when the aptamer has interacted with the target molecule (peptide or protein). This preferably takes place through a change in the secondary structure. The probe region of the mediator probe can then bind to the aptamer. At the same time, the aptamer is available for the amplification reaction. By amplification of the aptamer, the mediator region is split off from the probe region and can thus bind to the detection molecule. The protein can thus be detected by the presence of the aptamer.

Since the aptamer is amplified, the signal is also amplified, so that even a very small number of peptides and/or proteins can still be detected.

It may also preferable to detect multiple target molecules, for example, DNA and protein or protein and RNA, at the same time.

Depending on the reaction conditions, the invention permits parallel detection of various molecules and classes of molecules, such as proteins and nucleic acids in one step by means of a multianalyte analysis, so that it is possible to compile a combined DNA-RNA protein profile of a sample.

The method according to the invention may therefore also be used for detection of one or more similar or different biomolecules in a mixture.

This preferably takes place by using the activity of a restriction enzyme, characterized in that the detection molecule has a protective chemical group on the 3'-terminal region, which is split off from the detection molecule by means of an auxiliary molecule after the reaction with the mediator region and thereby forms a 3'-terminal OH group.

It is also preferable for the method according to the invention to be used for a multiplex analysis. A multiplex analysis describes parallel detection of several target molecules in one reaction batch in particular.

A variety of different target molecules, which potentially exceed the degree of multiplexing of a PCR reaction, such as that described in the prior art, by several orders of magnitude can be detected with a standardized array layout and with adaptation of the mediator probes in a particularly inexpensive manner. A mediator region consisting of a nucleic acid molecule with a length of 20 nucleotides, for example, may be calculated to assume $4^{20}$ (approx. $1 \cdot 10^{12}$) possible different nucleotide sequences.

In direct interactions between target molecule and/or template molecule and mediator probe, the presence of the target molecule and/or the template molecule creates the activated mediator region from the mediator probe. In indirect interactions, the target molecule and/or the template molecule, in particular a nucleic acid, induces an interaction with the mediator probe and an auxiliary molecule, in particular an oligonucleotide, which does not interact structurally with the mediator probe. The auxiliary molecule described here functions as a primer and is elongated by a different type of auxiliary molecule, in particular a suitable polymerase, whereupon the mediator probe is cleaved into the mediator region and the probe region after a structural interaction with the polymerase. The mediator region is thus formed form the mediator probe in the presence of the target molecule. These auxiliary molecules are preferably selected from the group including catalysts, proteins, nucleic acids, natural substances, enzymes, enzyme systems, cell lysates, cell constituents, derivatives derived therefrom or synthetic molecules or a mixture thereof.

It was surprising that splitting off the mediator probe would result in a change in the physical and/or chemical properties of at least one region of the mediator probe, these properties being selected from the group comprising molecular weight (after splitting off the mediator probe, the fragments from this split are different from the mediator probe), enzymatic activity (the mediator probe advantageously changes its property of being able to initiate a detection reaction due to the new presence of a free 3' end), binding properties, including affinity or avidity, chemical reactivity (after splitting off the mediator probe, the cleavage fragment which contains the mediator region of the mediator probe, has a hydroxyl group on the 3' end, which can be elongated by an auxiliary molecule (for example, a polymerase), this is impossible for the uncleaved probe), presence of chemical groups, electric properties including conductivity, polarizability or charge and/or optical properties comprising absorption and emission of light (if the mediator probe is labeled with at least one fluorescent dye, an altered fluorescence signal can preferably be detected after the cleavage).

In a preferred embodiment, there is a serial interaction of the mediator region with multiple similar detection molecules, thus resulting in signal amplification. This increases the sensitivity of the detection reaction. In this embodiment, modified nucleotides are advantageously used for the synthesis of the detection molecule, allowing only a limited 5'-terminus degradation during the detection reaction. This can place through incorporation of one or more phosphothioate (PTO) modifications, for example, on the next-to-last nucleotide of the 5'-terminus during the synthesis of the molecule. The position of the PTO modification is preferably located in region 1, especially preferably between the fluorescence donor F and the fluorescence acceptor Q. FIG. 6 illustrates preferred positions of modified nucleotides. Preferred auxiliary detection molecules cannot split PTO bonds or can do so only with a low efficiency, and the 5' terminus (region 1) cannot be degraded beyond this nucleotide. Consequently, the mediator molecule is also not elongated further. Through suitable adjustment of the reaction conditions, the auxiliary detection molecule and the mediator molecule may dissociate from the detection molecule and may then be available again for activation of another detection molecule.

In a particularly preferred embodiment, a mediator molecule may interact with multiple identical specific detection molecules in each reaction cycle and/or chronological segment of the reaction and thereby trigger a signal-generating detection reaction. The sensitivity of the reaction is increased significantly because a cumulative effect occurs due to amplification of the target molecule.

It is also preferable for the detection to be allowed to take place while using suitable devices in real time and/or for an end-point measurement to be detectable. In both cases, the embodiment according to the invention advantageously does not require any post-processing such as washing steps or incubation steps, for example.

In another preferred embodiment, which is compatible with the PTO modification described above but is not limited to a combined application, an abasic nucleotide (tetrahydrofuran THF modification) is incorporated into region c, which cannot form any hydrogen bridges with a complementary nucleotide. This suppresses the elongation reaction of the mediator region on the opposite position of the abasic nucleotide, whereupon the auxiliary detection molecule and the elongated mediator region dissociate from the detection molecule (see FIG. 7). Use of one of the preferred modifications permits serial interaction of a mediator molecule with a plurality of detection molecules, which can be referred to in the sense of the present invention as mediator recycling in particular. The mediator region is elongated by means of an auxiliary detection molecule in the first interaction with a detection molecule and subsequent processing and can also interact with additional detection molecules in this elongated state and can permit degradation of the 5'-terminus—and thus also of the fluorescence acceptor Q—with the help of a suitable auxiliary detection molecule (for example, polymerase with 5' nuclease activity). This reaction mechanism permits signal amplification because regardless of a target molecule amplification a signal is generated and amplified. If the target molecule is amplified with the help of suitable auxiliary molecules and if this process is linked to mediator probe cleavage, there is an accumulation of the mediator, which combines target molecule amplification with signal amplification and lowers the limit of detection in the detection reaction by several orders of magnitude. This was completely surprising and is not described in the prior art. Furthermore, it constitutes a departure from what is customary in the art. After this process has taken place, the reaction conditions may advantageously be altered, for example, by raising the reaction temperature so that the enzyme, for example, the polymerase, and the elongated mediator region will dissociate from the detection molecule. Those skilled in the art are aware of the fact that the reaction conditions can undergo cyclic changes, so that a mediator molecule can interact with a plurality of similar detection molecules in a particularly preferred embodiment of the invention. This surprisingly results in signal amplification, which significantly increases the sensitivity of the reaction.

The detection reaction is preferably designed so that, in contrast with the mediator region, the uncleaved mediator probe does not trigger any signal generating reaction and thus no false-positive results are generated. The mediator region derived from splitting off the mediator probe has a 3'-OH terminus that is particularly advantageous for a polymerase-mediated elongation reaction. If this cleavage does not occur, then elongation of the mediator is impossible because the mediator sequence is covalently linked to the hybridization sequence of the mediator probe (see FIG. 8). In addition, a nonspecific elongation of the 3'-terminus of the mediator probe can be prevented with a phosphate group or some other chemical groups, for example.

A local, detectable (fluorescence) signal preferably occurs due to the event of interaction of the mediator region with the detection molecule. If enough detection molecules are activated by the preferred mediator elongation with the resulting cleavage of the 5'-terminus, the signal is amplified and can be detected by means of suitable detection equipment (optical in particular). This permits detection in the presence of the reaction mixture and does not require any processing steps. The preferred embodiment has the advantageous property of allowing detection within a suitable reaction space without having to open it after the reaction has been performed. This avoids the problems that have been described in the prior art as being associated with microarray analyses due to hybridization steps, staining steps and/or washing steps that involve additional labor and a high risk of contamination. The preferred embodiment can therefore be regarded as a departure from what is customary in the art because it opens up a new technical field and solves a problem which has long been in existence in the prior art.

In addition to the advantages described above, the preferred embodiment allows the resulting signals to be read out at any point in time during the reaction. This permits real-time monitoring of the reaction, which is necessary for quantification of nucleic acid amplification or for determination of the binding kinetics of protein interactions, for example. The preferred embodiment is thus differentiated from the prior art, in which only end point determinations are typically performed and therefore signal detection cannot be performed at just any point in time.

Multiplex analyses determine the detection of multiple different analytes in a reaction mixture. For increasing the degree of multiplexing of the preferred reaction, the use of "n" different mediator probes for "n" different target molecules is preferred. In a preferred embodiment, a mediator probe whose region 1 interacts specifically with the target molecule may be assigned to each target molecule to be detected. Region 2 of the respective mediator probe, which represents the mediator after successful cleavage, does not have affinity for the target molecule nor is it complementary to it, but instead it represents a specific interaction particle for a defined detection molecule. Therefore a detection molecule is indirectly assigned to each target molecule, its assignment being made by the mediator probe. Detection of various target molecules necessitates a variety of detection molecules. Based on the preferred structure, it is sufficient if these molecules differ only in region 5. Virtually any degree of parallelism is possible because any series of sequences are possible and thus a detection method for a multiparameter analysis is made available. It is therefore preferable to use the system as a detection method for a multiparameter analysis. The system may preferably be used for detection of one or more similar or different biomolecules in a mixture. Furthermore, the system may advantageously be used for amplification of at least one or in particular multiple target molecules, but these are advantageously not identical target molecules. In addition, it may be preferable to use the system while utilizing the activity of a restriction enzyme, such that the detection molecule has a chemical protective group on the 3'-terminal region, which is split off from the detection molecule with the help of an auxiliary molecule after the reaction with the mediator region and a 3'-terminal OH group is generated.

In a solution to the problem according to the invention, the mediator probe with the sample to be analyzed is applied to the detection molecules immobilized in a disposable reaction cartridge, then processed by a suitable method and detected. The reaction cartridge may then be discarded without subsequent contamination. In addition, an amplification step may be performed in a reaction vessel prior to or in parallel with detection, so that optionally a specific enrichment of the target molecule can be accomplished. Therefore, the transfer of reaction batches with a high target molecule concentration (for example, post-PCR batches) from an amplification region to a detection region and the associated steps and contamination risks become superfluous.

The present invention also relates to a processing machine and a microfluidic reaction cartridge for use of the method or the system. The cartridge has at least one reaction chamber in which a universal detection array in particular is present, preferably consisting of a locally resolved arrangement of one or more detection molecules.

The processing machine preferably subjects the cartridge and the reaction liquid to a constant temperature and/or a defined temperature profile (heating and/or cooling). The processing machine may detect a change in the detection molecule by a preferred system or method. For example, a fluorescence signal may be used in this way. In addition, the machine may permit liquid transport within the reaction cartridge by means of active or passive elements. The preceding discussion is to be applied to the mediator probe, the system and the method.

The cost of performing a method according to the invention can be reduced because, in one possible embodiment, the application of the sample to be analyzed and the required reagents can be performed automatically in a disposable cartridge. This eliminates the need for using trained personnel for these steps.

In another preferred embodiment, the invention relates to a kit comprising at least one detection molecule in the sense of the invention, polymerases and dNTPs. The kit thereby provided may be used in any detection reaction and therefore is advantageously a universal detection kit.

BRIEF DESCRIPTION OF THE FIGURES

The invention as well as the prior art will be explained in greater detail below with reference to figures and exemplary embodiments, although it is not limited to these. They show:

FIG. 1(A-D) shows various solid-phase-based detection methods after invasive cleavage of an immobilized probe. (A) Direct fluorescence-based invasive cleavage detection. Possibility 1: The probe is immobilized on the substrate surface. The invader oligonucleotide (upstream oligonucleotide) and the target sequence (target) are added to the reaction solution (see FIG. 1). Possibility 2: The probe and the Invader oligonucleotide are immobilized on the surface. The target sequence is added to the reaction mix (see FIG.

2). In both cases the probe molecule is cleaved, which results in a change in the fluorescence signal. Source: Lu, M. C. et al. 2002, A surface invasive cleavage assay for highly parallel SNP analysis, Hum. Mutat., 19, 416-422.

(B) Indirect cleavage reaction. A Dabcyl-modified probe is immobilized on a solid phase. After successful invasive cleavage, a biotin-labeled linker to which streptavidine-coated gold particles are bound is ligated. Source: Nie, B. et al., 2006, Quantitative detection of individual cleaved DNA molecules on surfaces using gold nanoparticles and scanning electron microscope imaging, Anal. Chem., 78, 1528-1534.

(C) Indirect cleavage detection by subsequent rolling circle amplification. After invasive cleavage of an immobilized 5'-labeled probe, a ligation step is performed with subsequent rolling circle amplification. Two different strategies are represented, in which only the probe (a) is immobilized and/or the probe and the invader oligonucleotide (b) are immobilized. Source: Chen, Y. et al., 2004, Surface amplification of invasive cleavage products, J. Amer. Chem. Soc., 126, 3016-3017.

(D) Indirect fluorescence-based cleavage detection. A labeled detection probe is hybridized on a fluorescence-labeled probe and the fluorescence signal is detected. After washing steps and invasive cleavage have been performed, there is an additional hybridization step with the detection probe that has been described. The subsequent fluorescence measurement allows an inference regarding the presence of the target sequence in the reaction batch. Source: Lockett, M. R. et al., 2007, Molecular beacon-style hybridization assay for quantitative analysis of surface invasive cleavage reactions, Anal. Chem., 79, 6031-6036.

Figure 1:
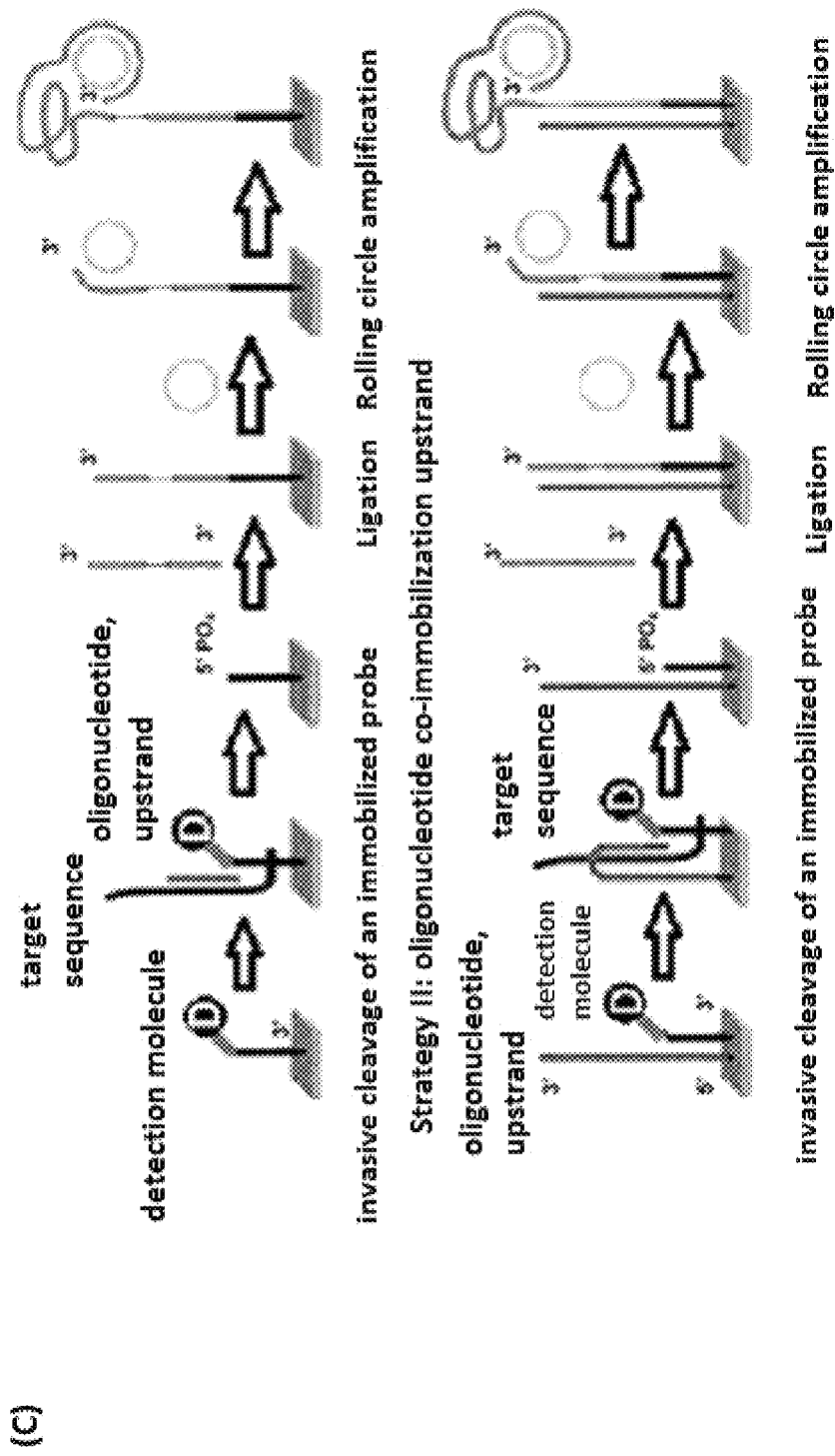
FIG. 1(A-D) Various solid-phase-based detection methods after invasive cleavage of an immobilized probe FIG. 2 Preferred structure of a mediator probe FIGS. 3A, B Preferred interaction of the mediator probe with the target molecule and mediator probe cleavage FIGS. 4A, B Illustration of a preferred detection molecule FIGS. 5i)-vi) Schematic diagram of a preferred elongation of an enzymatic mediator FIG. 6 Schematic diagram of a preferred position of chemical modification within the detection molecule FIGS. 7i)-v) Preferred detection of the mediator with the help of an immobilized detection molecule FIG. 8 Preferred interaction of the mediator probe and the detection molecule FIG. 9 Schematic diagram of the preferred areas of application of the mediator probe technology FIG. 10 Normalized fluorescence plot of PCR using a preferred mediator probe and in the reaction vessel of immobilized detection molecules FIG. 11(A)-(D) Schematic diagram of a preferred PCR method FIG. 12(A)-(D) Comparison of the characteristic of mediator probe PCR and hydrolysis probe PCR FIG. 13(A)-(D) Amplification of various targets with mediator probe PCR and hydrolysis probe PCR.
Figure 1:
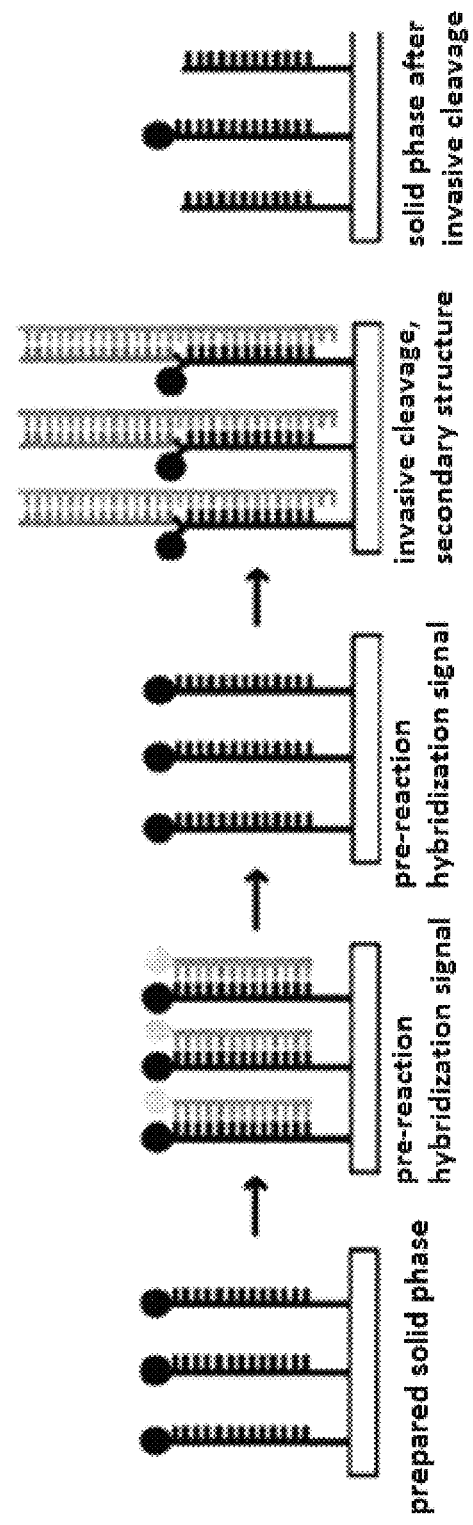
Figure 2:
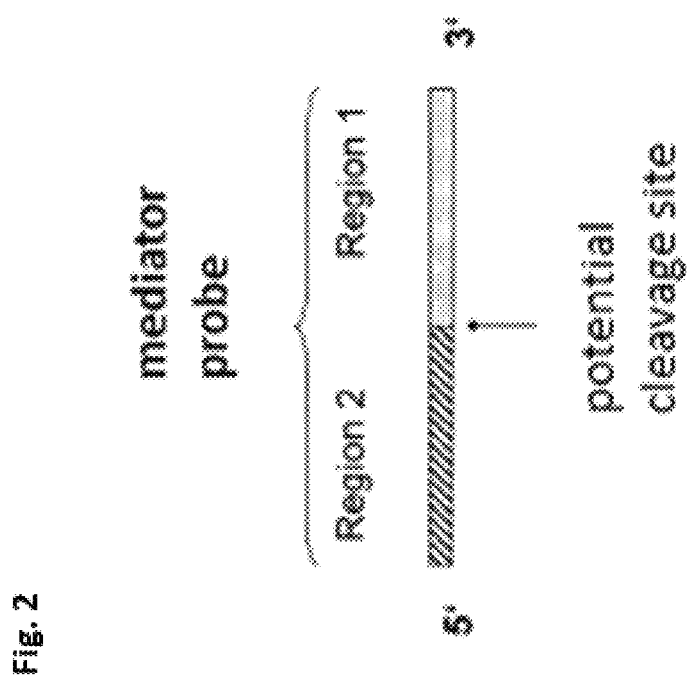

FIG. 2 shows a preferred design of a mediator probe. The mediator probe consists of an oligonucleotide in particular and is subdivided into two functional regions. Region 1 has an affinity for or is complementary to the original and/or target molecule, while region 2 interacts exclusively with a specific detection molecule. There is a potential cleavage site between these regions.

Figure 3:
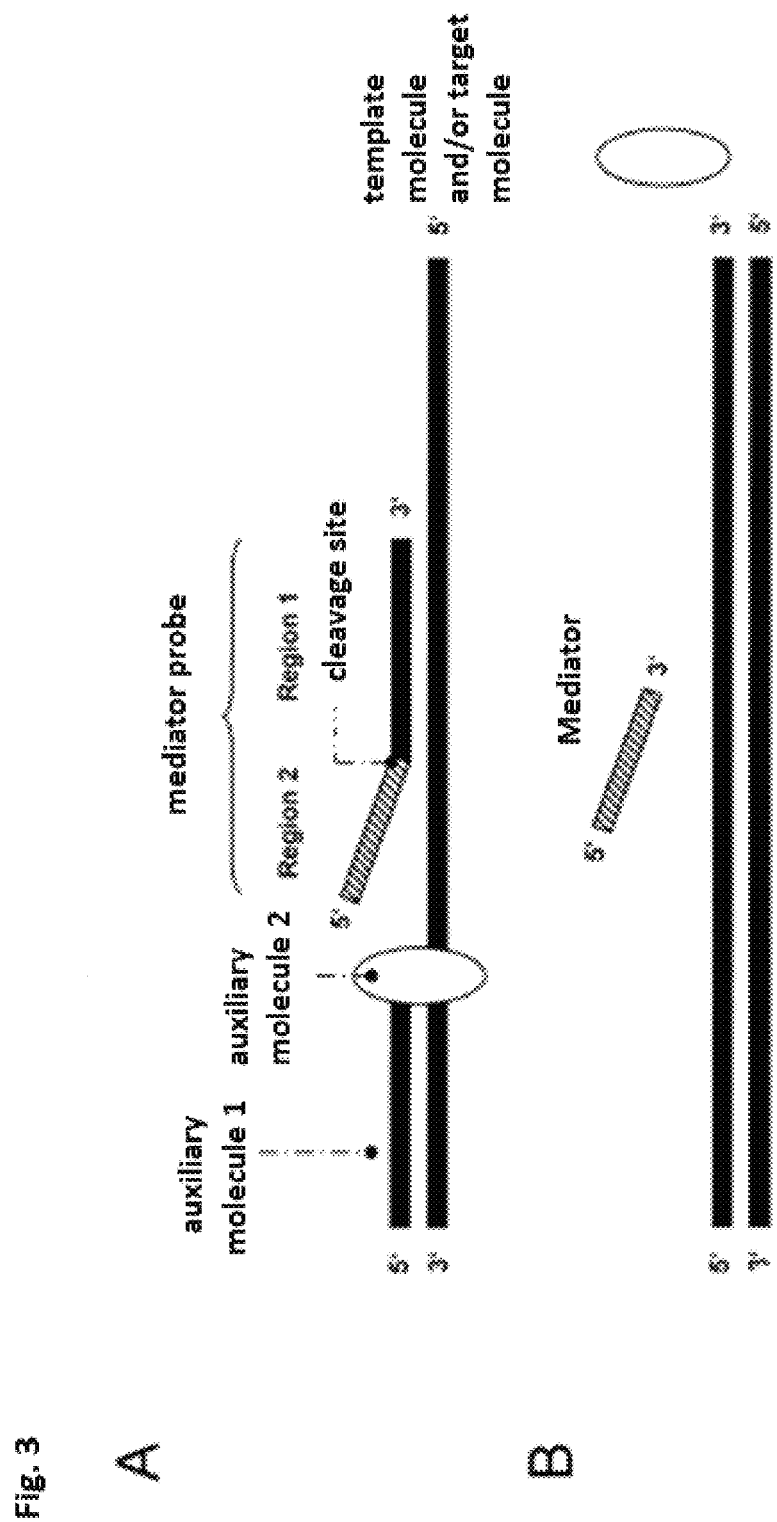

FIG. 3 shows a preferred interaction of the mediator probe with the template molecule and/or target molecule and mediator probe cleavage. The mediator probe, auxiliary molecule 1 (here: primer) and auxiliary molecule 2 (here: enzyme with polymerization and nuclease activity (polymerase)) interact with the template molecule and/or target molecule (here: nucleic acid sequence) (A). Under suitable reaction conditions, the primer is elongated by the polymerase and the mediator probe is cleaved, whereupon a mediator region is released (B).

FIGS. 4A, B show a diagram of a preferred detection molecule. Linear representation (A). Diagram of 3'-immobilized detection molecule forming the secondary structure (B). The reverse complementary sequence segments, whose interaction results in the secondary structure of the detection molecule, are represented as black regions, while the mediator hybridization sequence is represented as a diagonally striped region. Region a may be present with or without PTO modifications.

Figure 4:
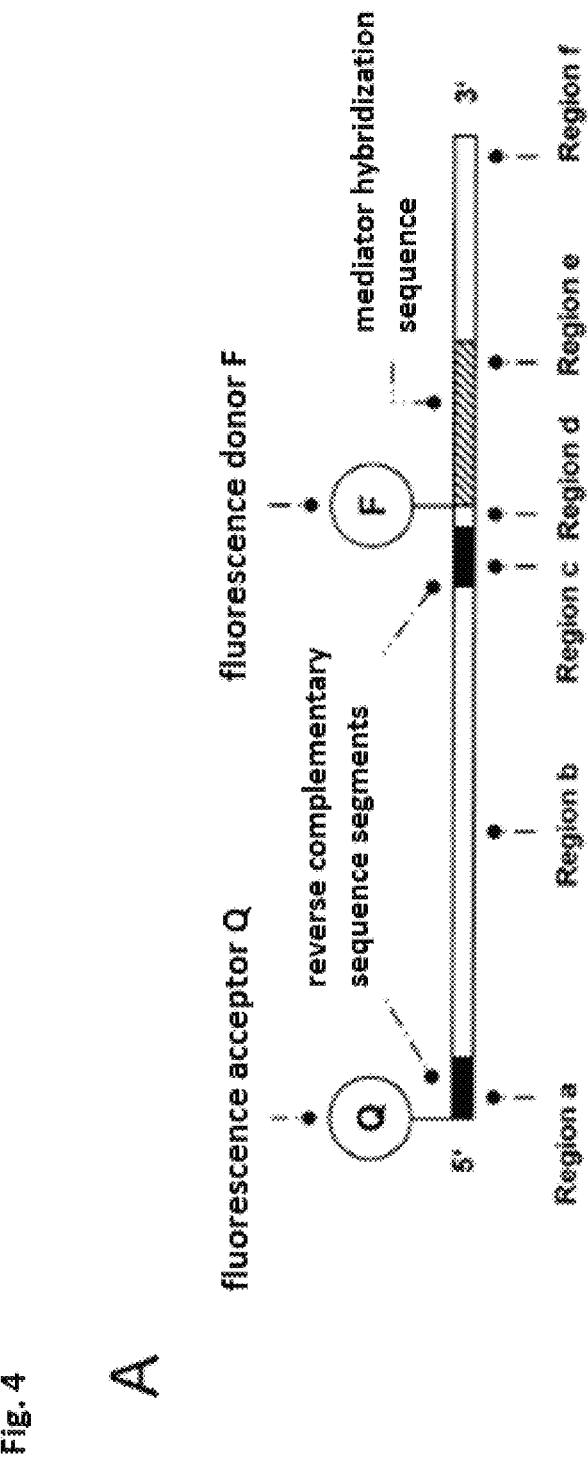
Figure 4:
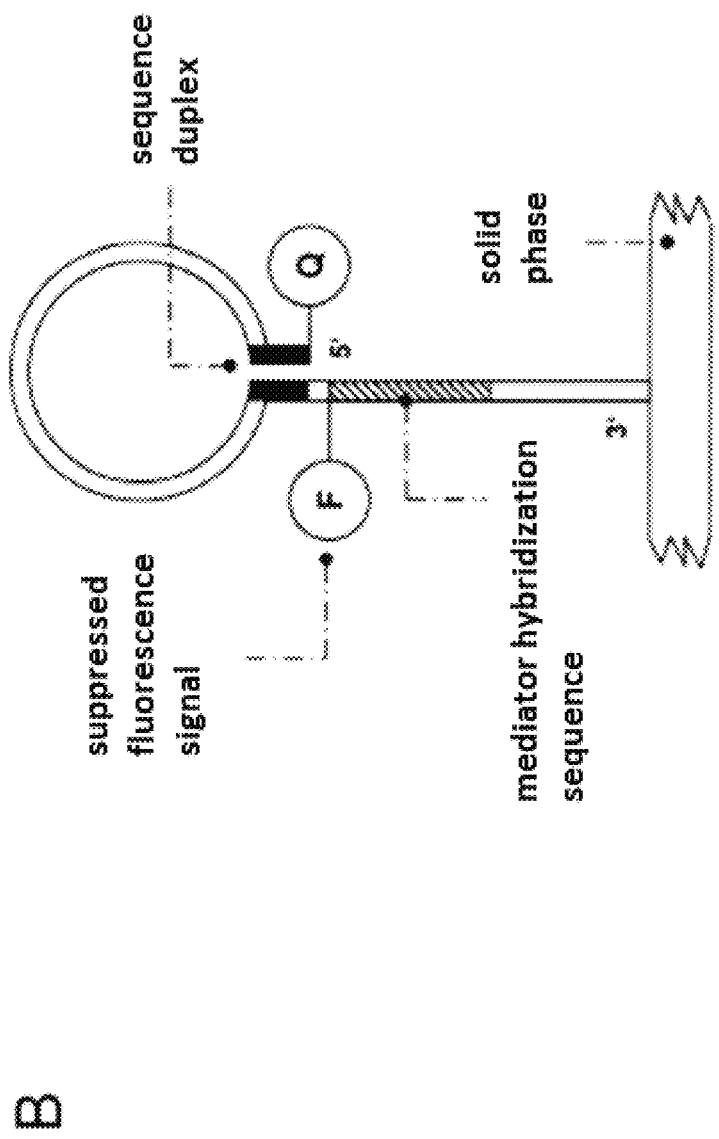

In a preferred embodiment, a detection molecule consists of an oligonucleotide which is subdivided into multiple regions (cf. preferably FIG. 4).

Region a (=first region) comprises the 5'-terminus of the detection molecule, which consists of a sequence segment and a fluorescence acceptor Q in a preferred embodiment. Region c is a reverse complementary sequence of region a and is separated from that by region b. Region d (=third region) separates region c and region e (=second region), which can interact specifically with a mediator molecule. Region f (=fourth region) comprises the 3'-terminal sequence region, which preferably has a chemical modification and thus permits a directed immobilization of the oligonucleotide. A fluorescence donor F is associated with a portion of region b to region f, for example, region d, in a manner with which those skilled in the art are familiar. It is preferable for the detection molecule to have a hairpin structure. Region a and region c of the detection molecule form a defined secondary structure (referred to a hairpin structure in the sense of the present invention) under reaction conditions, in which the 5'-terminus is hybridized with an internal sequence segment.

FIGS. 5 i)-vi) show a schematic diagram of a preferred elongation of an enzymatic mediator. i) A detection molecule is present, immobilized on a solid phase, and assumes a defined secondary structure under reaction conditions. Two suitable fluorescence modifications F and Q interact with one another, thereby suppressing the fluorescence signal of F. ii) The mediator can interact with the detection molecule at a defined position (mediator hybridization sequence region 5), and iii-iv) is thereby enzymatically elongated by an auxiliary detection molecule (here: polymerase). In doing so, the fluorescence acceptor molecule Q is split off from the detection molecule, so that the fluorescence intensity of the fluorescent dye F is restored. vi) After splitting off from region 1, the detection molecule assumes a linear confirmation, so that there can be a further elongation of the mediator. The mechanism shows in FIG. 5 also takes place when PTO modifications are present.

Figure 6:
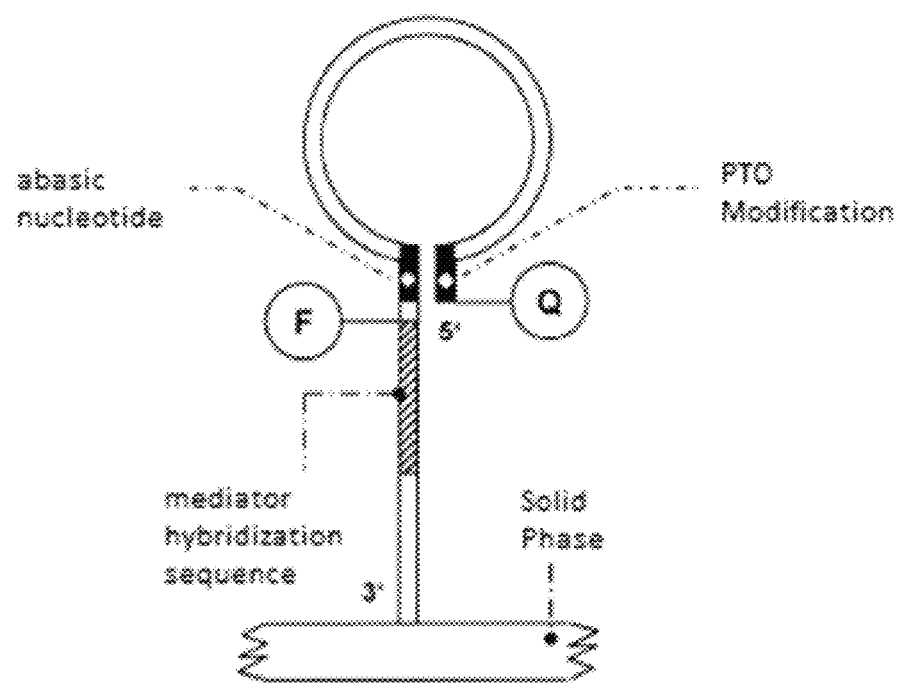

FIG. 6 shows a schematic diagram of a preferred position of a chemical modification within the detection molecule. Modified nucleotides which terminate a potential mediator elongation in a defined position are incorporated at suitable sequence positions within region 1 and/or region 2.

Figure 7:
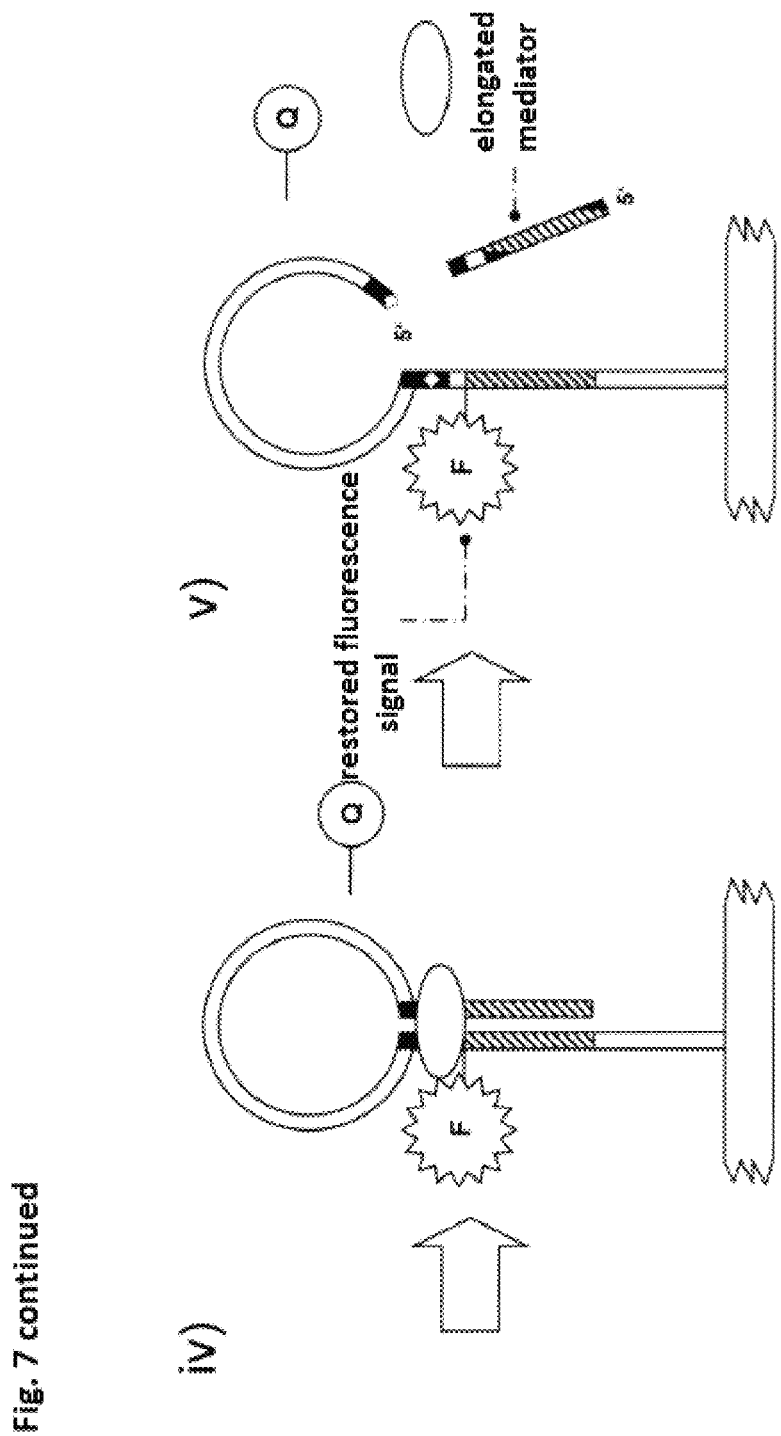

FIG. 7 shows a preferred detection of the mediator with the help of an immobilized detection molecule. i) A detection molecule is immobilized on a solid phase and assumes a defined secondary structure under reaction conditions. Two suitable fluorescence modifications F and Q interact with one another, thereby suppressing the fluorescence signal of F. The 3'-terminal sequence region is unpaired and serves as a potential mediator hybridization sequence (diagonally striped region). ii) In this defined position, the mediator can interact with the detection molecule and iii-iv) is enzymatically elongated by an auxiliary detection molecule (here: polymerase). v) Then the fluorescence acceptor molecule Q is split off from the detection molecule, so that the fluorescence intensity of the fluorescent dye F is restored. After a suitable period of time, the reaction conditions are altered by heating the reaction solution so that the polymerase and the elongated mediator are dissociated away from the detection molecule.

Figure 8:
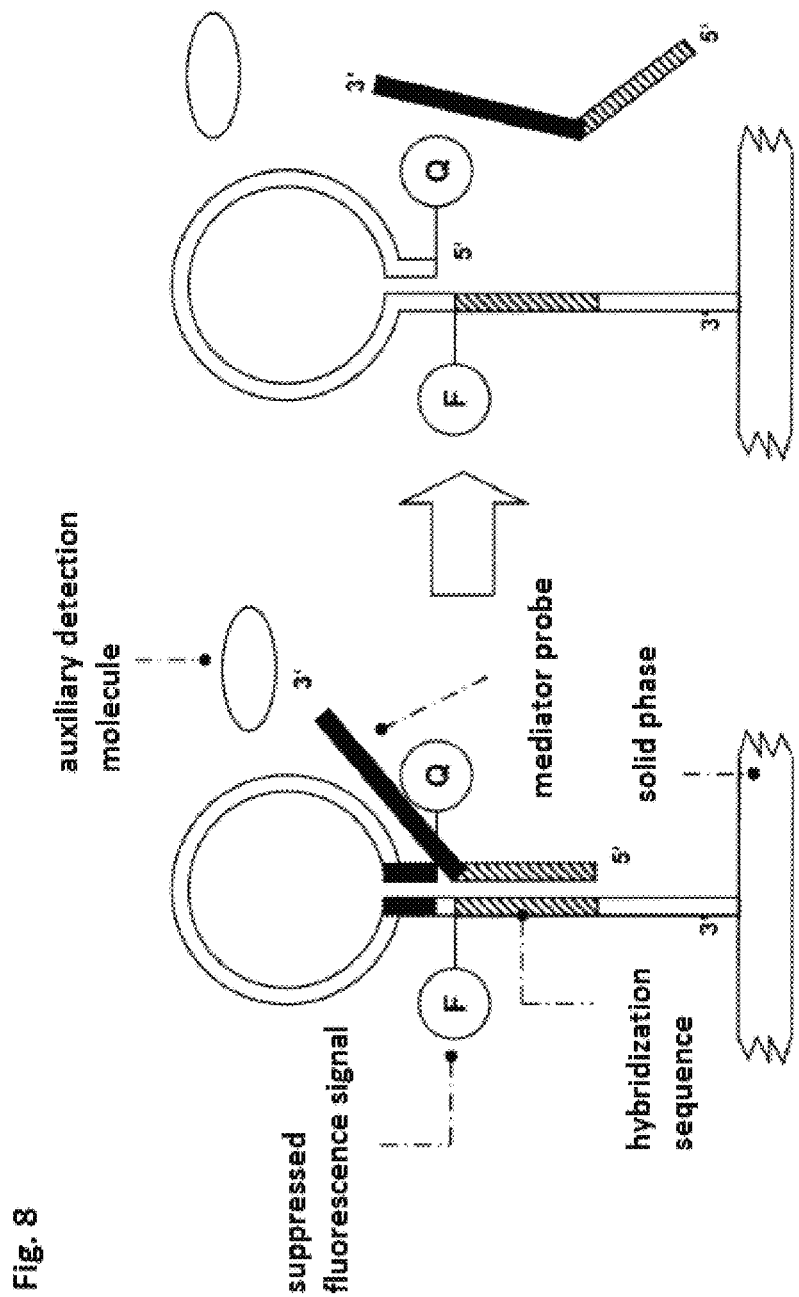

FIG. 8 shows a preferred interaction of mediator probe and detection molecule. If the uncleaved mediator probe interacts with the detection molecule, no enzymatic elongation reaction will take place even in the presence of a suitable auxiliary detection molecule because it requires a 3'-OH terminus in the mediator sequence. This prevents false-positive signals from being generated. In addition, a 3'-terminal modification may be present to suppress a non-specific elongation.

Figure 9:
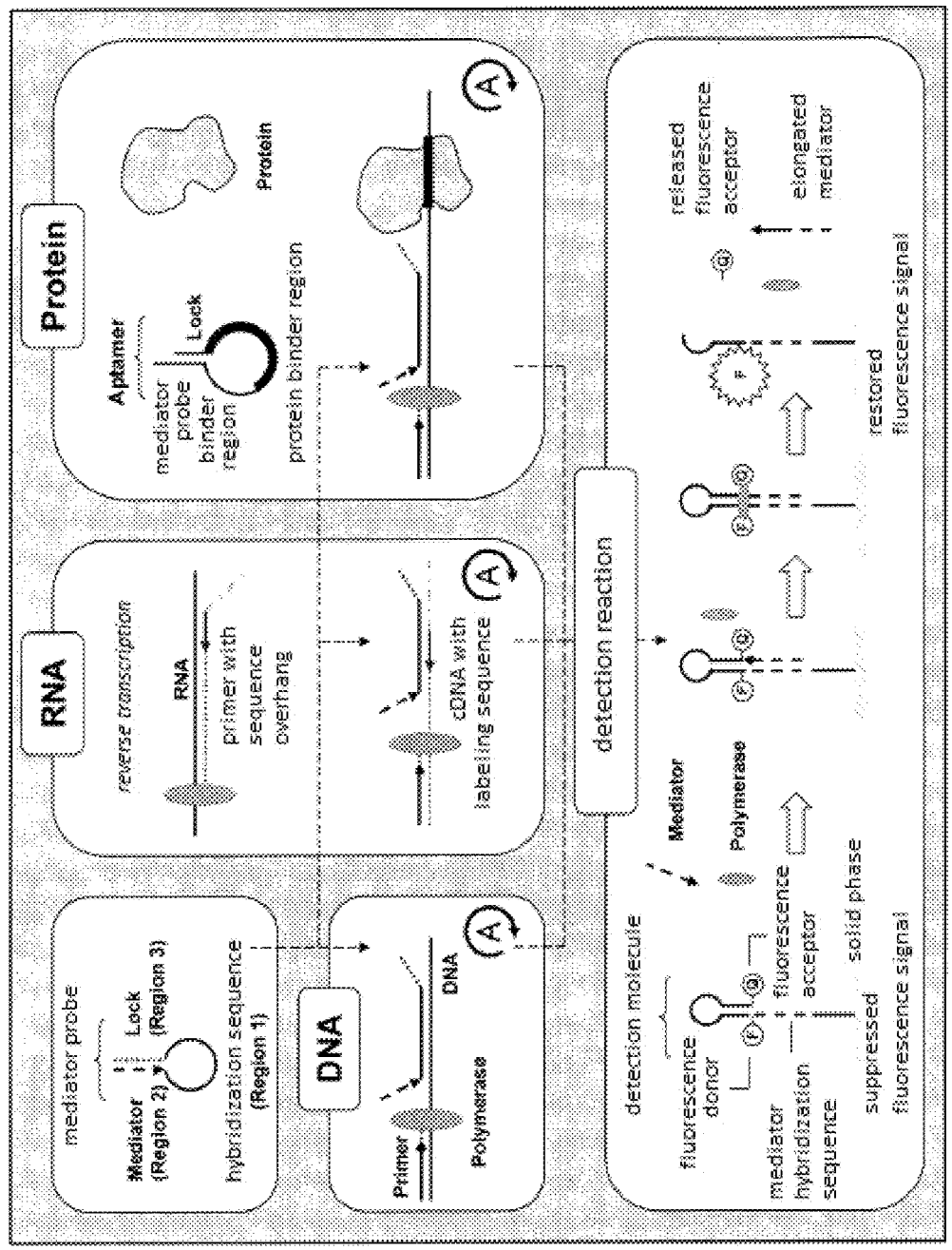

FIG. 9 shows a schematic diagram of the preferred areas of application of the mediator probe technology. The mediator probe technology can detect DNA, RNA transcribed to cDNA or protein-associated aptamers. Processing of the mediator probe may optionally be integrated into an amplification step (A) of the target molecule. This shows detection by means of an immobilized mediator-specific detection molecule. By interaction with an auxiliary molecule (here: polymerase), a change in state of the detection molecule is generated by a mediator-mediated reaction (here: change in fluorescence).

Figure 10:
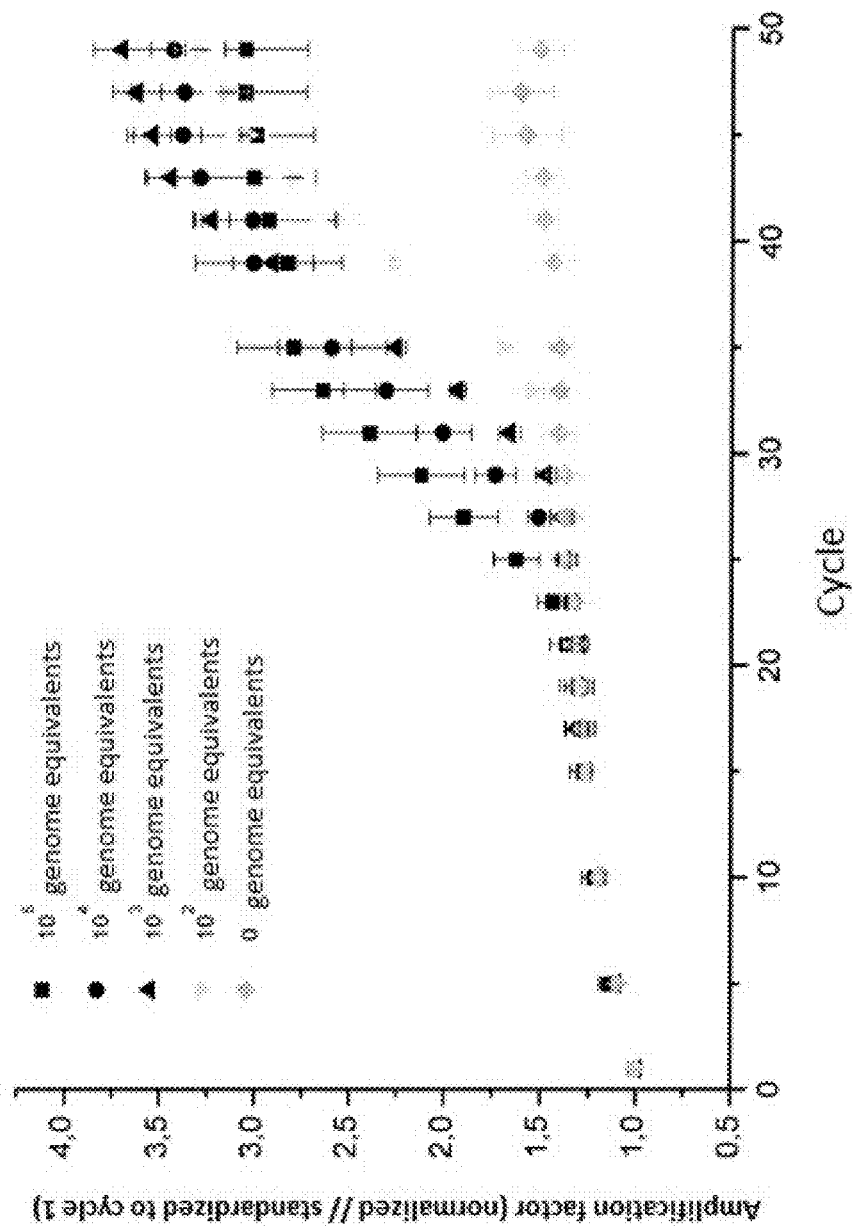

FIG. 10 shows a normalized fluorescence plot of a PCR using a preferred mediator probe and detection molecules immobilized in the reaction vessel. The reagents, including target sequence-specific primers as well as the mediator probe and various *Staphylococcus aureus* genome equivalents, among other things, were pipetted into a suitable reaction vessel with immobilized detection molecules and sealed with a suitable sealing film. The reaction was performed in a thermocycler, so that the measurement of the fluorescence was performed in a separate instrument at the cycles indicated. In each PCR cycle, the sequence segment to be amplified was doubled, so that a mediator was derived from the cleavage of a mediator probe with each duplication step. The released mediator interacted with the detection molecule in a suitable manner, resulting in a detectable fluorescence signal. The plot shows a correlation with the quantity of DNA and the fluorescence profile. The fluorescence intensities have been standardized to the value of cycle 1 (the measured value of cycle 37 was falsified due to condensation on the cover film and therefore was not taken into account).

Figure 11:
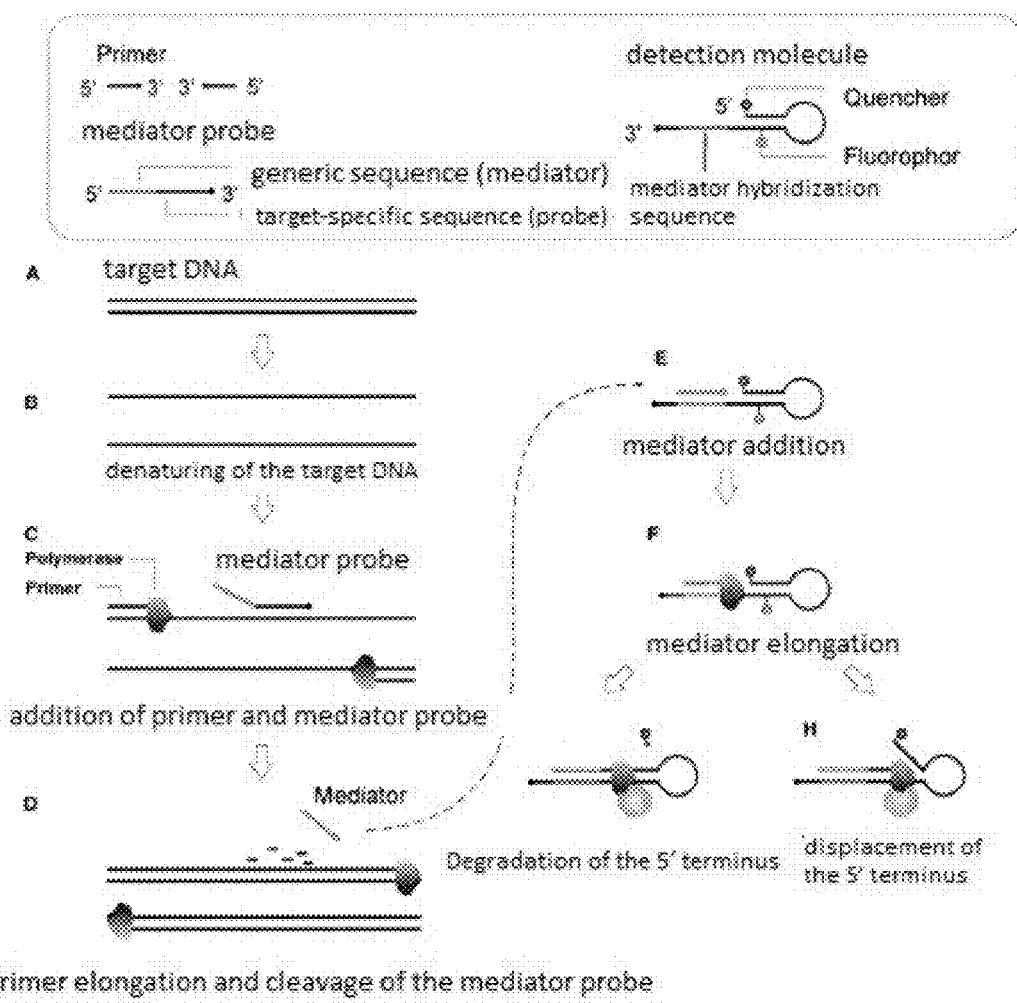

FIG. 11 shows a schematic diagram of a preferred method. Steps A through H illustrate the amplification reaction and detection. A nucleic acid target is at the same time the target molecule and the template molecule in the case illustrated here. After denaturing (B), the mediator probe, the primers and polymerase are added (C). Step (D) illustrates the elongation of the primers as well as splitting off the mediator probe and degradation of the probe region. The mediator region is released in this step. The mediator region is then added (E) to a detection molecule (=universal reporter). In step (F), the mediator region is elongated by a polymerase. Dequenching may be performed by two methods: either by way of sequential degradation of the 5' end of the detection molecule and release of the quencher radical (G) or by displacement of the 5' end and unfolding of the hairpin structure (H). Then all the steps are performed in a thermocycler.

Figure 12:
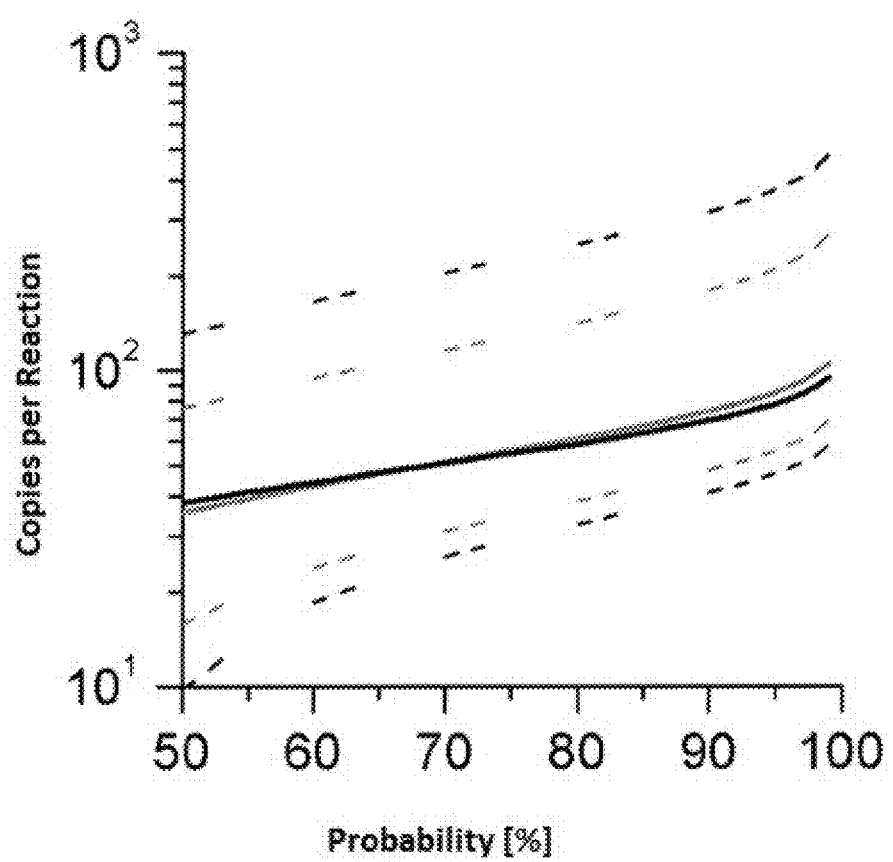
Figure 12:
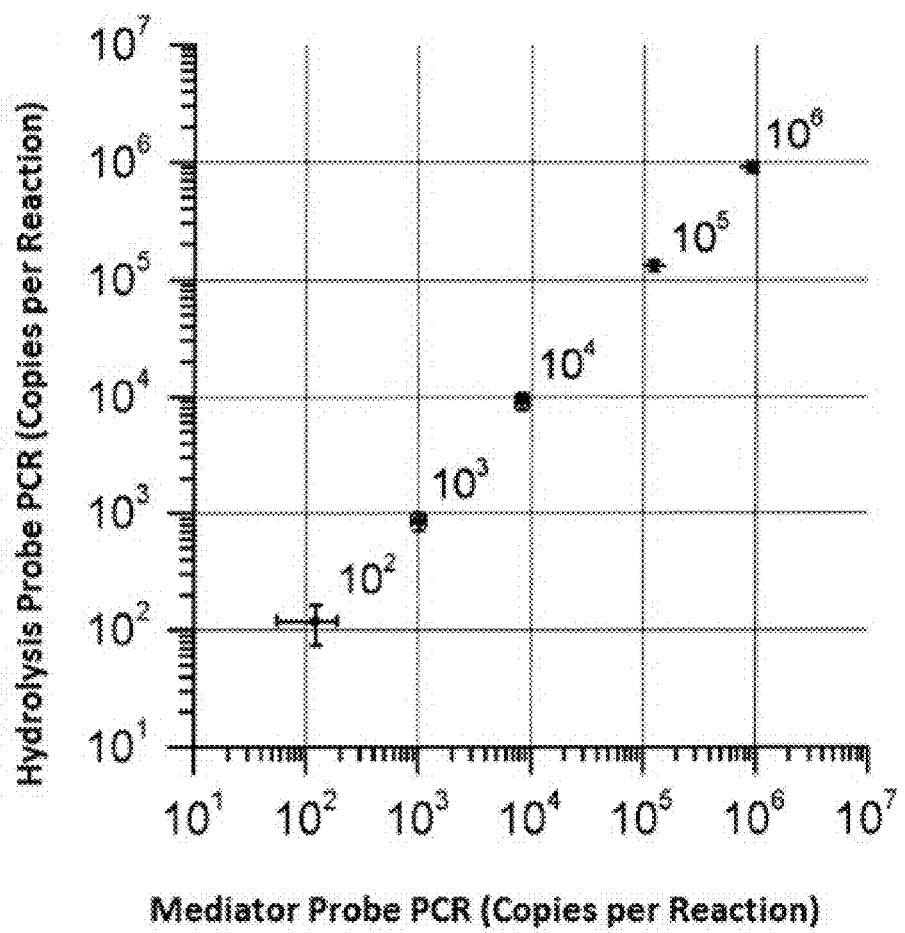
Figure 12:
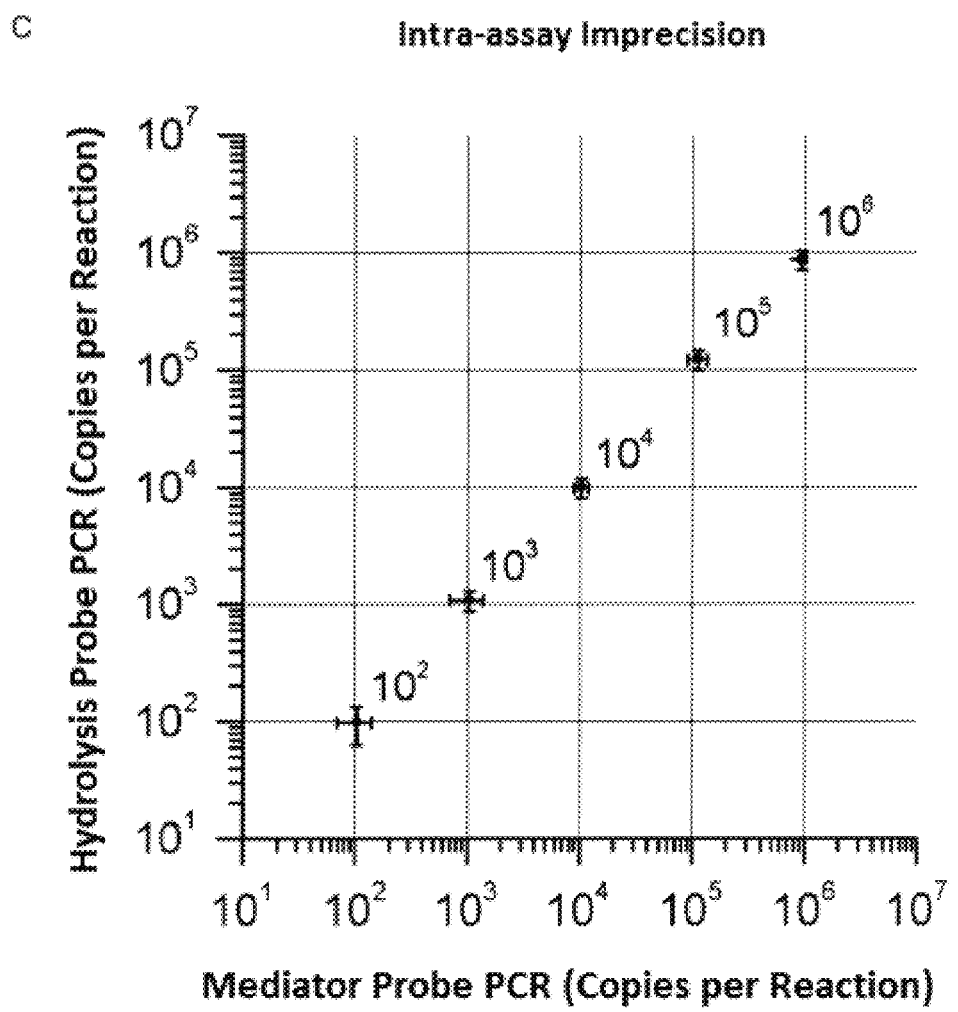
Figure 12:
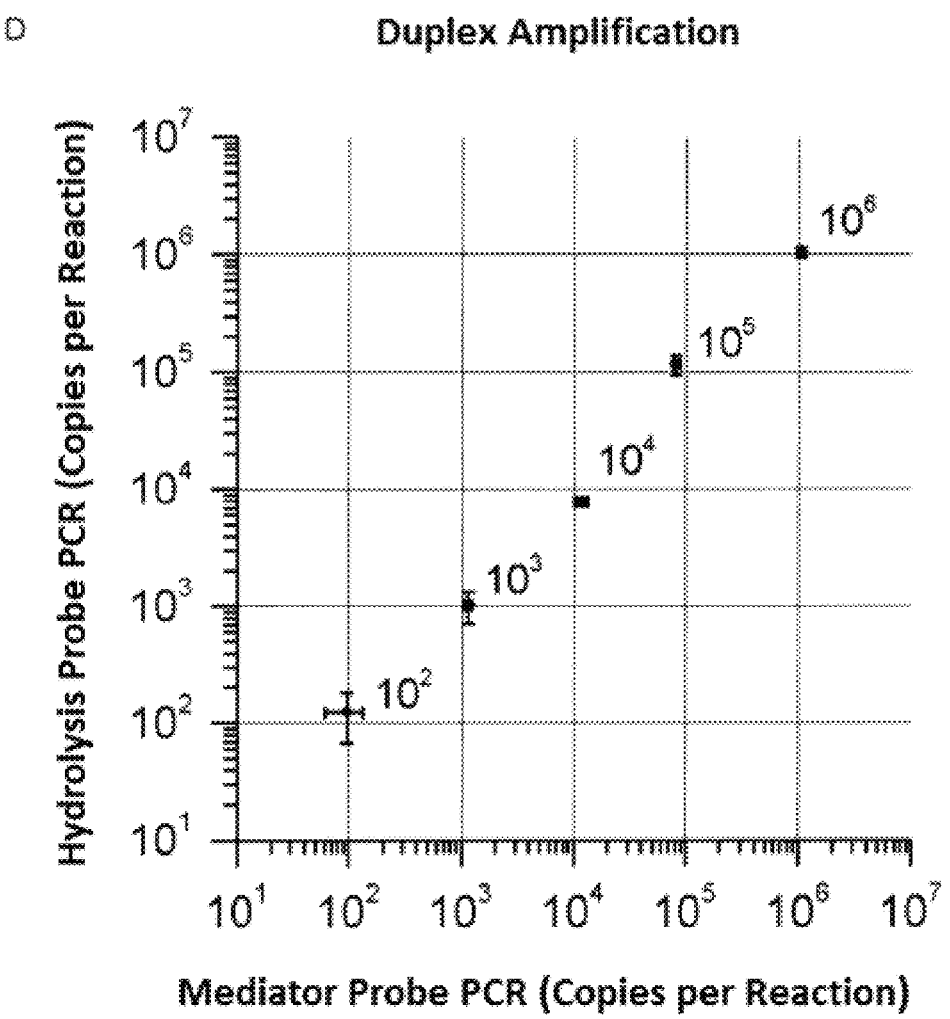

FIG. 12 shows a comparison between various characteristics of mediator probe PCR and hydrolysis probe PCR in FIG. 12. Various concentrations of HAPV18DNA were amplified and controls without original DNA were used. The calculated number of copies of the mediator probe PCR were plotted on the x axis. The number of copies of hydrolysis probe PCR (B to D) are plotted on the y axis. A shows the LOD or limit of detection for HPV18 detection. The probability of successful amplification (x axis) for a certain number of input copies (y axis) was determined with probit analyses. The mediator probe resulted in the black lines, and the hydrolysis probe resulted in the gray lines. The dashed lines shown at the top and bottom indicate 95% CI. The intra-assay variance for five different DNA concentrations is given in (B); (C) shows the interassay variance for five DNA concentrations in five different PCR passes. The diagram in (D) shows the results of duplex PCR.

Figure 13:
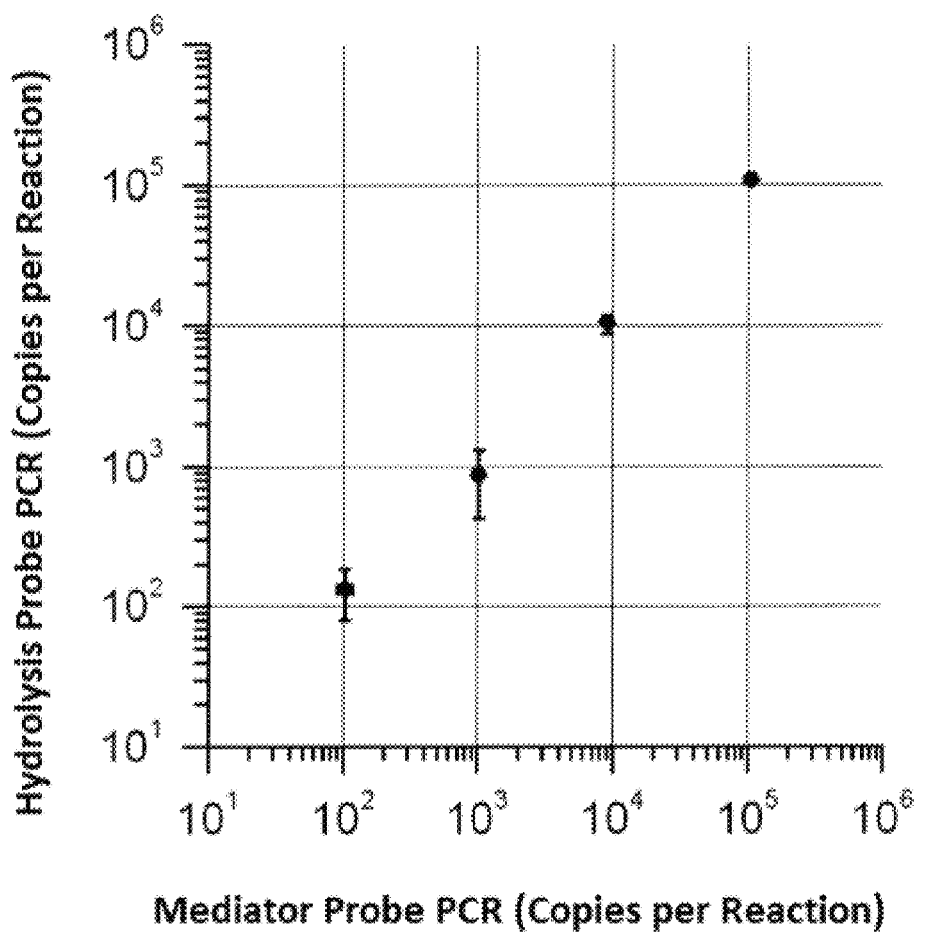
Figure 13:
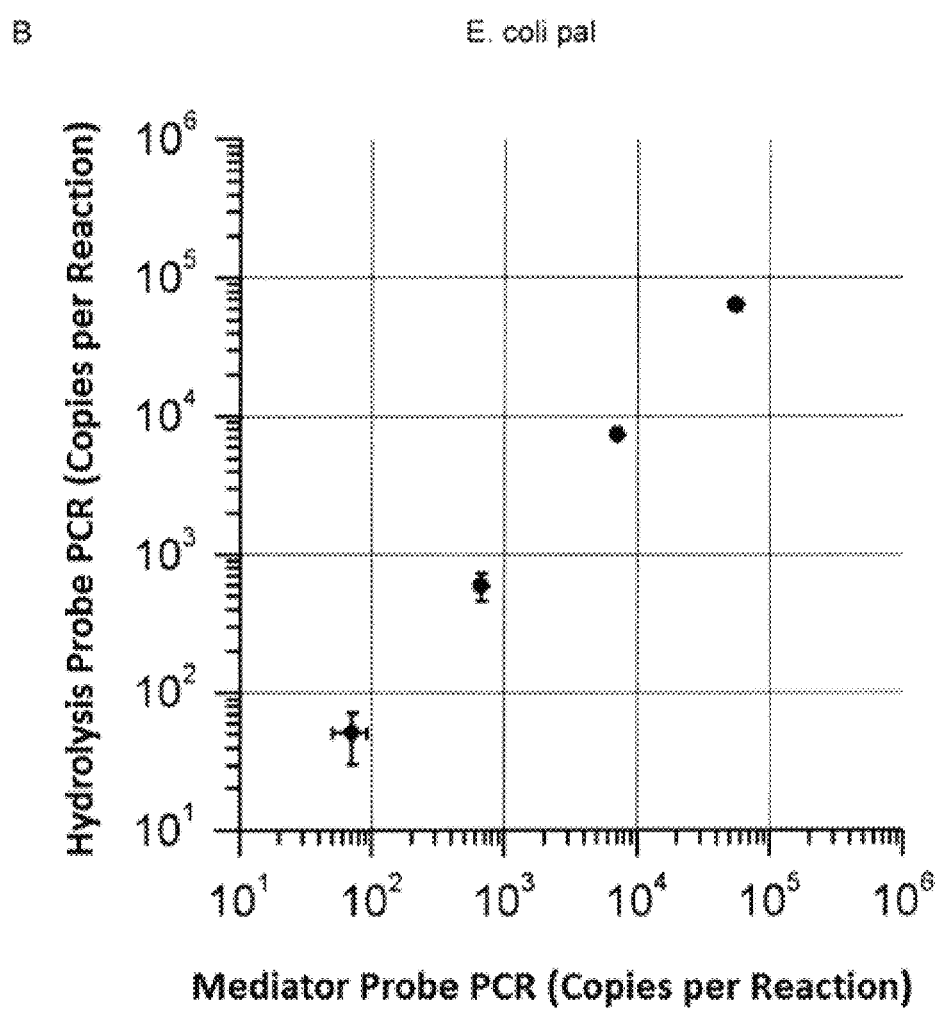
Figure 13:
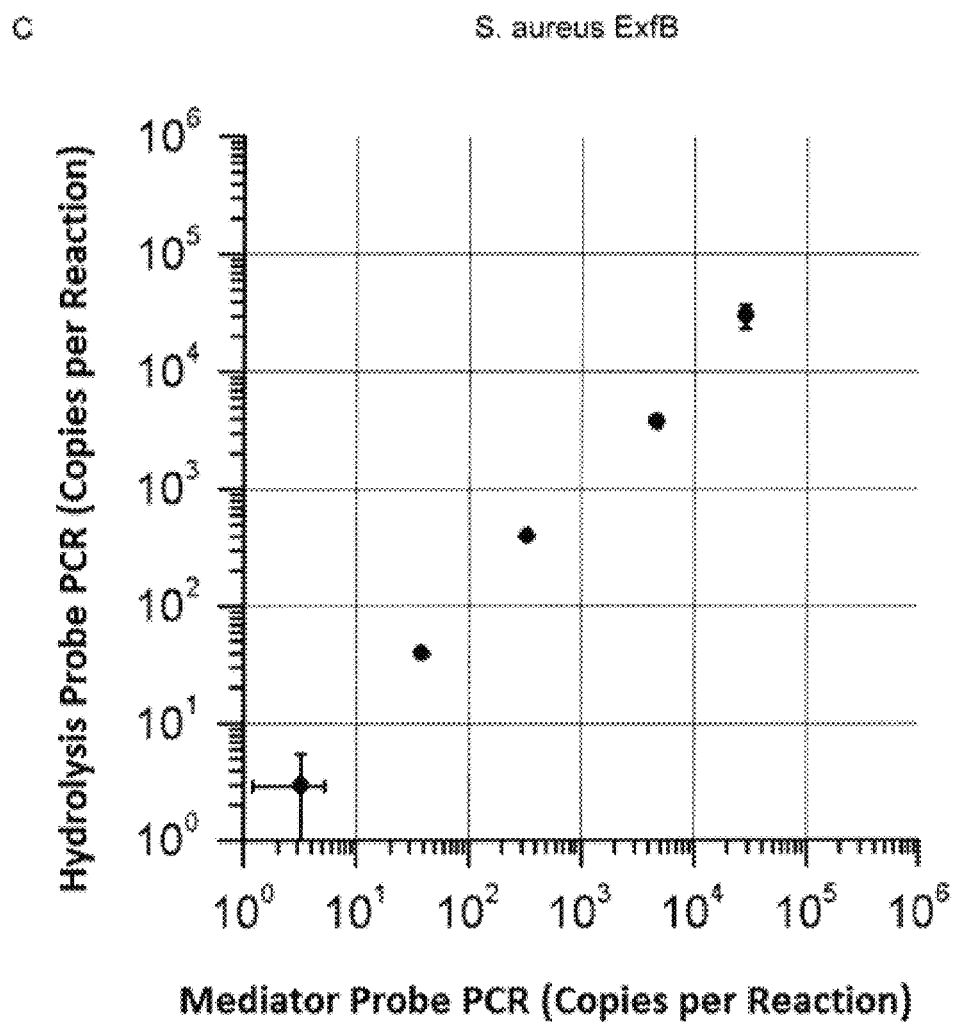
Figure 13:
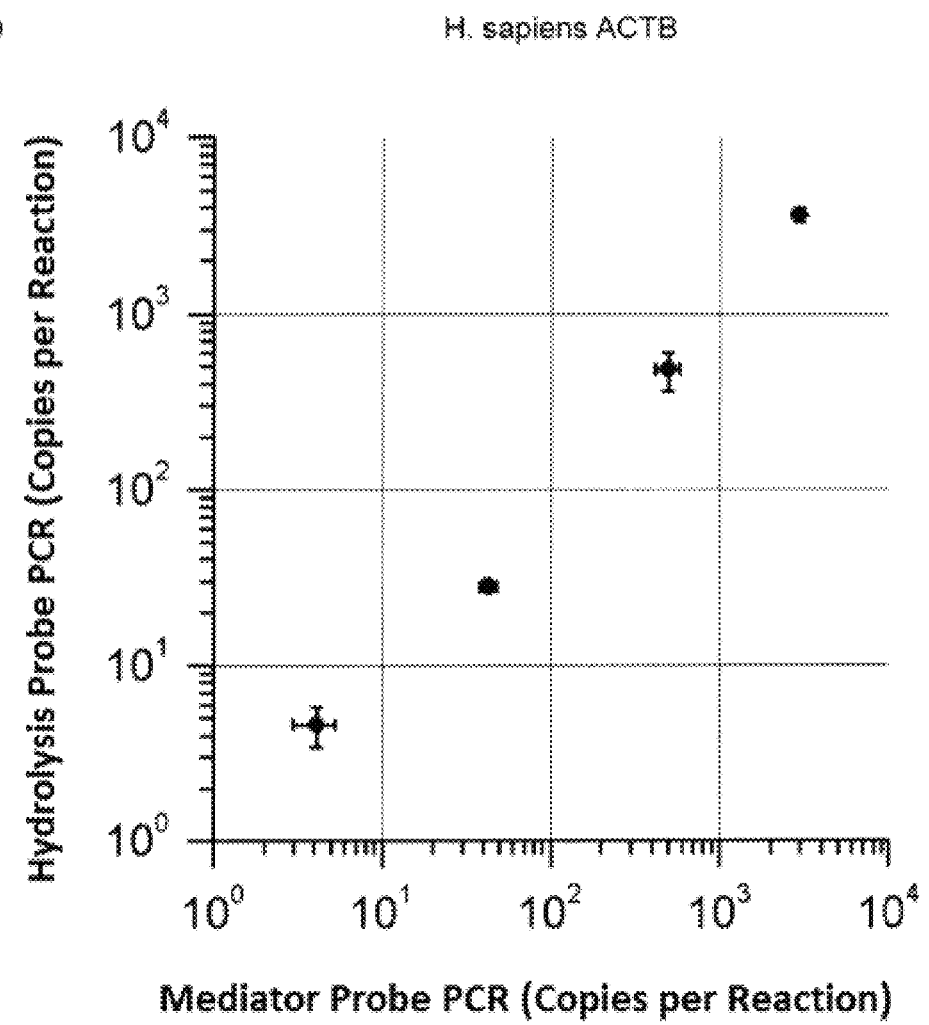

FIG. 13 shows the results of amplification of various targets with mediator probe PCR and hydrolysis probe PCR. (A) HPV18, (B) *E. coli*, (C): *S. aureus*, (D): human beta actin.

Exemplary Embodiment i)

The exemplary embodiments are also diagramed schematically in FIG. 9. A simple demonstration of preferred nucleic acid detection may be performed as follows: for a detection of bacterial DNA in a sample to be analyzed, a detection molecule is immobilized in a suitable reaction vessel. However, the detection molecule may also be present in solution. Next, the sample and the required reagents are added to the reaction vessel, and after an initial temperature holding step at 95° C., the mixture is heated and cooled in cycles. During this process, the fluorescence in the reaction vessel is detected at the defined points in time in the cycle. The exemplary embodiment is described in detail below:

In "NucleoLink strips" (NUNC, Langenselbold, Germany, catalog no. 248650) 25 µL of a 100 nM solution of a detection molecule of the sequence 5'-DABCYL-CCGCA G*A*A*GATGAGATC(dTFAM)GCGGTGTTGGTC-GTAGAGCCCAGAACGAT TTTTTTTTTTTTTTTTTTTTT-[$C_6H_2$]-3' (*=phosphothioate) (IBA, Göttingen, Deutschland) is pipetted into coupling buffer (10 mM 1-methylimidazole (1-Meim) (pH 7.0) (Sigma-Aldrich, Steinheim, Germany) and 10 mM 1-ethyl-3-(3-dimethylaminopropyl)carbodiimide (EDC) (Sigma-Aldrich, Steinheim, Germany)), sealed with ViewSEAL™ cover film (Greiner BioOne, Frickenhausen, Germany, catalog no. 676070) and incubated overnight at 50° C. The supernatant was discarded and the micro reaction vessels were then washed with 100 µL washing buffer (100 mM tris-HCl (pH 7.5), 150 mM NaCl, 0.1% Tween 20 (Carl Roth, Karlsruhe, Germany)) and incubated with 25 µL of a 1M glycine solution (Carl Roth, Karlsruhe, Germany) in coupling buffer for 1 hour at 50° C. and then washed again.

The reaction vessels were filled with 25 µL PCR reaction mix (1× Finnzymes DyNamo Flash probe (Finnzymes, catalog no. F-455), primer molecules of the sequences 5'-GAGGTAGGAAACTCTGGATCAGGTAT-3' (300 nM) (biomers.net, Ulm, Germany), 5'-TCTATT-GAAAAACACTCCTATTGGAAGA-3' (300 nM) (biomers.net, Ulm, Germany), a mediator probe of the sequence 5'-TCTGGGCTCTACGACCAAC AGGTATT-CACAGTGGTAAAGG-CGGACAACAAGAGCCCAG A-[phosphate]-3' (200 nM) (biomers.net, Ulm, Germany)) as well as various concentrations of a *Staphylococcus aureus* DNA containing the exfoliative toxin B locus (NCBI Accession No. M17348). Depending on the DNA concentration, four micro reaction vessels were used. The reaction vessels were sealed with ViewSEAL™ cover film and transferred to a GeneAmp® 9700 thermocycler (Perkin Elmer, Massachusetts). After an incubation phase (7 minutes at 95° C.), the cyclic temperature protocol (30 seconds at 95° C., 3 minutes at 58° C.) was performed and the reaction vessels were removed from the thermocycler after defined cycles and the fluorescein signal was measured with the help of the microtiter plate reader Victor$^2$ 1420 multi-label counter (Perkin Elmer, Massachusetts). Next, the reaction vessels were again transferred to the thermocycler. The fluorescence values of the individual micro reaction vessels were normalized to the respective value of the first cycle, so that an amplification factor could be formulated as a function of the processing cycle for each reaction vessel (see FIG. 10).

Exemplary Embodiment ii)

In a second example, RNA was used as the target molecule. The RNA was transcribed to cDNA by means of a reverse transcription or by another suitable enzymatic system. This step was performed in a separate reaction vessel and one aliquot was added to a detection reaction according to exemplary embodiment i). Alternatively, reverse transcription and subsequent amplification could be performed in the same reaction vessel according to exemplary embodiment i). In this example, expression analysis of one or more genes was of primary concern as the experimental goal.

Exemplary Embodiment iii)

Parallel detection of DNA and RNA in a sample can be performed by combining suitable enzyme systems. In doing so the RNA to be detected is amplified with the help of primers having a defined 5' sequence overhang (see FIG. 9). The mediator probe used for this detection is designed so that it binds partially to the sequence overhang, to the primer and to a segment of the elongated primer. Due to this defined locus, it is certain that only cDNA generated from RNA will be detected by a specific mediator probe but the genomic locus from which the RNA was transcribed will not be detected. For detection of genomic DNA in the reaction batch, mediator probes that are exclusively complementary to this sequence are used. The cDNA was thus generated and specific segments of the genomic DNA are amplified in the amplification reaction which is then optionally performed, in which locus-specific mediator probes are cleaved and the mediator can be detected by suitable detection methods on a locally resolved immobilized detection molecule.

Exemplary Embodiment iv)

Reagents which include the target molecule-specific aptamers and the sample to be analyzed are placed in a suitable reaction vessel, where the detection molecules are immobilized in a locally resolved manner (see FIG. 9) or are present in solution. The target molecule to be detected may be a protein or a peptide, for example, but is not limited to these. An aptamer binds to the target molecule and alters its structure so that after successful interaction an aptamer-specific mediator probe and primer can be annealed. By processing with a suitable enzyme system, the annealed primer can be elongated, whereupon the mediator probe is split off. The mediator thus released can be detected with the help of a specific detection molecule. The enzymatic amplification process may include but is not limited to isothermal methods.

Exemplary Embodiment v)

In a special embodiment variant, DNA, RNA and peptides and/or proteins or another combination of the aforementioned substance classes is/are detected in parallel in one batch by the methods i)-iv) described here. This method includes but is not limited to isothermal amplification methods. This embodiment is illustrated in FIG. 9.

Exemplary Embodiment vi)

Regardless of the type of detection, the reaction vessel may have the established and widespread microtiter plate format (96-well plate), for example, with which commercial temperature regulation and readout devices and/or devices that combine these two functions may be used. In all cases, the detection molecules are immobilized in a locally resolved form (array). A flow cell may also be regarded as a possible reaction vessel, which may optionally be cleaned and reused after the analysis has been performed. In a special embodiment, the reaction vessel may be a cartridge, in which the detection molecules may be present in immobilized form. The reaction space may also be defined by the use of a modified microscope slide and a suitable frame. This embodiment has the advantageous property that the immobilization of the detection molecules on suitable materials is described in the prior art and suitable adhesive frames (Peqlab in situ adhesive frames, Peqlab Biotechnologie, Erlangen, Germany) as well as thermally regulable processing vessels (Peqlab PeqStar in situ, Peqlab Biotechnologie, Erlangen, Germany) and reader devices (BioAnalyzer, LaVision BioTec GmbH, Bielefeld, Germany) are commercially available. The format of the cartridge is not defined and may optionally be created in accordance with the user's wishes. The cartridge can conduct an input beam of light with the help of integrated prisms for excitation of fluorophores near the surface by means of TIRF through a reading range. Furthermore, this cartridge may be used in combination with an instrument having a temperature regulating device and optical components for excitation and detection of fluorescence signals. The cartridge may optionally have microfluidic structures, for example, filling and vent ports, connections for active elements, mixing chambers, measuring chamber and aliquoting chambers, channels or structures or structures that may be used for other purposes. The system may have pumps or other actuators with the help of this the liquid can be processed. In addition, other reagents may also be used.

Exemplary Embodiment vii)

A PCR is performed using a preferred mediator probe according to the invention (see also FIG. 11). For the amplification reaction, normal oligonucleotide primers and a Taq polymerase are used. The mediator probe in the sense of the invention is a bifunctional oligonucleotide, which permits real-time detection of the PCR. To compare the invention with the prior art, these experiments are conducted in parallel with a hydrolysis probe from the prior art.

Sample Material

DNA samples from *Staphylococcus aureus* (Genomic Research Laboratory; Prof. Jacques Schrenzel, Geneva, Switzerland) were used for this experiment. The samples contained the genomic locus of exfoliative toxin B (Gene Bank Accession No. AP003088). The pBR322 plasmid contains the human papilloma virus 18 (HPV18) genome and was made available by GenoID (Budapest, Hungary). *Escherichia coli* K12 DH5-Z1 DNA, which contains the genomic locus of the peptidoglycan-associated lipoprotein (Gene Bank Accession No. 65796) was isolated using a DNA isolation kit based on a magnetic bead. Human genomic DNA was isolated from whole blood using a QIAamp DNA Blood Mini Kit (Qiagen). For the duplex PCR reactions, commercially available human DNA was used (Roche Diagnostics). The DNA samples were diluted in 0.2× Tris-EDTA buffer, and 10 ng/μL salmon sperm DNA (Invitrogen) was added to prevent nonspecific adsorption of the DNA targets onto the reaction vessels, Oligonucleotides The following oligonucleotides were used:

```
Detection molecule 01:
                                      (SEQ ID NO: 1)
CCGCAG*A*A*GATGAGATC(dTFAM)GCGGTGTTGGT- CGTAGAGCCCAGAACGATTTTTTTTTTTTTTTTTTTT
Modifications: 5': DABCYL; 3': C6NH2
* = phosphothioate Detection molecule 02:
                                      (SEQ ID NO: 2)
```

-continued
CCGCAG*A*A*GATGAGATC(dT-Cy5)GCGGTGTTCAC

TGACCGAACTGGAGCATTTTTTTTTTTTTTTTTTT
Modifications: 5': BHQ-2; 3': C₆NH₂

Target: Escherichia coli K12 peptidoglycan-
associated lipoprotein (pal gene), Gene Bank
Accession No. X05123

(SEQ ID NO: 3)
Forward Primer: GGCAATTGCGGCATGTTCTTCC (SEQ ID NO: 4)
Reverse Primer: TGTTGCATTTGCAGACGAGCCT (SEQ ID NO: 5)
Hydrolysis probe: ATGCGAACGGCGGCAACGGCAACATGT Modifications: 5': 6-FAM; 3': BHQ-1
Mediator probe:
(SEQ ID NO: 6)
AAATCGTTCTGGGCTCTACGCGAACGGCGGCAACGGCAACATGT Modification: 3': PH Target: Staphylococcus aureus exfoliative
toxin B
(SEQ ID NO: 7)
Forward primer: AGATGCACGTACTGCTGAAATGAG (SEQ ID NO: 8)
Reverse primer: AATAAAGTACGGATCAACAGCTAAAC (SEQ ID NO: 9)
Hydrolysis probe: CCGCCTACTCCTGGACCAGG Modifications: 5': 6-FAM; 3': BBQ
Mediator probe:
(SEQ ID NO: 10)
AAATCGTTCTGGGCTCTACGGTATTCACAGTGGTAAAGGC-
GGACAACA Modification: 3': PH Target: HPV18 Gene Bank Accession
No. NC_001357.1
(SEQ ID NO: 11)
Forward primer: GCTGGCAGCTCTAGATTATTAACTG (SEQ ID NO: 12)
Reverse primer: GGTCAGGTAACTGCACCCTAA (SEQ ID NO: 13)
Hydrolysis probe: GGTTCCTGCAGGTGGTGGCA Modifications: 5': 6-FAM; 3': BHQ-1
Mediator probe:
(SEQ ID NO: 14)
AAATCGTTCTGGGCTCTACGGTTCCTGCAGGTGGTGGCA
Modifications: 3-PH Target: Homo sapiens ACTB Gene Bank Accession
No. AC_000068.1/HGNC: 132
(SEQ ID NO: 15)
Forward primer: TCACCCACACTGTGCCCATCTACGA (SEQ ID NO: 16)
Reverse primer: CAGCGGAACCGCTCATTGCCAATGG (SEQ ID NO: 17)
Hydrolysis probe 01: ATGCCCTCCCCCATGCCATCCTGCGT Modifications: 5': 6-FAM; 3': DDQ-1
(SEQ ID NO: 18)
Hydrolysis probe 02: ATGCCCTCCCCCATGCCATCCTGCGT Modifications: 5' Cy5; 3': DDQ-2
Mediator probe 01:
(SEQ ID NO: 19)
AAATCGTTCTGGGCTCTACGCCCTCCCCCATGCCATCCTGCGT Modification: 3': PH -continued
Mediator probe 02:
(SEQ ID NO: 20)
ATGCTCCAGTTCGGTCAGTGCCCTCCCCCATGCCATCCTGCGT
Modification: 3': PH All the modified oligonucleotides were purified with HPLC.

The mediator probes were designed in a two-step process. The probe region and the mediator region overlap with a nucleotide. The 5' end of the probe region must therefore match the 3' end of the mediator region. In the present experiment, a guanosine nucleotide was used for this purpose. The probe region was designed according to the guidelines for development of a hydrolysis probe: length 25-30 nucleotides, probe melting temperature 5-10° C. and greater than the primer melting point). The mediator region was designed so that this region would not have any homologies with the target. The 3'-terminus is blocked with a phosphate group to prevent elongation of the mediator probe.

The design for the detection molecules was created in silico to obtain a hairpin structure with an unpaired single-stranded 3' stock. Predictions about the secondary structure were made using RNAfold, and the melting point was calculated using VisOMP (Visual Oligonucleotide Modeling Program). For the secondary structure, the settings "no dangling end energies," "DNA settings," "60° C." were selected in the "advanced folding" option. The melting point of the strain (GC content 71%) is 71.4° C., which allows refolding during the cooling step (60° C.) during each thermal cycle. The folded structure provides a FRET pair, where the pair is arranged onto two strands enclosed in spatial proximity to one another. The FRET pair comprises a 5' terminal quencher, and an internal fluorophore is selected to achieve a high quenching efficiency. The 3' unpaired strain comprises the binding site for the mediator region, which is the reverse complement to the mediator region. To prevent elongation of the detection molecule, the 3'-terminus was blocked with an amino group. A second detection molecule was designed for the duplex PCR experiments, wherein this has a sequence identical to that of the first detection molecule except that a modified mediator binding site and another FRET pair were used.

Quenching Efficiency

The selection of suitable fluorophore dyes and quencher radicals was especially important in order to permit a high quenching efficiency and analytical sensitivity for the detection of particularly small amounts of nucleic acids. To determine the quenching efficiency, the fluorescence emission was determined for each dual-labeled hydrolysis probe and detection molecule, with and without DNase I treatment. The quenching efficiency (Eq) is determined as follows:

$$Eq = 1 - (I_{undigested}/I_{digested}) \times 100$$

where $I_{undigested}$ is the fluorescence emission of undigested sample and $I_{digested}$ is the fluorescence emission of samples treated with DNaseI.

Mediator Probe PCR and Hydrolysis Probe PCR Experiments

The mediator probe PCR reaction batch contains 1×PCR buffer (GenoID, Budapest, Hungary), 0.1 U/μL Hot StarTaq plus polymerase (Qiagen), 200 μmol/L deoxyribonucleotide (Qiagen), 300 nmol/L detection molecule (synthesized by IBA), 300 nmol/L target-specific primer pairs and 200 nmol/L mediator probe (synthesized by biomers.net). The hydrolysis probe PCR reaction batch contains the same quantities of reagents except for the mediator probe, which was replaced by the hydrolysis probe (200 nmol/L, synthesized by biomers.net). Furthermore, no detection molecules were added. Next, DNA template molecules were added to both batches (in the negative controls, the same amount of $H_2O$ was added instead). The reaction volume was 10 µL.

All the real-time PCR reactions were performed in a Corbett Rotor Gene 6000 (Corbett Research Pty, now Qiagen GmbH) with the following universal thermocycling profile:
- initial polymerase activation: 95° C. for 5 minutes
- 45 cycles with denaturing at 95° C. for 15 seconds and
- a combined annealing and elongation step at 60° C. for 45 seconds.

The fluorescence signals were performed at the end of each elongation step. Data analysis was performed using the Rotor Gene 6000 software (version 1.7.87).

Statistical Analysis

The limit of detection (LOD) for HPV18 detection was determined as follows:

Various DNA concentrations were amplified ($10^4$, $10^3$, $5 \times 10^2$, $10^2$, $5 \times 10^1$, $10^1$, $10^0$ and $10^{-1}$ copies per reaction). The amount of positive amplifications per DNA concentration was determined. Probit analyses with SPSS (Statistical Package for Social Sciences, version 19, IBM) allow a prediction of the number of copies per reaction, which leads to positive amplification results with a 95% probability.

Results

Quenching Efficiency

Fluorescence emission of all fluorogenic molecules increased in degradation in comparison with undigested probes. The observed Eq values of the specific hydrolysis probes were between 54.5% (3.1%) [Cy5/2,3-dichloro-5,6-dicyano-1,4-benzoquinone-2 (DDQ-2)] and 92.7% (0.5%) [FAM/di-tert-butylhydroquinone-1 (BHQ-1)]. However, the quenching efficiency of the detection molecules was between 83.7% (1.4%) (Cy5/BHQ-2) and 90.9% (0.4%) (FAM/Dabcyl). These results correspond to the known Eq values for FAM/Dabcyl (80-91%), FAM/BHQ-1 (88-93%) and Cy5/BHQ-2 (91-96%) under optimized conditions.

Mediator Probe PCR Vs. Hydrolysis Probe PCR

In the present experiments, the mediator probe PCR was compared with the hydrolysis probe PCR. Firstly, the reaction efficiency, the LOD, the interassay variation, the intra-assay variation and the duplexing properties were analyzed. For these experiments, different concentrations of HPV18 DNA ($10^2$, $10^3$, $10^4$, $10^5$ and $10^6$ copies per reaction, unless otherwise described) were amplified with parallel use of both techniques. Secondly, different targets were amplified with parallel use of the two techniques.

LOD (Limit of Detection)

The LOD was determined as the DNA concentration resulting in a positive amplification with a 95% probability. Probit analyses revealed an analytical sensitivity of 78.3 copies per reaction (95% CI: 47.0-372.5 copies per reaction) for the mediator probe PCR and 85.1 copies per reaction (95% CI: 55.7-209.4 copies per reaction) for the hydrolysis probe PCR (FIG. 12A).

Intra-Assay Variance

Five concentrations of the HPV18 DNA dilution series ($10^2$, $10^3$, $10^4$, $10^5$ and $10^6$ copies per reaction) were amplified in eight repetitions. The $R^2$ values 0.975 (mediator probe PCR) and 0.983 (hydrolysis probe PCR) showed excellent linearity (FIG. 12B). Percentage CVs for the amplification of $10^2$-$10^6$ copies per reaction were 55.1%-9.9% (mediator probe PCR) and 38.3%-10.7% (hydrolysis probe PCR). The accuracy ranges from +21.6% to −8.1% (mediator probe PCR) and from +19.4% to −9.8% (hydrolysis probe PCR).

Interassay Variance

Five batches prepared separately were used for the amplification of five concentrations of HPV18 DNA dilution series ($10^2$, $10^3$, $10^4$, $10^5$ and $10^6$ copies per reaction). Each concentration was prepared three times. The $R^2$ values 0.940 (mediator probe PCR) and 0.954 (hydrolysis probe PCR) showed the linearity of the amplification (FIG. 12C). The interassay variance for copy numbers of $10^2$-$10^6$ per reaction was between 25% and 8.7% (mediator probe PCR) and between 34.7% and 12.7% (hydrolysis probe PCR). The accuracy ranges from +3.4% to −7% (mediator probe PCR) and from −2% to −12.4% (hydrolysis probe PCR).

Duplex Amplification

A fragment of a plasmid containing HPV18 DNA ($10^2$, $10^3$, $10^4$, $10^5$ and $10^6$ original copies) was co-amplified with 300 copies of the *Homo sapiens* genome. The respective reactions were performed in a triple batch. The hydrolysis probe for HPV18 was labeled with FAM/BHQ-1 and the probe for actin beta (ACTB) was labeled with Cy5/DDQ-2. For the duplex PCR, the detection molecule $O_1$ was labeled with FAM/Dabcyl and the detection molecule $O_2$ was labeled with Cy5/BHQ-2. FIG. 12D shows the linearity of the HPV18 amplification for the different DNA concentrations for the mediator probe PCR ($R^2=0.998$) and for the hydrolysis probe PCR ($R^2=0.988$). Calculation of the ACTB values could not be counted because only one concentration was used in the duplex experiment.

The cycle values (cycle of quantification; Cq) were determined with a threshold value of 0.02 in the red channel for mediator probe PCR and hydrolysis probe PCR. The average Cq values for co-amplified ACTB and HPV18 DNA samples were 33.0 (0.5) and 31.8 (0.4) for mediator probe PCR and hydrolysis probe PCR.

Various Targets

The universal nature of mediator probe PCR was illustrated by tests using four clinically relevant targets. For the comparison, the hydrolysis probe PCR was conducted in parallel for each target. The linearity between input and calculated output copy number was determined for each target and for each amplification technique (FIG. 13). The results for detection of the dilution series of the HPV18 L1 gene (mediator probe PCR $R^2=0.999$/hydrolysis probe PCR $R^2=0.975$), *S. aureus* exfoliative toxin B gene (0.991/0.988), *E. coli* peptidoglycan-associated lipoprotein (*E. coli* pal) gene (0.996/0.988) and human beta actin gene (0.991/0.993) show a high correlation between the two methods of PCR:

| Target | Input copy number, n | Mediator probe PCR | | | Hydrolysis probe PCR | | |
|---|---|---|---|---|---|---|---|
| | | Output, n | SD | % CV | Output, n | SD | % CV |
| HPV18 L7 | $1.0 \times 10^5$ | $1.1 \times 10^5$ | $4.2 \times 10^3$ | 4.0 | $1.1 \times 10^5$ | $4.1 \times 10^3$ | 3.8 |
| | $1.0 \times 10^4$ | $9.1 \times 10^3$ | $3.6 \times 10^3$ | 4.0 | $1.0 \times 10^4$ | $1.5 \times 10^3$ | 14.6 |
| | $1.0 \times 10^2$ | $1.0 \times 10^2$ | $5.9 \times 10^2$ | 5.8 | $8.7 \times 10^2$ | $4.4 \times 10^2$ | 50.9 |
| | $1.0 \times 10^2$ | $1.0 \times 10^2$ | $1.4 \times 10^1$ | 13.2 | $1.3 \times 10^2$ | $5.1 \times 10^1$ | 39.0 |

-continued

| Target | Input copy number, n | Mediator probe PCR Output, n | SD | % CV | Hydrolysis probe PCR Output, n | SD | % CV |
|---|---|---|---|---|---|---|---|
| E. Coli pa[a] | $6.3 \times 10^4$ | $5.5 \times 10^4$ | $1.1 \times 10^3$ | 1.9 | $6.4 \times 10^4$ | $5.6 \times 10^3$ | 8.9 |
| | $6.3 \times 10^3$ | $7.1 \times 10^3$ | $5.3 \times 10^2$ | 7.5 | $7.3 \times 10^3$ | $3.2 \times 10^2$ | 4.3 |
| | $6.3 \times 10^2$ | $6.7 \times 10^2$ | $40.7 \times 10^1$ | 6.1 | $5.9 \times 10^2$ | $1.4 \times 10^2$ | 23.2 |
| | $6.3 \times 10^1$ | $7.1 \times 10^1$ | $20.7 \times 10^1$ | 29.2 | $5.1 \times 10^1$ | $20.5 \times 10^1$ | 40.2 |
| S. aureus exfB | $3.0 \times 10^4$ | $2.9 \times 10^4$ | $2.6 \times 10^3$ | 0.9 | $3.0 \times 10^4$ | $6.8 \times 10^3$ | 0.9 |
| | $3.0 \times 10^3$ | $4.7 \times 10^3$ | $3.9 \times 10^3$ | 8.4 | $3.8 \times 10^3$ | $2.5 \times 10^2$ | 6.7 |
| | $3.0 \times 10^2$ | $3.3 \times 10^2$ | $3.1 \times 10^1$ | 9.4 | $4.0 \times 10^2$ | $20.8 \times 10^1$ | 5.2 |
| | $3.0 \times 10^1$ | $3.8 \times 10^1$ | $2.4 \times 10^0$ | 6.3 | $4.0 \times 10^1$ | $3.1 \times 10^0$ | 7.8 |
| | $3.0 \times 10^0$ | $3.2 \times 10^0$ | $2.0 \times 10^0$ | 62.5 | $2.9 \times 10^0$ | $2.6 \times 10^0$ | 89.7 |
| H. sapiens ACTB | $4.0 \times 10^3$ | $2.9 \times 10^3$ | $1.6 \times 10^2$ | 5.4 | $3.6 \times 10^3$ | $3.4 \times 10^2$ | 9.4 |
| | $4.0 \times 10^2$ | $4.9 \times 10^2$ | $7.8 \times 10^1$ | 15.8 | $4.8 \times 10^2$ | $1.2 \times 10^2$ | 25.0 |
| | $4.0 \times 10^1$ | $4.3 \times 10^1$ | $5.2 \times 10^0$ | 12.1 | $2.8 \times 10^1$ | $1.6 \times 10^0$ | 5.7 |
| | $4.0 \times 10^0$ | $4.1 \times 10^0$ | $1.1 \times 10^0$ | 26.8 | $4.6 \times 10^1$ | $1.2 \times 10^0$ | 26.1 |
| Coamplification | | | | | | | |
| HPV18 L1 | $1.0 \times 10^6$ | $1.1 \times 10^6$ | $3.5 \times 10^4$ | 3.4 | $1.0 \times 10^5$ | $9.3 \times 10^4$ | 9.1 |
| | $1.0 \times 10^5$ | $8.1 \times 10^4$ | $6.3 \times 10^3$ | 8.5 | $1.2 \times 10^5$ | $2.2 \times 10^4$ | 18.9 |
| | $1.0 \times 10^4$ | $1.2 \times 10^4$ | $1.7 \times 10^3$ | 15.1 | $7.9 \times 10^2$ | $6.1 \times 10^2$ | 7.8 |
| | $1.0 \times 10^3$ | $1.1 \times 10^3$ | $7.7 \times 10^1$ | 6.7 | $1.0 \times 10^2$ | $3.1 \times 10^2$ | 30.3 |
| | $1.0 \times 10^2$ | $9.6 \times 10^1$ | $3.5 \times 10^1$ | 36.8 | $1.2 \times 10^2$ | $5.6 \times 10^1$ | 45.5 |
| H. sapiens ACTB[b] | $3.0 \times 10^2$ | $C_q$: 33.0 | ±0.5 | | $C_q$: 31.8 | ±0.4 | |

[a] Calculated copy numbers (no output) of 4 targets amplified with mediator probe PCR and hydrolysis probe PCR SD and imprecision (% CV) were calculated for each target and copy number.
[b] Quantification of copy number is not feasible. The threshold for ACTB was set to 0.00 and obtained $C_q$ values are presented.

DISCUSSION

The excellent feature of the test shown here is the decoupling of amplification and fluorescence detection which makes it possible to use a standardized detection molecule. The sequences of the mediator region and of the detection molecule were designed in silico and, according to a BLAST search, do not show any correspondence with the targets. The detection molecule has a hairpin secondary structure and therefore presents optimal FRET quenching conditions [>90% (FAM/Dabcyl), >80% (Cy5/BHQ-2)]. The spatial proximity between the fluorophore and the quencher within the hairpin structure results in a high and constant quenching efficiency. In contrast with the results shown here, FAM-labeled hydrolysis probes from the prior art regularly yield quenching efficiencies of 60% to 93%, depending on the different quenching radicals and the distances between the donor and the acceptor. The Cy5/DDQ-2-labeled hydrolysis probe had a low Eq value of only 55%.

Amplification of HPV18 DNA was selected as a model assay to compare the new mediator probe and the hydrolysis probe, the gold standard from the prior art, with one another.

The LOD was determined for both probes using probit analyses (mediator probe: 78.3; hydrolysis probe: 85.1 copies per reaction). Interassay and intra-assay variance for $10^2$ to $10^6$ copies per reaction were of the same order of magnitude (mediator probe 25%-8.7%, 55.1%-9.9%; hydrolysis probe 34.7%-12.7%, 38.3%-10.7%).

A reduction in the elongation time in various PCR tests from 50 second to 6 seconds did not have a negative effect on quantification. These results show that mediator probe PCR is suitable for rapid-cycling protocols, which can be performed with the most up-to-date real-time thermocyclers.

Two different detection molecules with different hybridization sequences and FRET modification were designed. These reporter systems are capable of detecting any target gene combination, wherein these systems reduce costs and can be used as routine diagnostic tests. Thus co-amplification of different amounts of HPV18 DNA and a constant copy number of ACTB were demonstrated successfully.

The invention claimed is:

1. A method for detection of a target nucleic acid molecule from at least one target molecule in a sample, the method comprising:
providing a sample comprising [one target molecule of] the at least one target molecule that is a [DNA] nucleic acid sequence,
bringing said sample into contact with one system comprising:
(i) a mediator probe, the mediator probe being an oligonucleotide comprising a probe region on [a] its 3'-terminus [of the oligonucleotide], and
a mediator region on [a] its 5'-terminus [of the oligonucleotide], and a chemical, biological [and/] or physical cleavage site between the probe region and the mediator region, and (ii) a detection molecule,
wherein the probe region of the mediator probe [has an affinity for] is complementary to the [one] target nucleic acid molecule and comprises a locus-specific nucleotide sequence complementary to a sequence of the [one] target nucleic acid molecule, and wherein the mediator region of the mediator probe [has no affinity for the one target molecule,] does not comprise a sequence complementary to a sequence of the [one] target nucleic acid molecule, and comprises a locus-nonspecific nucleotide sequence,
[binding] hybridizing the probe region of the mediator probe to [a] the sequence of the [one] target nucleic acid molecule, while the mediator region does not [bind] hybridize to the target nucleic acid molecule so that a flap structure is formed in a first hybridization complex comprising the mediator probe and the target nucleic acid molecule,
amplifying the target nucleic acid molecule in the first hybridization complex using a DNA polymerase with 5' to 3' nuclease activity,
splitting off the mediator region from the mediated probe at the cleavage site during said amplifying of the target nucleic acid molecule in the first hybridization complex by [a DNA polymerase with] 5' to 3' nuclease activity of the DNA polymerase, thereby producing [to produce] a cleaved mediator region, and
hybridizing of the cleaved mediator region to a second region of the detection molecule, thereby forming a second hybridization complex comprising the cleaved mediator region and the detection molecule, the detection molecule being an oligonucleotide having a hairpin structure comprising:
[b)] a first region on [a] its 5'-terminus, which has one fluorescence acceptor or one fluorescence donor and optionally a chemical group for binding the detection molecule to a solid phase and/or a chemical protective group, and which is hybridized with [an internal sequence segment] a third region of the detection molecule, wherein the third region [internal sequence segment] is located on 5' [to] of the second region and forms a double-stranded stem region with the first region, and there is a loop region between the first region and the third region,
[c)] the second region [adapted to bind the cleaved mediator region and] comprising a locus-nonspecific nucleotide sequence [of the detection molecule] which is complementary to the locus-nonspecific nucleotide sequence of the [cleaved] mediator region and non-complementary to the target nucleic acid molecule, wherein the second region is located on 3' [to] of the third region [internal sequence segment] and comprises an unpaired sequence segment at the 3' terminus of the detection molecule, and
[d)] [a] the third region, which has one fluorescence donor or one fluorescence acceptor which interacts with the one fluorescence acceptor or the one fluorescence donor of the first region and optionally a chemical protective group, wherein the one fluorescence acceptor or the one fluorescence donor of the first region and the one fluorescence donor or the one fluorescence acceptor of the third region are in spatial proximity to one another such that a fluorescent signal of the one fluorescent donor of the detection molecule is suppressed,
elongating the cleaved mediator region [hybridized to the second region of the detection molecule] of the second hybridization complex by a polymerase with 5' to 3' nuclease activity, wherein [elongation of] said elongating the cleaved mediator region [hybridized to the second region of the detection molecule] of the second hybridization complex triggers a [detectable change of the] fluorescence signal of the one fluorescent donor of the detection molecule, and
detecting the [one] target nucleic acid molecule [of] from the at least one target molecule in the sample via [the change of] detecting the fluorescence signal of the one fluorescent donor of the detection molecule.

2. The method according to claim 1, wherein the probe region of the mediator probe hybridizes directly to the sequence of the target nucleic acid molecule.

3. The method according to claim 1, wherein said amplifying the target molecule in the first hybridization complex is accomplished by polymerase chain reaction (PCR).

4. The method of claim 3, wherein the PCR is real time PCR.

5. The method of claim 1, wherein the detection molecule has a chemical protective group on [the] its 3'-terminal region, which is split off from the detection molecule after the elongation step, and a OH group is generated in the 3' terminus of the detection molecule [modified in] after the elongation step.

6. A method for detection of a target [desoxyribonucleic] deoxyribonucleic acid (DNA) sequence [of] from at least one target molecule in a sample, the method comprising:
providing a sample comprising the at least one target molecule,
bringing said sample into contact with one system comprising:
(i) a mediator probe, the mediator probe being an oligonucleotide comprising a probe region on [a] its 3'-terminus [of the oligonucleotide], and
a mediator region on [a] its 5'-terminus [of the oligonucleotide], and a chemical, biological [and/] or physical cleavage site between the probe region and the mediator region, and
(ii) a detection molecule,
wherein the detection molecule is an oligonucleotide comprising a hairpin structure, wherein the detection molecule comprises a first region, a second region [and], a third region, and a loop region between the first region and the third region; wherein the mediator region of the mediator probe [has an affinity] comprises a locus-nonspecific nucleotide sequence that is complementary to a locus-nonspecific nucleotide sequence of the second region [of the hairpin structure] of the detection molecule, but [has no affinity for the one target molecule,] does not comprise a sequence complementary to [a] the target DNA sequence of the at least one target molecule, [and comprises a locus-nonspecific nucleotide sequence,] and wherein the probe region of the mediator probe [has an affinity for the one target molecule and] comprises a locus-specific nucleotide sequence complementary to [a] the target DNA sequence of the at least one target molecule,

[binding] hybridizing the probe region of the mediator probe to the target DNA sequence of the at least one target molecule, while the mediator region does not bind to the target DNA sequence of the at least target molecule so that a flap structure is formed in a first hybridization complex comprising the mediator probe and the target DNA sequence of the at least one target molecule, amplifying the target DNA sequence in the first hybridization complex using a DNA polymerase with 5' to 3' nuclease activity, cleaving off the mediator region from the mediated probe at the cleavage site during said amplifying of the target DNA sequence in the first hybridization complex via [a DNA polymerase with] 5' to 3' nuclease activity of the DNA polymerase, thereby producing [to produce] a cleaved off mediator region, and hybridizing of the cleaved off mediator region to the second region of the detection molecule, thereby forming a second hybridization complex comprising the cleaved off mediator region and the detection molecule, wherein:

the first region on [a] 5'-terminus [of the hairpin structure] of detection molecule comprises one first fluorescence acceptor or one first fluorescence donor, the second region of the detection molecule [binds] is a single stranded region located on 3' of the third region and hybridizes the cleaved off mediator region via the [and comprises a] locus-nonspecific nucleotide sequence of the detection molecule which is complementary to the locus-nonspecific nucleotide sequence of the [cleaved off] mediator region and non-complementary to the target DNA sequence of the at least one target molecule, and wherein the detection molecule optionally comprises a chemical group for binding the detection molecule to a solid phase and/or a chemical protective group, the third region forms a double-stranded stem region with the first region, wherein the one first fluorescence acceptor of the first region is in spatial proximity to a second fluorescence donor, located at [a] the third region located on 3' of the first region of the detection molecule, and that is adapted to interact with the one first fluorescence acceptor, or the one first fluorescence donor of the first region is in spatial proximity to a second fluorescent acceptor, located at [a] the third region 3' of the first region of the detection molecule, and that is adapted to interact with the one first fluorescence donor [acceptor] such that a fluorescence signal of the one first fluorescence donor or the second fluorescence donor of the detection molecule is suppressed, elongating the cleaved mediator region [hybridized to the second region of the detection molecule] of the second hybridization complex via a polymerase with 5' to 3' nuclease activity, wherein [elongation of] said elongating the cleaved mediator region [hybridized to the second region of the detection molecule] of the second hybridization complex triggers a [detectable change of the] fluorescence signal of the one first fluorescence donor or the second fluorescence donor of the detection molecule, and detecting the [one] target DNA sequence of the at least one target molecule in the sample via [the detectable change of] detecting the fluorescence signal of the one first fluorescence donor or the second fluorescence donor of the detection molecule.

\* \* \* \* \*

UNITED STATES PATENT AND TRADEMARK OFFICE
CERTIFICATE OF CORRECTION

| | | |
|---|---|---|
| PATENT NO. | : 11,293,053 B2 | Page 1 of 4 |
| APPLICATION NO. | : 14/357574 | |
| DATED | : April 5, 2022 | |
| INVENTOR(S) | : Roth et al. | |

It is certified that error appears in the above-identified patent and that said Letters Patent is hereby corrected as shown below:

On the Title Page

On Page 2, item (56) in Column 2, under "OTHER PUBLICATIONS", Line 7, delete "Self-Quneched" and insert -- Self-Quenched --, therefor.

In the Specification

In Column 20, Line 26, delete "phosphotioates" and insert -- phosphorothioates --, therefor.

In Column 25, Lines 41-42, delete "phosphothioate" and insert -- phosphorothioate --, therefor.

In Column 32, Lines 16-17, delete "(*=phosphothioate)" and insert -- (*=phosphorothioate) --, therefor.

In Column 34, Line 64, delete "phosphothioate" and insert -- phosphorothioate --, therefor.

In the Claims

In Column 47, in Claim 1, Lines 5-6, delete "[one target molecule of] the at least one target molecule that is a [DNA]" and insert -- the at least one target molecule that is a --, therefor.

In Column 47, in Claim 1, Lines 12-13, delete "[a] its 3'-terminus [of the oligonucleotide]," and insert -- its 3'-terminus, --, therefor.

In Column 47, in Claim 1, Lines 14-15, delete "[a] its 5'-terminus [of the oligonucleotide], and a chemical, biological [and/]" and insert -- its 5'-terminus, and a chemical, biological --, therefor.

In Column 47, in Claim 1, Lines 18-19, delete "[has an affinity for] is complementary to the [one]" and insert -- is complementary to the --, therefor.

Signed and Sealed this
Tenth Day of January, 2023

Katherine Kelly Vidal
*Director of the United States Patent and Trademark Office*

In Column 47, in Claim 1, Lines 22-25, delete "[one] target nucleic acid molecule, and wherein the mediator region of the mediator probe [has no affinity for the one target molecule,] does not comprise a sequence complementary to a sequence of the [one]" and insert -- target nucleic acid molecule, and wherein the mediator region of the mediator probe does not comprise a sequence complementary to a sequence of the --, therefor.

In Column 47, in Claim 1, Lines 28-31, delete "[binding] hybridizing the probe region of the mediator probe to [a] the sequence of the [one] target nucleic acid molecule, while the mediator region does not [bind]" and insert -- hybridizing the probe region of the mediator probe to the sequence of the target nucleic acid molecule, while the mediator region does not --, therefor.

In Column 47, in Claim 1, Lines 42-44, delete "[a DNA polymerase with] 5' to 3' nuclease activity of the DNA polymerase, thereby producing [to produce]" and insert -- 5' to 3' nuclease activity of the DNA polymerase, thereby producing --, therefor.

In Column 47, in Claim 1, Line 51, delete "[b)] a first region on [a]" and insert -- a first region on --, therefor.

In Column 47, in Claim 1, Lines 55-57, delete "[an internal sequence segment] a third region of the detection molecule, wherein the third region [internal sequence segment] is located on 5' [to]" and insert -- a third region of the detection molecule, wherein the third region is located on 5' --, therefor.

In Column 47, in Claim 1, Lines 61-67, delete "[c)] the second region [adapted to bind the cleaved mediator region and] comprising a locus-nonspecific nucleotide sequence [of the detection molecule] which is complementary to the locus-nonspecific nucleotide sequence of the [cleaved] mediator region and non-complementary to the target nucleic acid molecule, wherein the second region is located on 3' [to]" and insert -- the second region comprising a locus-nonspecific nucleotide sequence which is complementary to the locus-nonspecific nucleotide sequence of the mediator region and non-complementary to the target nucleic acid molecule, wherein the second region is located on 3' --, therefor.

In Column 48, in Claim 1, Line 1, delete "[internal sequence segment] and" and insert -- and --, therefor.

In Column 48, in Claim 1, Line 4, delete "[d)] [a] the" and insert -- the --, therefor.

In Column 48, in Claim 1, Lines 14-21, delete "[hybridized to the second region of the detection molecule] of the second hybridization complex by a polymerase with 5' to 3' nuclease activity, wherein [elongation of] said elongating the cleaved mediator region [hybridized to the second region of the detection molecule] of the second hybridization complex triggers a [detectable change of the]" and insert -- of the second hybridization complex by a polymerase with 5' to 3' nuclease activity, wherein said elongating the cleaved mediator region of the second hybridization complex triggers a --, therefor.

CERTIFICATE OF CORRECTION (continued)
U.S. Pat. No. 11,293,053 B2

In Column 48, in Claim 1, Lines 23-25, delete "[one] target nucleic acid molecule [of] from the at least one target molecule in the sample via [the change of]" and insert -- target nucleic acid molecule from the at least one target molecule in the sample via --, therefor.

In Column 48, in Claim 5, Line 36, delete "on [the]" and insert -- on --, therefor.

In Column 48, in Claim 5, Line 39, delete "molecule [modified in]" and insert -- molecule --, therefor.

In Column 48, in Claim 6, Lines 41-42, delete "[desoxyribonucleic] deoxyribonucleic acid (DNA) sequence [of]" and insert -- deoxyribonucleic acid (DNA) sequence --, therefor.

In Column 48, in Claim 6, Lines 49-50, delete "[a] its 3'-terminus [of the oligonucleotide]," and insert -- its 3'-terminus, --, therefor.

In Column 48, in Claim 6, Lines 51-52, delete "[a] its 5'-terminus [of the oligonucleotide], and a chemical, biological [and/]" and insert -- its 5'-terminus, and a chemical, biological --, therefor.

In Column 48, in Claim 6, Lines 59-67, delete "[and], a third region, and a loop region between the first region and the third region; wherein the mediator region of the mediator probe [has an affinity] comprises a locus-nonspecific nucleotide sequence that is complementary to a locus-nonspecific nucleotide sequence of the second region [of the hairpin structure] of the detection molecule, but [has no affinity for the one target molecule,] does not comprise a sequence complementary to [a]" and insert -- , a third region, and a loop region between the first region and the third region; wherein the mediator region of the mediator probe comprises a locus-nonspecific nucleotide sequence that is complementary to a locus-nonspecific nucleotide sequence of the second region of the detection molecule, but does not comprise a sequence complementary to --, therefor.

In Column 49, in Claim 6, Lines 1-5, delete "[and comprises a locus-nonspecific nucleotide sequence,] and wherein the probe region of the mediator probe [has an affinity for the one target molecule and] comprises a locus-specific nucleotide sequence complementary to [a]" and insert -- and wherein the probe region of the mediator probe comprises a locus-specific nucleotide sequence complementary to --, therefor.

In Column 49, in Claim 6, Line 5, delete "[binding] hybridizing" and insert -- hybridizing --, therefor.

In Column 49, in Claim 6, Lines 20-22, delete "[a DNA polymerase with] 5' to 3' nuclease activity of the DNA polymerase, thereby producing [to produce]" and insert -- 5' to 3' nuclease activity of the DNA polymerase, thereby producing --, therefor.

In Column 49, in Claim 6, Line 29, delete "[a] 5'-terminus [of the hairpin structure]" and insert -- 5'-terminus --, therefor.

In Column 49, in Claim 6, Lines 32-35, delete "[binds] is a single stranded region located on 3' of the third region and hybridizes the cleaved off mediator region via the [and comprises a]" and insert -- is a single stranded region located on 3' of the third region and hybridizes the cleaved off mediator region via the --, therefor.

CERTIFICATE OF CORRECTION (continued)
U.S. Pat. No. 11,293,053 B2

In Column 50, in Claim 6, Line 1, delete "[cleaved off] mediator" and insert -- mediator --, therefor.

In Column 50, in Claim 6, Line 10, delete "[a] the" and insert -- the --, therefor.

In Column 50, in Claim 6, Lines 16-18, delete "[a] the third region 3' of the first region of the detection molecule, and that is adapted to interact with the one first fluorescence donor [acceptor]" and insert -- the third region 3' of the first region of the detection molecule, and that is adapted to interact with the one first fluorescence donor --, therefor.

In Column 50, in Claim 6, Lines 22-29, delete "[hybridized to the second region of the detection molecule] of the second hybridization complex via a polymerase with 5' to 3' nuclease activity, wherein [elongation of] said elongating the cleaved mediator region [hybridized to the second region of the detection molecule] of the second hybridization complex triggers a [detectable change of the]" and insert -- of the second hybridization complex via a polymerase with 5' to 3' nuclease activity, wherein said elongating the cleaved mediator region of the second hybridization complex triggers a --, therefor.

In Column 50, in Claim 6, Lines 32-34, delete "[one] target DNA sequence of the at least one target molecule in the sample via [the detectable change of]" and insert -- target DNA sequence of the at least one target molecule in the sample via --, therefor.